United States Patent
Bansal

(10) Patent No.: US 9,745,367 B2
(45) Date of Patent: Aug. 29, 2017

(54) ALTERNATIVE PATHWAY SPECIFIC ANTIBODIES FOR TREATING ARTHRITIS

(71) Applicant: Rekha Bansal, Twinsburg, OH (US)

(72) Inventor: Rekha Bansal, Twinsburg, OH (US)

(73) Assignee: Novelmed Theraputics, Inc., Cleveland, OH (US)

( * ) Notice: Subject to any disclaimer, the term of this patent is extended or adjusted under 35 U.S.C. 154(b) by 279 days.

(21) Appl. No.: 13/646,286

(22) Filed: Oct. 5, 2012

(65) Prior Publication Data

US 2013/0039925 A1 Feb. 14, 2013

Related U.S. Application Data

(63) Continuation-in-part of application No. PCT/US2011/026841, filed on Mar. 2, 2011, and a continuation-in-part of application No. PCT/US2011/027964, filed on Mar. 10, 2011, which is a continuation-in-part of application No. 12/920,997, filed as application No. PCT/US2008/068530 on Jun. 27, 2008, now Pat. No. 8,435,512, application No. 13/646,286, which is a continuation-in-part of application No. 12/501,165, filed on Jul. 10, 2009, and a continuation-in-part of application No. 12/675,220, filed on Feb. 25, 2010, which is a continuation-in-part of application No. PCT/US2008/074489, filed on Aug. 27, 2008, application No. 13/646,286, which is a continuation-in-part of application No. 12/532,740, filed on Sep. 23, 2009, now abandoned, which is a continuation-in-part of application No. PCT/US2008/057468, filed on Mar. 19, 2008, application No. 13/646,286, which is a continuation-in-part of application No. 11/690,334, filed on Mar. 23, 2007, now Pat. No. 8,192,742.

(60) Provisional application No. 61/543,404, filed on Oct. 5, 2011, provisional application No. 61/709,796, filed on Oct. 4, 2012, provisional application No. 61/309,705, filed on Mar. 2, 2010, provisional application No. 61/312,469, filed on Mar. 10, 2010, provisional application No. 61/033,127, filed on Mar. 3, 2008, provisional application No. 61/079,627, filed on Jul. 10, 2008, provisional application No. 60/968,146, filed on Aug. 27, 2007.

(51) Int. Cl.
| | |
|---|---|
| A61K 39/00 | (2006.01) |
| C07K 19/00 | (2006.01) |
| G01N 33/566 | (2006.01) |
| G01N 35/10 | (2006.01) |
| C07K 16/18 | (2006.01) |
| G01N 33/68 | (2006.01) |

(52) U.S. Cl.
CPC ........... C07K 16/18 (2013.01); G01N 33/566 (2013.01); G01N 33/6854 (2013.01); A61K 2039/505 (2013.01); C07K 2317/565 (2013.01); C07K 2317/76 (2013.01); G01N 2333/4716 (2013.01); G01N 2333/96433 (2013.01)

(58) Field of Classification Search
None
See application file for complete search history.

(56) References Cited

U.S. PATENT DOCUMENTS

| | | | |
|---|---|---|---|
| 2003/0198636 A1* | 10/2003 | Gupta-Bansal et al. | ... 424/139.1 |
| 2006/0093599 A1* | 5/2006 | Gazit-Bornstein et al. | ............ 424/133.1 |
| 2006/0292141 A1* | 12/2006 | Holers et al. | ............... 424/144.1 |
| 2010/0263061 A1* | 10/2010 | Song | ................................ 800/3 |

OTHER PUBLICATIONS

Discipio, Richard, "the conversion of human complement component C5 into fragment C5b by the alternative-pathway C5 convertase" Biochem. J., 199, 497-504 (1981).*

* cited by examiner

Primary Examiner — Daniel E Kolker
Assistant Examiner — James Rogers
(74) Attorney, Agent, or Firm — Tarolli, Sundheim, Covell & Tummino LLP

(57) ABSTRACT

A method of selecting a genus of therapeutic antibodies includes selecting antibodies with the following criteria; a) do inhibit cell lysis under conditions wherein the alternative pathway is isolated from the classical pathway; and b) do not inhibit cell lysis under conditions wherein the classical pathway is isolated from the alternative pathway; and c) do not inhibit cell lysis under conditions wherein the classical pathway and alternative pathway are active; and d) do inhibit C3b produced exclusively by the alternative pathway.

2 Claims, 18 Drawing Sheets

ALTERNATIVE PATHWAY SPECIFIC ANTIBODIES FOR TREATING ARTHRITIS

RELATED APPLICATION

This application claims priority from U.S. Provisional Application No. 61/543,404, filed Oct. 5, 2011, 61/709,796, filed Oct. 4, 2012, and is a Continuation-in-Part of PCT/US2011/026,841, filed Mar. 2, 2011, 61/309,705, filed Mar. 2, 2010, PCT/US2011/027,964, filed Mar. 10, 2011, 61/312, 469, filed Oct. 3, 2010, PCT/US2011/027,964, filed Mar. 10, 2011, PCT/US2011/026,841, filed Mar. 2, 2011, 61/309,705, filed Mar. 2, 2011, PCT/US2011/027,964, filed Mar. 10, 2011, Ser. No. 12/920,997, filed Sep. 3, 2010, PCT/US2008/068,530, filed Jun. 27, 2008, 61/033,127, filed Mar. 3, 2008, Ser. No. 12/501,165, filed Jul. 10, 2009, 61/079,627, filed Jul. 10, 2008, Ser. No. 12/675,220, filed Mar. Feb. 25, 2010, PCT/US2008/074,489, filed Aug. 27, 2008, 60/968,146, filed Aug. 27, 2007, Ser. No. 12/532,740, filed Sep. 23, 2009, PCT/US2008/057,468, filed Mar. 19, 2008, Ser. No. 11/690, 334, filed Mar. 23, 2007, the subject matter of which are incorporated herein by reference in their entirety.

GOVERNMENT FUNDING

This invention was made with government support under Grant No, RAG039118 awarded by The National Institutes of Health. The United States government has certain rights to the invention.

BACKGROUND

The complement system in a subject can be activated through three distinct enzymatic cascades, referred to as the "classical pathway", "Lectin/MBL", and "alternative" pathway" (CP, MBL, and AP respectively). The classical pathway is responsible for aiding in host defense against antigens to prevent infection of cells. The lectin pathway is a variation of the classical pathway. The alternative pathway is responsible for 80-95% of total complement activity in cases where trigger of complement activation is the classical pathway ("AP amplification loop"). The alternative pathway by itself is activated in a number of disease indications where complement components have been found in elevated state.

There are three "alternative pathway specific proteins"; Factors B, D, and P, which play a major role in the a) initiation and propagation of the alternative pathway and b) classical pathway propagation via the alternative pathway amplification loop. Proteins C3 and C3b, the key players in complement system, are common to all classical and alternative complement pathways.

The classical pathway (CP) is initiated by antigen-antibody complex. The CP progression involves proteins such as C1Q, C1r/C1s, C4, and C2. The CP C3 convertase consists of C3bC4b2a. This complex can cleave the C3 into C3b and C3a. This C3b is derived from classical pathway convertase and is usually required for opsonization of various pathogens and bacteria. Inhibition of this C3b is undesirable. C3b coated cells are removed via complement receptors present on various cells.

Both complement pathways independently produce C3a, C3b, C5a, C5b, C5b-9, and sC5b-9 as complement activation byproducts.

During classical pathway triggered activation of the alternative pathway, Classical pathway C3 convertase also cleaves C3 into C3b which can work independent of the alternative pathway with full amplification of the classical pathway in 1% normal human serum in the presence of Ca2+/Mg2+ ions. Classical pathway C5 convertase can cleave C5 to generate C5a and C5b. The C5b molecule then inserts into the lipid bilayer of the cell to initiate the formation of C5b-9 or sC5b-9.

In alternative pathway activation, C3b produced by the complement system can bind properdin and Factor B to form the complex "PC3bB". Factor D then cleaves Factor B, within the complex, into Bb and Ba. This cleavage results in the release of Ba from the complex and the formation of the AP convertase PC3bBb. PC3bBb cleaves C3 into C3a and C3b, thereby perpetuating the amplification loop of the alternative pathway for the benefit of the alternative pathway. PC3bBb can then cleave C5 to make C5b and C5a. The C5b molecule then inserts into a lipid bilayer of a cell and forms the nucleus for MAC deposition.

Classical pathway can also initiate the propagation of the alternative pathway known as amplification loop of the classical pathway. Within the amplification loop, C3b binds properdin and Factor B to form the complex "PC3bB". Factor D then cleaves Factor B, within the complex, into Bb and Ba. This cleavage results in the release of Ba from the complex and the formation of the AP convertase PC3bBb. PC3bBb cleaves C3 into C3a and C3b, thereby perpetuating the amplification loop.

As noted above, C3b is therefore both a component and a byproduct of the complement system irrespective of the type of complement pathway activation. During the amplification of the AP, as the PC3bBb (AP C3 Convertase) generates increasing amounts of C3b, an amplification loop is established so that activation of the alternative pathway can continue. Furthermore, the classical pathway can also generate C3b, which can bind factor B and thereby engage the alternative pathway, even though the trigger is CP mediated. This allows more C3b to deposit on a target, which leads to enhanced amplification of AP activation.

Addition of newly formed C3b to the existing AP C3 convertase PC3bBb generates the AP C5 convertase. Addition of newly formed C3b to the existing CP C3 convertase generates CP C5 convertase. Both C5 convertases have the ability to cleave C5 to produce C5b and C5a. The terminal complex produced as a result of complement activation is known as the MAC complex (also known as C5b-9 or sC5b-9), which is responsible for lysis of cells in a subject. Both C3a and C5a are potent anaphylatoxins that are responsible for activating platelets, neutrophils, and monocytes. As a result, inflammatory molecules such as elastase, TNF-α, IL-1, VEGF, and peroxides are released. Formation of C5b-9/sC5b-9 is responsible for tissue damage and tissue injury/tissue damage seen in "other diseases".

Classical complement pathway activation provides a valuable first-line defense against potential pathogens and can generate C3a/C3b, C5a/C5b, and C5b-9/sC5b-9. Therefore, exacerbation of the classical pathway can produce large amounts of complement byproducts. As described elsewhere, both C3a and C5a are potent anaphylatoxins, C3b mediates opsonization, and C5b is responsible for wanted killing of the pathogens. Here, both C3a and C5a would generate beneficial responses and are produced to kill the invaders. This pathway is required for host defense and therefore must not be inhibited.

Alternative pathway activation in Mg++ ions without the calcium ions guarantees only the AP activation. In disease state, this pathway is activated independent of the classical pathway. This pathway is not required for host defense and therefore can be inhibited in its entirety.

It is known that the progression of arthritis or arthritic condition in a subject is mediated by activation of the alternative pathway (Price, Experimental Arthritis: Targeting the Complement Alternative Pathway, Nature Reviews Rheumatology 6, 4 (January 2010)). An "arthritic condition," in this context can include, but is not limited to, rheumatoid arthritis, osteoarthritis, juvenile arthritis, psoriatic arthritis, gouty arthritis, septic arthritis, Lupus, gout, and ankylosing spondylitis.

Rheumatoid arthritis is a chronic inflammatory disorder with an unknown origin that affects the joints on both sides equally in a subject. Osteoarthritis is caused by normal "wear and tear" on the joint. Juvenile arthritis refers to an arthritic condition that develops in subjects under the age of 18. Gout is an acute arthritic condition in which one joint, such as the base of the big toe of a subject, is attacked repeatedly. Septic arthritis is an arthritic condition is the result of an infection caused by a bacteria or fungus. Psoriatic arthritis is an arthritic condition that occurs as a result of psoriasis of the skin of a subject. Ankylosis arthritis is an arthritic condition which causes a joint to harden.

Rheumatoid arthritis is an arthritic condition that can cause inflammation of the joints and of the surrounding tissues of the joint of a subject. Symptoms of rheumatoid arthritis can include, but are not limited to, swelling, pain, and stiffness of a joint. In RA: a) a tissue known as pannus tissue forms over the joint, and causes the joint to lose mobility, b) the synovial membrane of a joint becomes inflamed by the infiltrating leukocytes neutrophils and monocytes, and c), bone erosion, cartilage loss, and bone and tissue damage occurs. Collectively, the joint weakens and losses mobility.

Juvenile idiopathic arthritis (JIA) is characterized by persistent arthritis that begins in a child less than 16 years of age and is present for at least six weeks. Approximately 50% of children with JIA will have arthritic disease as adults. Alternative complement pathway plays a role in JIA based on the clinical study (56 patients) that suggested elevated levels of AP specific protein Bb. These data suggest that AP C3 convertase is elevated.

Osteoarthritis is an arthritic condition that can cause pain and stiffness in a joint of a subject. There are two known types of osteoarthritis. Primary osteoarthritis occurs as a result of aging. As a subject ages, the cartilage in the joint of the subject can degenerate. Secondary osteoarthritis can be caused by several factors including, but not limited to, previous injury to a joint, surgery of a joint, a genetic disorder, obesity, or physical activity. As a result of the degeneration of cartilage in the joint of a subject, the bones of the joint can rub together, causing bone erosion and bone damage. In addition, small bone spurs called osteophytes can form around the area of the joint. Osteophytes can cause pain and limit joint mobility in the subject.

Osteoarthritis can occur in a subject through a variety of repeated stresses and strains on the joint via physical activity. In one example, activities, such as sports or dancing, place additional stresses and strains on the joints, such as the knee, shoulder, wrist, etc. of a subject, which may, over time, lead to an increase of the risk of the subject being diagnosed with arthritic conditions. In another example, laborers, such as electricians, carpenters etc., are at an increased risk of getting arthritic conditions because of repetitive stresses and strains on the joints of the worker, such as the knee, wrist, fingers etc.

Osteoarthritis (OA) is also an inflammation driven arthritis in which the cartilage of the joint, or joints, degenerates with age. Secondary OA refers to OA which is thought to be caused by previous injury to a joint, surgery of a joint, a genetic disorder, obesity, or other repeated physical stresses. As a result of the degeneration of cartilage in the joint, the bones of the joint can begin to rub together, causing bone erosion and bone damage. In addition, small bone spurs called osteophytes can form around the area of the joint. Osteophytes can cause pain and severely limit joint mobility. In those afflicted with OA, complete loss of cartilage can occur very rapidly.

Elevated levels of C3a have been found in arthritis joints. C3a and C5a have potent pro-inflammatory and immunoregulatory functions. They increase vascular permeability and serve as chemo attractants, which that promotes soft tissue swelling. The anaphylatoxins activate neutrophils and monocytes, which results in the production of pro-inflammatory mediators such as TNF-α IL-1, IL-6, IL-8, and IL-17 [47-50]. Of these, TNF-α is the major pro-inflammatory cytokine involved in amplifying and perpetuating inflammation in arthritic joints. C5a is also a potent chemotactic protein that induces neutrophil chemotaxis, de-granulation, neutrophil elastase release, and superoxide generation. Neutrophils contain a potent arsenal of vasoactive, proteolytic and cytotoxic substances, which are produced to mediate many of the manifestations of inflammation in RA. Antibodies inhibit AP induced inflammation and tissue injury.

A number of current treatments target TNF-α. These include infliximab and etanercept. Whereas infliximab is a chimeric anti-TNF-α mAb, etarnercept is a TNF-α receptor fusion protein. In addition to these two, adalimumab (Humira™) binds to TNF-α and inhibits its interaction with cell surface receptors. The success of these drugs show that TNF-α is one of the major destructive elements in RA etiology. Yet, depletion of basal levels of TNF-α is not conducive for protection against serious infections. Selective removal and/or neutralization of only the disease-induced TNF-α should be the objective of future treatments. This is an important area of urgent and unmet medical need and the search for potent and safe therapeutic continues at a fast pace.

Anakinra (Kineret™) and tocilizumab (Actemra™) target the effects of mediators IL-1 and IL-6, respectively. Anakinra competes with IL-1 for the IL-1 receptor thereby providing inhibitory effect. Tocilizumab is a mAb that targets the IL-6 receptor. Other interleukins targeted for anti-RA therapy include IL-17 and IL-8. Experience with infliximab and etanercept (Remicade™ and Enbrel™) show that removal of the total TNF-α is not ideal and should be avoided. Additionally, in terms of drug therapy strategy it would be advisable to inhibit the excess production of inflammatory mediators simultaneously rather than target each mediator individually. For example, rather than seek inhibition of IL-1β, IL-6, or IL-17 individually, it may be more rewarding to prevent excess production of each of these by inhibiting an upstream element, especially that belonging to the AP of the complement. This novel design strategy has been adopted by NovelMed by targeting upstream AP specific proteins that are selective for the alternative complement pathway.

Elevated levels of C3a, C5a, C3b, C5b, and C5b-9 can gauge the level of activation of the complement system in disease conditions. Examples of complement-associated disorders involving the musculoskeletal include, but are not limited to, osteoarthritis [127], osteoporosis [128], acute gouty arthritis [129] (where C6 and MAC are activated), spondyloarthropathy [130], polymyositis [131], dermatomyositis [131, 132] (which increases C3b and C5b-C9), ankylosing spondylitis [133] (associated with increased C3b), general arthritis [10] (where C5a levels rise), enthesitis-related arthritis [134], eosinophilic fasciitis [135], juvenile rheumatoid (idiopathic) arthritis [136] (associated with increased C1q, C4, and MAC), myositis [137] and other forms of arthritis and arthritic conditions. In cases of psoriatic arthritis [138] it has been shown that anti-C5a prevents the arthritis. Inappropriate and/or over-activation of the complement system has also been associated with Reiter's syndrome (reactive arthritis) [139] and relapsing polychondritis [140]. The role of the alternative complement pathway in OA has been recently demonstrated. Elevated levels of C3, C5b-9 and properdin suggest the involvement of the alternative complement pathway.

U.S. Pat. Nos. 6,333,034 and 7,423,128 describe antibodies that inhibit both CP and AP mediated complement activation and therefore host defense is compromised. These antibodies play in role how antibodies prevent the formation of properdin oligomer. Properdin is a thrombospondin type 1 repeat and consists of six repeats of thrombospondin type 1. These antibodies inhibit the binding of properdin to C3b and prevent the formation of C3c. C3b cleavage results in the formation of C3c. Thus these antibodies prevent the cleavage of C3b.

SUMMARY

This application relates to methods for treating a subject suffering from arthritis, an arthritis related, or arthritis-like, condition by administering to an afflicted subject an effective amount of one (or several) of a specific genus of inhibitory antibodies. The antibodies of this genus have been identified and selected, from a variety of antibodies inhibiting the complement system, for their specific and unique effect on specific components of the alternative pathway. The inhibitory antibodies of the selected genus are identified and selected using a specific combination of selection criteria. The antibodies produced from this combination of selection criteria are useful for treating a multitude of arthritic conditions and other diseases.

In some embodiments, the selected antibody can be an anti-C3b antibody (or antibody derived agent) that binds the C3b protein in such a way as to inhibit the formation of AP C3 convertase. This anti-C3b agent, derived from a member of the selected genus of antibodies, specifically binds to human C3b in such a manner as to inhibit the activation of AP without affecting the CP. Despite the fact that C3b is a component of both the classical and the alternative complement pathways, the antibody inhibits the AP but not the CP. An anti-C3b agent includes, but is not limited to, an anti-C3b antibody and antibody variants thereof, antigen-binding fragments thereof, another binding polypeptide, peptide, non-peptide small molecule, aptamer, and DNA and RNA fragment. An anti-C3b agent can bind to C3b and has neutralizing, blocking, partially or fully inhibiting, abrogating, reducing or interfering with C3b functional activities, for example the ability of C3b to participate in the alternative pathway activation in a subject suffering from pathology of arthritis or arthritic conditions.

The AP inhibiting activity of the agent can be evaluated in in vitro, ex vivo and in vivo tests, including, but not limited to, binding assays, alternative pathway hemolysis assays, whole blood inflammation model (tubing loop model) using a relevant animal model, or human clinical trials.

In other embodiments, the selected antibody can be an anti-Ba antibody (or antibody derived agent) that binds the Ba fragment of Factor B, a component specific to the alternative complement pathway. The antibody is a member of the selected genus class of antibodies and therefore, by definition, inhibits the AP but not the CP. An anti-Ba agent includes, but not limited to, an anti-Ba antibody and antibody variant thereof, antigen-binding fragment thereof, another binding polypeptide, peptide, non-peptide small molecule, aptamer, and DNA and RNA fragment. An anti-Ba agent can bind to Ba and has the effect of neutralizing, blocking, partially or fully inhibiting, abrogating, reducing or interfering with Ba functional activity. For example, the agent inhibits the ability of Ba to participate in alternative pathway activation in a subject suffering from arthritis or arthritic conditions.

The anti-Ba agent can have the ability to inhibit only AP dependent biological activity of Ba. The AP activity of the agent can be evaluated in in vitro, ex vivo and in vivo tests, including, but not limited to, binding assays, alternative pathway hemolysis assays, whole blood inflammation model (tubing loop model) using a relevant animal model, or human clinical trials.

In still other embodiments, the selected antibody can be an anti-Bb antibody (or antibody derived agent) that binds the Bb fragment of Factor B, a component specific to the alternative complement pathway. The antibody is a member of the selected genus class of antibodies and therefore, by definition, inhibits the AP but not the CP. An anti-Bb agent includes, but not limited to, an anti-Bb antibody and antibody variant thereof, antigen-binding fragment thereof, another binding polypeptide, peptide, non-peptide small molecule, aptamer, and DNA and RNA fragment. An anti-Bb agent can bind to Bb and has the effect of neutralizing, blocking, partially or fully inhibiting, abrogating, reducing or interfering with Bb functional activity. For example, the agent inhibits the ability of Ba to participate in alternative pathway activation in a subject suffering from arthritis or arthritic conditions.

The anti-Bb agent of the present invention can have the ability to inhibit only AP dependent biological activity of Bb. The AP activity of the agent can be evaluated in in vitro, ex vivo and in vivo tests, including, but not limited to, binding assays, alternative pathway hemolysis assays, whole blood inflammation model (tubing loop model) using a relevant animal model, or human clinical trials.

In still other embodiments, the selected antibody can be an anti-P antibody (or antibody derived agent) that binds Properdin (P), a component specific to the alternative complement pathway. The antibody is a member of the selected genus class of antibodies and therefore, by definition, inhibits the AP but not the CP. An anti-P agent includes, but not limited to, an anti-P antibody and antibody variant thereof, antigen-binding fragment thereof, another binding polypeptide, peptide, non-peptide small molecule, aptamer, and DNA and RNA fragment. An anti-P agent can bind to P and has the effect of neutralizing, blocking, partially or fully inhibiting, abrogating, reducing or interfering with P functional activity in such a way as to inhibit only the AP. For example, the agent inhibits the ability of P to participate in alternative pathway activation in a subject suffering from arthritis or arthritic conditions.

The anti-P agent of the present invention can have the ability to inhibit only AP dependent biological activity of P. The AP activity of the agent can be evaluated in in vitro, ex vivo and in vivo tests, including, but not limited to, binding assays, alternative pathway hemolysis assays, whole blood inflammation model (tubing loop model) using a relevant animal model, or human clinical trials.

DETAILED DESCRIPTION

Definitions

Figure 1:
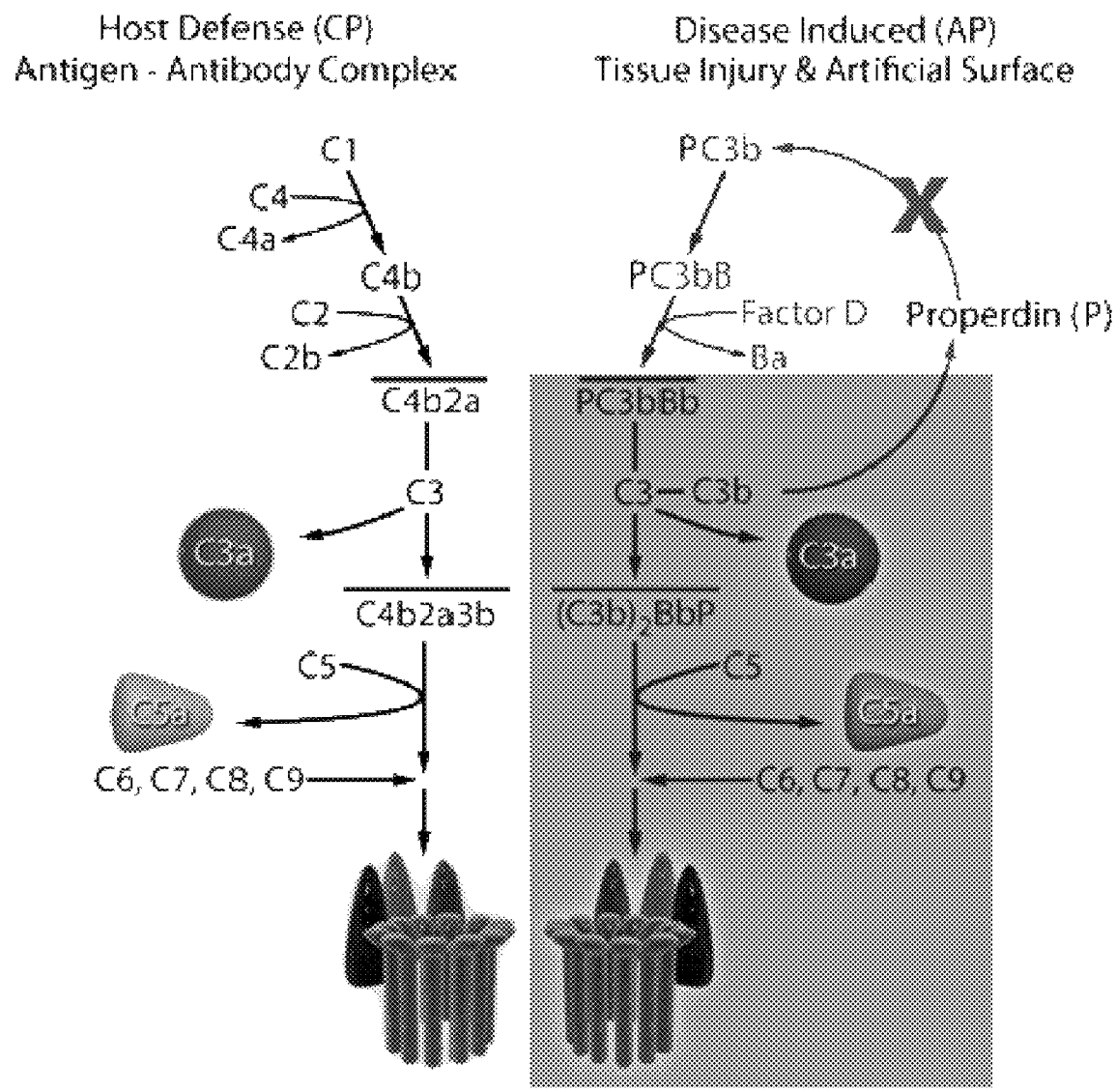
FIG. 1 is a schematic illustration showing the complement cascade of the classical pathway and the alternative pathway. Lectin pathway is not shown as it is not the part of the invention.

Unless specifically defined herein, all terms used in this document have the same meaning as would be understood by those of ordinary skill in the art. The following definitions are provided for clarity, and to define their intended meaning as used in the specification and claims.

Complement Pathways

"CLASSICAL PATHWAY" refers to complement which is triggered by antigen-antibody complexes and requires C1Q for activation and may or may not also trigger the alternative pathway amplification loop for its propagation.

"ALTERNATIVE PATHWAY" refers to complement activation which is triggered by a cell surface (or cell-surface like material). Such a surface could be, for example, zymosan from fungal, yeast cell walls, or a lipopolysaccharide (LPS) from Gram negative outer membranes. The alternative pathway can be triggered by rabbit erythrocytes, viruses, bacteria, animal tumor cells, parasites, and/or damaged cells. The alternative pathway may also begin with spontaneous proteolytic generation of C3b from complement factor C3, where C3b has the ability to bind B and P both.

"alternative pathway specific protein" refers to C3b, factor B, factor Bb, factor D, and/or properdin.

"AP AMPLIFICATION LOOP" refers to a looping series of reactions in which C3b formed makes AP C3 convertase. This convertase cleaves C3 and generates more C3b, which feeds back into the loop. This self-perpetuating cycle of reactions generates large amounts of C3b.

"COMPONENT OF THE ALTERNATIVE COMPLEMENT PATHWAY" refers to a group of proteins which make up the AP. These are properdin, Factor B, Factor Ba, Factor Bb, Factor D, C3, C3a, C3b, AP C3 convertase, AP C5 convertase, and all cleavage products and isoforms thereof.

"AP ACTIVATED" describes alternative pathway activation via a set of surfaces, including those found on dead tissue, genetically modified tissue, bacteria, damaged tissue and surfaces that are considered foreign to human body. This definition may be taken to imply that AP activation is not mediated via the classical pathway. AP activated whole blood defines that alternative pathway is activated in whole blood similar to which is present in vivo and complement activation is mediated via the alternative pathway.

"ALTERNATIVE PATHWAY-DEPENDENT" describes the characteristic of a process, production, protein or other agent or phenomenon that results exclusively from activity of the alternative pathway of the complement system. For example, "AP-dependent complement activation" refers to an activation of the complement system which is mediated by the alternative pathway, independent of the classical pathway.

"ALTERNATIVE PATHWAY-DEPENDENT C3a" describes the formation of C3a produced from activity of the alternative pathway of the complement system in whole blood. For example, "AP-dependent C3a formation" refers to the formation of C3a via activation of the alternative pathway, which is independent of the classical pathway.

"aC3b" is custom term used exclusively for this application and is not a generally acknowledged abbreviation for a C3 split product. aC3b refers to the C3b derived from the alternative pathway, cC3b refers to the C3b produced by the activation of the classical pathway "ALTERNATIVE PATHWAY-DEPENDENT C5a" describes the formation of C5a produced from activity of the alternative pathway of the complement system in whole blood. For example, "AP-dependent C5a formation" refers to the formation of C5a via activation of the alternative pathway, which is independent of the classical pathway.

"ALTERNATIVE PATHWAY-DEPENDENT sC5b-9" describes the formation of sC5b-9 produced from activity of the alternative pathway of the complement system. For example, "AP-dependent sC5b-9 (soluble MAC) formation" refers to the formation of sC5b-9 via activation of the alternative pathway, which is independent of the classical pathway.

"ALTERNATIVE PATHWAY-DEPENDENT C5b-9" describes the formation of C5b-9 produced from activity of the alternative pathway of the complement system. For example, "AP-dependent C5b-9 formation (Deposited MAC)" refers to the formation of dC5b-9 via activation of the alternative pathway, which is independent of the classical pathway.

"C3a DEPENDENT CELLULAR ACTIVATION" describes the activation of neutrophils, monocytes, platelets, T lymphocytes, endothelial cells, mast cells, and platelets which occurs when Alternative Pathway-Dependent C3a binds to C3a receptors, which are present on these cells. These cells are found, in their C3a activated state, in various different diseases (see OTHER DISEASES).

"C5a DEPENDENT CELLULAR ACTIVATION" describes the activation of neutrophils, monocytes, platelets, T lymphocytes, endothelial cells, mast cells, and platelets which occurs when Alternative Pathway-Dependent C5a binds to C5a receptors, which are present on these cells. These cells are found, in their C5a activated state, in various different diseases (see "OTHER DISEASES").

"C5b-9 and sC5b-9 DEPENDENT TISSUE INJURY/ CELLULAR DAMAGE" describes the cellular damage caused by the formation of sC5b-9 and/or C5b-9. These molecules either bind to the cellular surface and/or insert themselves into the cell's plasma membrane resulting in pathological conditions also described as "TISSUE INJURY". Tissue injury occurs in various diseases and can result in the damage to various organs (see "ALL ORGANS").

"MEMBRANE ATTACK COMPLEX" ("MAC") refers to a complex of the terminal five complement components (C5b-C9) that inserts into and disrupts cell membranes. This complex is also referred to as C5b-9. MAC complex is produced by both the alternative pathway and by the classical complement pathway. The complex that is associated with "S protein" is called sC5b-9, a soluble form of MAC. The selected antibodies inhibit alternative pathway associated C5b-9 and sC5b-9.

"C3a, C5a, C5b-9, sC5b-9 AND INFLAMMATION" describes inflammation caused by the products of AP activation and activity; and in particular, the AP products C3a, C5a, C5b-9, and sC5b-9 generating from AP activity. These molecules cause C3a DEPENDENT CELLULAR ACTIVATION, C5a DEPENDENT CELLULAR ACTIVATION, C5b-9 and sC5b-9 DEPENDENT CELLULAR DAMAGE, and result in the prevalence of CYTOKINE ACTIVATED CELLS, PROTEASE ACTIVATED CELLS, and PEROXIDE ACTIVATED CELLS, all of which can be implemented in various different diseases and disease pathologies.

Whole Blood & Inflammation

"WHOLE BLOOD" describes complete blood with the same composition of cells, chemicals, proteins, etc. as blood found in human blood vessels. The isolated blood contains all components of the complement system including inflammatory cells that are responsible for inflammatory responses.

"INFLAMMATION IN WHOLE BLOOD" describes the cascade of reactions beginning with alternative pathway activation in whole blood, the resulting production of C3a, C5a, and C5b-9 and sC5b-9 in whole blood, the resulting activation of neutrophils monocytes and platelets in whole blood, and ultimately, the production of inflammatory cytokines in whole blood (in vivo or ex vivo).

"CYTOKINE MEDIATED INFLAMMATION" describes the role of cytokines in the instigation and propagation of inflammation that is associated with a variety of disorders wherein inflammation is central to the disease condition. Cytokines, including TNF-α and IL-1 cause degradation of tissue, cartilage, and bone. Cytokines are present in blood. They are released from activated monocytes which are also in blood. Activated monocytes (and activated neutrophils) have a higher level of CD11b. CD11b is a marker that defines and indicates cellular action (and cell activation). There are many diseases and other pathologies associated with elevated levels of activated neutrophils, activated monocytes, activated T-lymphocytes, activated basophils, and/or activated mast cells.

"CYTOKINE ACTIVATED CELLS" describes cells which have been activated via cytokine byproducts arising from alternative complement pathway activity. The relevant cytokines are those that generate inflammation, and inflammatory response, in whole blood. This inflammation, and inflammatory response, can ultimately damage cells. These cytokines include, but are not limited to, TNF-α, IL-1, IL-8, and IL-17.

"PROTEASE ACTIVATED CELLS" describes cells which have been activated via protease byproducts arising from alternative complement pathway activity. The relevant proteases are those that degrade the extracellular matrix, as well as bone, cartilage and several other tissues. These proteases include, but not limited to, neutrophils elastase and metallo-proteases.

"PEROXIDE ACTIVATED CELLS" describes cells which have been activated via peroxide byproducts arising from alternative complement pathway activity. These peroxides cause oxidative damage to cells, tissues, and organs in the areas that are in contact with the blood or in the blood itself.

Arthritis & Other Diseases

"ALTERNATIVE PATHWAY (AP)-DEPENDENT INFLAMMATION IN OTHER DISEASES" refers to an increase in alternative complement pathway activity, as measured by continued or increased formation, and/or release, of one of the following components C3a, C3b, C5a, C5b-9, or sC5b-9, and all the anticipated consequences thereof in "other diseases". Such anticipated consequences include; continued or increased AP-dependent MAC-mediated deposition or lysis of cells, continued or increased AP-dependent activation of platelets, monocytes, neutrophils, mast cells, or basophils; and/or continued or increased AP-dependent formation or release of TNF-α, IL-1, or neutrophil elastase.

"OTHER DISEASES" describes a list of diseases where one of the components measured is derived from the activation of the complement system, these components include but not limited to C3, P, B, P, C5b-9, sC5b-9. This category includes diseases where elevated levels of complement byproducts have been found in blood and or tissues, where elevated levels of complement receptors have been found associated with the various tissues and organs. See pages 39 through 44 for examples of such diseases. Examples of such diseases are as given below. Elevated levels of complement activation products are associated with the disease as production of anaphylatoxins C3a and C5a are responsible for cellular activation and release of inflammatory mediators and ultimate tissue damage in disease.

As used herein, the terms "ALLEVIATE," "ALLEVIATED," and the like refer to either (1) making symptoms of an inflammatory disease or disorder, an autoimmune disease, or joint instability more bearable for the subject or (2) partially healing the symptoms of an inflammatory disease or disorder, an autoimmune disease, or joint instability.

"ALTERNATIVE PATHWAY (AP)-DEPENDENT INFLAMMATION IN ARTHRITIS" refers to an increase in alternative complement pathway activity, as measured by continued or increased formation, and/or release, of C3a, C3b, C5a, C5b-9, or sC5b-9, and all the anticipated consequences thereof. Such anticipated consequences include; continued or increased AP-dependent MAC-mediated deposition or lysis of cells, continued or increased AP-dependent activation of platelets, monocytes, neutrophils, mast cells, or basophils; and/or continued or increased AP-dependent formation or release of TNF-α, IL-1, or neutrophil elastase.

"AUTOIMMUNE DISEASE" refers to a condition where the immune response of a subject is inappropriately directed against substances and tissues normally present in the body.

"CELLULAR LYSIS" indicates tissue injury in part. Cellular lysis occurs as a result of C5b-9 formation of the cell surface. Such deposition of C5b-9 leads to cellular injury and in case of tissues the cell injury is a tissue injury.

Inhibitory Antibodies and Agents

"COMPLEMENT CASCADE INHIBITORY AGENT," when used herein, refers to a compound or composition which inhibits complement cascade progression. Examples of such include agents that block the interaction of properdin to C3b or C3bB.

"AGENT" or "COMPOUND" refers to any substance, molecule, element, compound, entity, or any combination thereof. An agent can be, among other things, a protein, oligopeptide, small organic molecule, polysaccharide, polynucleotide, or other biochemical substance. It can be a natural product, a synthetic compound, a chemical compound, or a combination of two or more substances of different origins. Unless otherwise specified, the terms "agent", "substance", and "compound" can be used interchangeably.

"ALTERNATIVE PATHWAY SPECIFIC ANTIBODY" refers to an antibody or fragment thereof that can bind to an alternative pathway protein to inhibit activation and/or progression of the alternative pathway in a subject.

"SPECIFICALLY BINDS" refers to the action of an agent to bind to another agent in a specific and unique way, particularly in the presence of a heterogeneous population of molecules. For example, an anti-properdin antibody has inherent binding specificity for properdin.

"SELECTIVELY INHIBITS THE ALTERNATIVE COMPLEMENT PATHWAY" refers to the preferential and exclusive inhibition of the alternative complement pathway. An agent acting in such a way does not effect the activation of the classical pathway or any other activity of the remainder of the complement system, including the progression and activity of the classical pathway.

"ANTIBODIES TO AP PROTEINS" describe anti-P, anti-Ba, anti-Bb, anti-C3b antibodies that neutralize the activity of the alternative pathway without inhibiting the classical pathway.

Pharmacology

"PHARMACOKINETIC ACTIVITY" or "PHARMACOKINETICS" refers to the mechanisms of absorption and distribution of an administered drug, the rate at which a drug action begins and the duration of the effect, the chemical changes of the substance in the body, and the effects and routes of excretion of the metabolites of the drug "THERAPEUTICALLY EFFECTIVE AMOUNT" is defined as an amount sufficient to treat the symptoms of a disease or disorder in a subject.

As used herein, a "prophylactically effective amount" is defined as an amount sufficient to prevent the onset of a disease or disorder in a subject. As used herein, the terms "administering," "administration," and like refer to ways in which the antibody or antigen binding fragment thereof can be given to the subject, including, but not limited to, oral administration, intravenous administration, subcutaneous administration, aural administration, or rectal administration.

Product by Process

"ASSAY-1, ASSAY-2, ASSAY-3" describe assays to establish the antibody genus. This means collection of antibodies that share the same process of selection.

Assay-1 (conducted in 1% human serum) only initiates the classical pathway, despite the fact that ionic conditions of the alternative pathway activation exist within the buffer system. In Assay-1 there is no participation of the alternative pathway.

Assay-2 is conducted in 10% human serum under conditions with sufficient (Ca2+/Mg2+) for both classical pathway and alternative pathways are activity.

Assay-3 is conducted in 10% human serum under conditions with only sufficient (Mg++) allowing for only the alternative pathway activation.

"ANTIGEN" refers to a substance that stimulates the production of an antibody in a subject. Antigens can include, but are not limited to, toxins, bacteria, or foreign blood cells.

"A SUBJECT" or "A PATIENT" include all mammals, including without limitation humans, non-human primates, dogs, cats, horses, sheep, goats, cows, rabbits, pigs and rodents.

Antibodies

"ANTIBODY" is used in the broadest sense and includes monoclonal antibodies, including full length or partial length monoclonal antibodies, and polyclonal antibodies from mouse, rabbit or human species. In its most widely recognized form, an antibody contains two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hyper-variability, termed complementarity determining regions (CDRs), interspersed with regions that are more conserved, termed framework regions (FR). Each VH and VL is composed of three CDRs and four Frameworks arranged from amino-terminus to carboxyl-terminus in the following order: FR1, CDR1, FR2, CDR2, FR3, CDR3, FR4. The variable regions of the heavy and light chains contain a binding domain that interacts with an antigen. The term "antibody" encompasses whole antibodies and antibody fragments thereof, derived from any antibody-producing mammal (e.g., mouse, rat, rabbit, and primate including human), that specifically bind to proteins such as properdin, C3b, Ba, and Bb or portions thereof. Exemplary antibodies include polyclonal, monoclonal and recombinant antibodies; multi-specific antibodies (e.g., bispecific antibodies); humanized antibodies; murine antibodies; chimeric, mouse-human, mouse-primate, primate-human monoclonal antibodies; and anti-idiotype antibodies, and may be any intact molecule or fragment thereof.

"OTHER ANTIBODIES" refer to antibodies developed in living organism including and not limited to animals and humans for therapeutic use in humans and animals. Any antibodies raised in a living organism is capable of inhibiting AP mediated lysis (Assay-3) but not the CP mediated lysis or the CP amplification loop.

"ANTIBODY FRAGMENT" refers to a portion derived from or related to a full-length antibody, particularly an anti-C3b, anti-P, and anti-Ba, or anti-Bb antibody, generally including the antigen binding or variable region thereof (see "ANTIGEN BINDING FRAGMENT"). The term "antibody fragment" refers to a portion derived from a full-length alternative pathway specific antibody, generally including the antigen binding and variable region thereof. Other antibodies include diabodies, linear antibodies, single-chain antibody molecules and multispecific antibodies formed from antibody fragments. Examples of antibody fragments include Fab, Fab', F(ab)2, F(ab')2 and Fv fragments, or scFv fragments.

"ANTIGEN BINDING FRAGMENT" of an antibody refers to the one or more fragments of an intact antibody that retain the ability to specifically bind to a given antigen. Antigen binding functions of an antibody can be performed by fragments of an intact antibody containing the Complementarity Determining Regions (CDRs). Examples of antigen binding fragments: "Fab" fragments (single chain variable regions with VH and VL); "Monovalent Fragments" (antibody fragments consisting of the VL, VH, CL and CH1 domains); "F(ab')2" fragments (bivalent fragments comprising two Fab fragments linked by a disulfide bridge at the hinge region); "Fd" fragments (which consist of the VH and CH1 domains of an antibody); "Fv" fragment (which consist of the VL and VH domains of a single arm of an antibody); single domain antibody ("dAb"), which consist of a VH domain or a VL domain; and an isolated Complementarity Determining Region ("CDR").

A "FUNCTIONAL DERIVATIVE" of an antibody is any compound which is either taken from, or incorporates within itself, the functional region of the antibody. Functional derivatives of antibodies include, but are not limited to, antigen binding fragments, CDRs, humanized antibodies, "Fab" fragments, "Fd" fragments, chimeric antibodies, monoclonal antibodies, recombinant antibodies, and single chain antibodies.

CDRs, as antigen binding fragments, can also be incorporated into single domain antibodies, maxi bodies, mini bodies, intrabodies, diabodies, triabodies, tetra bodies, v-NAR and bis-scFv. Antigen binding fragments of antibodies can be grafted into scaffolds based on polypeptides such as Fibronectin type III (Fn3). Antigen binding fragments can be incorporated into single chain molecules comprising a pair of tandem Fv segments (VH-CH1-VH-CH1) which, together with complementary light chain polypeptides, form a pair of antigen binding regions.

"FC REGION" refers to the region of the antibody that induces effector functions.

"AFFINITY" refers to the chemical strength of the interaction between an antibody and an antigen at single antigenic sites.

"BINDING SPECIFICITY" refers to the ability of an individual antibody or antigen binding fragment to bind to a particular target, e.g., the binding specificity of an anti-properdin antibody to bind only to properdin.

"COMPOUNDS," "BLOCKER", "INHIBITOR", or "ANTAGONIST" refers to a chemical substance, or force, that retards or prevents a chemical or physiological reaction or response. Common blockers or inhibitors include, but are not limited to, antisense molecules, antibodies, antagonists and their derivatives. For example, an antibody that binds to a component of an AP specific interaction between that component and another component of the AP. Such an antibody would be an inhibitor or blocker of that interaction and, by extension, the AP.

"CHIMERIC ANTIBODY" is a recombinant protein that contains the variable domains and CDRs derived from an antibody of from a non-human species of animal, while the remainder of the antibody molecule is derived from a human antibody. The replacement of the non-binding region of the antibody with a human constant region enables the chimeric antibody to retain its specificity in recognizing and binding the targeted antigen while having reduced antigenicity in humans (compared to the original mouse antibody).

"HUMANIZED ANTIBODY" is a chimeric antibody that consists of non-human CDRs and humanized framework regions. Humanized antibodies are typically recombinant proteins in which only the antibody complementarity-determining regions are of non-human origin.

"SINGLE-CHAIN FV" or "SCFV" antibody fragment comprises the VH and VL domains of an antibody, wherein these domains are present in a single polypeptide chain.

"IMMUNOGENICITY" refers to the ability of an antigen to initiate an immune response in a subject.

"COMPLEMENTARITY DETERMINING REGIONS (CDRs)" are the key binding regions of the antibody. There are typically three CDRs found within the variable regions of each of the two heavy and light chain variable regions. CDRs can be shuffled around, in terms of location, to create a particular binding affinity. See also "ANTIGEN BINDING FRAGMENTS."

"EFFECTOR FUNCTIONS" refer to those biological activities attributable to the native Fc region of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); lack of activation of platelets that express Fc receptor; and B cell activation. In order to minimize or eliminate side effects of a therapeutic antibody, it may be preferable to minimize or eliminate effector functions.

As used herein, the term "reduced Fc effector function(s)" refers to the function(s) of an antibody wherein the antibody does not act against an antigen that recognizes the Fc region of the antibody. Examples of reduced Fc effector functions can include, but are not limited to, reduced Fc binding to the antigen, lack of Fc activation against an antigen, an Fc region that contains mutations to prevent normal Fc effector functions, or prevention of the activation of platelets and other cells that have Fc receptors.

"HUMAN ANTIBODY" is an antibody in which all components of the antibody are of human origin, including the framework, CDRs, and constant regions. The term "humanized" antibody is an antibody of non-human origin that retains the binding specificity of the non-human antibody while being less immunogenic in humans. See CHIMERIC ANTIBODY and HUMANIZED ANTIBODY.

"ISOLATED ANTIBODY" refers to an antibody which has been identified and separated and/or recovered from a component or components of its natural environment. Contaminant components of an antibody's natural environment are materials which would interfere with diagnostic or therapeutic uses for the antibody, and may include enzymes, hormones, and other proteinaceous or non-proteinaceous solutes. Isolated antibody includes the antibody in situ within recombinant cells since at least one component of the antibody's natural environment will not be present. Ordinarily, however, isolated antibody will be prepared by at least one purification step.

"PURIFIED ANTIBODY" refers to antibodies which have been isolated from contaminants. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue, or preferably, silver stain.

"ISOTYPE" refers to the antibody class (e.g., IgM, IgE, IgG such as IgG1 or IgG4) that is provided by the heavy chain constant region genes. Isotype also includes modified versions of one of these classes, where modifications have been made to alter the Fc function, for example, to enhance or reduce effector functions or binding to Fc receptors.

"MONOCLONAL ANTIBODY" refers to an antibody obtained from a population of substantially homogeneous antibodies, i.e., the individual antibodies comprising the population are identical. A monoclonal antibody is directed against a single determinant on the antigen. For example, the monoclonal antibodies useful in the present invention may be prepared by the hybridoma methodology or they may be made using recombinant DNA methods in bacterial or eukaryotic animal or plant cells. The "monoclonal antibodies" may also be isolated from phage antibody libraries, or generated using in vitro, in vivo, and cell culture methods. Monoclonal antibodies include those that bind to a unique sequence of amino acids and have a single specific epitope on its target antigen.

"POLYCLONAL ANTIBODY PREPARATIONS," unlike monoclonal antibody preparations, include different antibodies directed against different determinants (epitopes). As used herein, the term "polyclonal" refers to an antibody that recognizes multiple epitope sites on a single antigen.

"EPITOPE" includes any protein determinant capable of specific binding to an immunoglobulin. Epitope determinants usually consist of chemically active surface groupings of molecules such as amino acids or sugar side chains and usually have specific three-dimensional structural characteristics, as well as specific charge characteristics.

"AGLYCOSYLATED" refers to an antibody with a hydroxyl or other functional group that is not attached to a glycosylate group.

"RECOMBINANT ANTIBODY" includes all antibodies that are prepared, expressed, created or isolated by recombinant means and methods.

"SINGLE CHAIN ANTIBODY" refers to an antibody in which the two domains of the Fv fragment, VL and VH, are coded for by separate genes. These genes can be joined, using recombinant methods, by an artificial peptide linker. Joining the genes results in the production of a single protein chain in which the VL and VH regions pair to form monovalent molecules (known as single chain Fv, "scFv"). Such single chain antibodies include one or more "antigen binding fragments" of an antibody. See ANTIGEN BINDING FRAGMENT.

"THERAPEUTIC ANTIBODY" refers to an antibody that may be considered effective in a therapeutic or prophylactic context with regard to a disease or condition of interest.

"AMINO ACID," in the broadest sense, refers to the naturally occurring amino acids which can be divided into groups based upon the chemical characteristic of the side chain of the respective amino acids. "Hydrophobic" amino acids are Ile, Leu, Met, Phe, Trp, Tyr, Val, Ala, Cys and Pro. "Hydrophilic" amino acids are, Asn, Gln, Ser, Thr, Asp, Glu, Lys, Arg and His. The "uncharged hydrophilic" amino acids are Ser, Thr, Asn and Gln. The "acidic" amino acids are Glu and Asp. The "basic" amino acids are Lys, Arg and His. As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

"CONSERVATIVE AMINO ACID SUBSTITUTION" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine.

"IDENTICAL," in the context of two or more nucleic acids or polypeptide sequences, refer to two or more sequences or subsequences that are the same. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length. The percent identity between two amino acid sequences can also be determined using the algorithm of Meyers and Miller.

Arthritis

"INFLAMMATORY DISORDER OR DISEASE" refers to any disorder or disease in which inflammation plays a role. Examples of an inflammatory disorder or disease can include, but are not limited to, arthritis, rheumatoid arthritis, osteoarthritis, juvenile arthritis, psoriatic arthritis, gouty arthritis, ankylosing spondylitis, systemic lupus erythematosus, mixed connective tissue disease, or sepsis.

"ARTHRITIS" comprises diseases and conditions characterized by pain, stiffness, inflammation, and/or damage to joint cartilage and surrounding structures. The pathology associated with arthritis may include excessive activation of macrophages, synoviocytes, neutrophils, T lymphocytes and the associated increases in production of endogenous pro-inflammatory mediators including cytokines, chemokines, complement proteins, and/or reactive free radicals. The pathology may also include leukocyte infiltration into joint (and joint surrounding) tissues, destruction of collagen, erosive bone damage, abnormal growth and division of synovium cells, joint effusion, synovial hyperplasia, synovial pannus, invasion of abnormal synovial cells into cartilage and bone, weakening of muscles, ligaments and tendons in joints, bone loss, cartilage depletion, pain, swelling, stiffness, fatigue, and loss of joint range of motion, reduction in red blood cells, and/or inflammation of the blood vessels. The invention also considers marked growth of synovial cells, formation of a multilayer structure due to abnormal growth of the synovial cells (pannus formation), invasion of the synovial cells into cartilage tissue and bone tissue, vascularization toward the synovial tissue, and/or infiltration of inflammatory cells such as lymphocytes, synoviocytes and/or macrophages. A patient is typically diagnosed with arthritis based on clinical symptoms. However, there are some diagnostic tests which may be utilized. These include, without limitation, tests for: erythrocyte sedimentation rate, C-reactive protein, rheumatoid factor, X-rays, arthroscopy, joint aspiration, anti-CCP antibodies, interleukin-6, interleukin-3, and/or timp-1.

"EXACERBATION OF ARTHRITIS" refers to an increase in the swelling, pain, inflammation, pannus formation, loss of cartilage and bone and decreased mobility.

"DAMPENING OF ARTHRITIS" refers to a decrease in the physical symptoms of the disease as those observed with use of an effective treatment.

"ARTHRITIS-RELATED AUTOIMMUNE DISORDER" is a disease or disorder that is associated with arthritis or an arthritic condition in which the immune system inappropriately attacks and destroys body tissue in or near the joint.

"JUVENILE IDIOPATHIC ARTHRITIS" (JIA) refers to diseases where a child of 16 years of age or less has arthritis in one or more joints for at least six weeks. The term "JIA" has largely replaced "juvenile rheumatoid arthritis."

"OSTEOARTHRITIS" (OA), also referred to as degenerative joint disease, refers to the degradation and breakdown of cartilage in joints resulting in pain, swelling, and loss of motion of the joint. It commonly occurs in the hips, knees, and spine and often affects the finger joints, the joint at the base of the thumb, and the joint at the base of the big toe. The disease is particularly common among older people. In the clinic, osteoarthritis is generally assessed based on the patient's description of symptoms, the location and pattern of the pain, and certain findings upon physical examination. Radiological methods such as x-rays of affected joints and application of The Western Ontario and McMaster Universities Osteoarthritis Index ("WOMAC") can be used to diagnose the disease (see for example Osteoarthritis, National Institute of Arthritis and Musculoskeletal and Skin Diseases, National Institutes of Health, NIH Publication No. 06-4617, May 2006).

"EARLY STAGE OA" is characterized by episodic joint pain. The term "late stage OA" is characterized by tender joints, joint deformity, a loss of mobility and new bone formation (osteophytes). Passive joint movement during examination may elicit crepitus or the grinding of bone-on-bone as the joint moves. X-rays may reveal damage within the joint space and misalignment of the joint.

"RHEUMATOID ARTHRITIS" (RA) refers to an autoimmune inflammatory disease that causes pain, swelling, stiffness, and loss of function in the joints. RA generally occurs in a symmetrical pattern. The disease often affects the wrist joints and the finger joints closest to the hand, but it can also affect other parts of the body.

"PANNUS TISSUE" refers to an abnormal layer of tissue that forms in a joint of a subject as a result of rheumatoid arthritis.

"OSTEOPHYTE" refers to an extraneous bony piece of tissue that forms around a joint.

"ACUTE JOINT DAMAGE" or "ACUTE JOINT INFLAMMATION" refers to joint damage or inflammation that lasts for shorter than three months or initiates quickly in a subject.

"CHRONIC JOINT DAMAGE" or "CHRONIC JOINT INFLAMMATION" refers to joint damage or inflammation that lasts for longer than three months in a subject.

Treatment

"TREATMENT," "TREATING," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease or at risk of acquiring the disease but has not yet been diagnosed as having it; (b) inhibiting the disease, i.e., arresting its development; and (c) relieving the disease, i.e., causing regression of the disease.

"TREATMENT" can also refer to an intervention performed with the intention of preventing the development or altering the pathology of a disorder. Accordingly, "treatment" refers to both therapeutic treatment and prophylactic or preventative measures, wherein the object is to prevent or slow down the progression of or lessen the severity of the targeted pathological condition or disorder. Those in need of treatment include those already with the disorder as well as those in which the disorder is to be prevented. "TREATMENT" includes rendering the disease more susceptible to treatment by other therapeutic agents.

"COMBINATION THERAPIES": In numerous embodiments, a properdin trap may be administered in combination with one or more additional compounds or therapies, including a second properdin trap molecule and/or a secondary C3b trap molecule. Combination therapy includes administration of a single pharmaceutical dosage formulation which contains a properdin trap and one or more additional agents; as well as administration of a properdin trap and one or more additional agent(s) in its own separate pharmaceutical dosage formulation.

DE-IMMUNIZED" refers to a moiety that has been modified in such a way as to make it more likely to be recognized as self by a subject's immune system. For example, a non-human antibody with potential therapeutic use in a human may be de-immunized by replacing some, or all, of its non-human amino acid sequences with human sequences. By substituting human amino acid sequences for non-human sequences, the human subject's immune system is less likely to recognize the antibody as foreign or non-self.

"EFFECTIVE AMOUNT" is the minimum amount, or lowest concentration, of a compound which has the effect of causing or enabling either a detectable improvement or measurable degree of protection in a subject afflicted with arthritis or an arthritic condition.

"INTRAVENOUS INFUSION" refers to the introduction of a drug into the vein of an animal or human patient over a period of time greater than approximately 5 minutes, preferably between approximately 30 to 90 minutes, although, according to the invention, intravenous infusion is alternatively administered for 5 hours or less.

"PROPERDIN TRAP ANTAGONIST" is a receptor-Fc fusion protein consisting of the principal ligand-binding portions of the human properdin Fab fused to the Fc portion of human IgG1. In a preferred embodiment, an expression plasmid encoding properdin is transfected into CHO cells, which secrete properdin trap into the culture medium. The resulting properdin trap binds its ligands using the binding domains of high-affinity receptors, having greater affinity for properdin.

"RECOMBINANT HOST CELL" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

"SUBCUTANEOUS ADMINISTRATION" refers to introduction of a drug under the skin of an animal or human patient, preferable within a pocket between the skin and underlying tissue, by relatively slow, sustained delivery from a drug receptacle. The pocket may be created by pinching or drawing the skin up and away from underlying tissue.

"THERAPEUTICALLY EFFECTIVE DOSE" is a dose used for the purpose of the treatment, and will be ascertainable by one skilled in the art using known techniques. Efficacy can be measured in conventional ways, depending on the condition to be treated. For acute and chronic therapy, efficacy can, for example, be measured by assessing the time to disease progression, or determining the response rates. Therapeutically effective amount also refers to a target serum concentration, such as a trough serum concentration, that has been shown to be effective in suppressing disease symptoms when maintained for a period of time. For systemic administration, a "therapeutically effective dose" can be estimated initially from in vitro assays. For example, a dose can be formulated in animal models to achieve a circulating concentration range that includes the IC50 as determined in cell culture. Such information can be used to more accurately determine useful doses in humans. Initial dosages can also be estimated from in vivo data, e.g., animal models, using techniques that are well known in the art. One having ordinary skill in the art could readily optimize administration to humans based on animal data. Dosage amount and interval may be adjusted individually to provide plasma levels of the compounds that are sufficient to maintain therapeutic effect. One having skill in the art will be able to optimize therapeutically effective local dosages without excessive experimentation. The amount of compound administered will, of course, be dependent on the subject being treated, on the subject's weight, the severity of the affliction, the manner of administration, and the judgment of the prescribing physician. The therapy may be repeated intermittently while symptoms are detectable or even when they are not detectable. The therapy may be provided alone or in combination with other drugs.

"THERAPEUTIC INHIBITION" refers to the inhibition of a moiety that otherwise would potentially cause or contribute to a condition or disease in a subject.

"TISSUE INJURY" refers to the tissue where C5b-9 (MAC) is found to injure the tissue. Tissue injury is caused by the MAC and can be inhibited by the antibodies that prevent MAC formation. One example shown in the application is the quantifiable death of erythrocytes in a time dependent manner in the presence of normal human serum that contains physiological levels of complement components. This demonstration of lysis of cells is quantifiable by the loss of scattering at OD700. Nucleated cells present in tissues are also injured by complement similar to erythrocytes. Inhibition of erythrocyte lysis and therefore tissue injury can be prevented by the use of antibodies of this invention. Tissue injury can occur in any part of the body/organs and can lead to pathological outcome such as arthritis. In arthritis or osteoarthritis, tissue injury and damage can be prevented by the use of such antibodies. This definition can be extended to many diseases where tissue injury occurs as a result of AP activation but not CP activation.

This application relates to methods for treating a subject suffering from arthritis, or an arthritis related, or arthritis-like, condition by administering to an afflicted subject a therapeutic effective amount of one (or several) of a specific genus of inhibitory antibodies. The antibodies of this genus have been identified and selected, from a variety of antibodies inhibiting the complement system, for their specific and unique effect on specific components of the alternative pathway. The inhibitory antibodies of the selected genus are identified and selected using a specific combination of selection criteria. The antibodies produced from this combination of selection criteria are useful for multitude of arthritic conditions and other diseases.

Referring to FIG. 1, we show that both CP and AP are distinct and not connected. It is known that CP has an amplification loop and that connects the CP and the AP. The schematic only shows how the antibodies of the current genus work and not the way antibodies of other inventions work. AP amplification is shown in the upper right hand side and consists of PC3b, PC3bB, PC3bBb. As can be seen in the schematic, PC3bBb then acts to perpetuate the cycle by cleaving C3 into more C3b which binds to P to again form PC3b. Application of the antibodies selected using the screening method described herein completely inhibits the alternative pathway without affecting the classical pathway by specifically targeting the components of this amplification loop. These antibodies prevent the amplification loop of the alternative complement pathway without affecting the classical pathway (as shown on the left side of the schematic in FIG. 1).

Based on the old conversion of pathway at C3 theory, those with ordinary skill in the art would expect any activation of the classical pathway to invariably have the effect of triggering and propagating the alternative pathway. This is because the two pathways are believed to "overlap" at the starting point of the C3. According to this theory, C3b produced via the classical pathway participates in the AP amplification loop. The genus of antibodies selected using the method described herein specifically targets components of the alternative pathway amplification loop in such a way as to inhibit the alternative pathway regardless of whether or not the AP amplification loop has been otherwise triggered by the classical pathway. Thus, for example, anti-C3b antibodies described herein only inhibit the AP and not the CP amplification loop or the CP propagation.

The "Screening Method": Selection of Antibodies that Inhibit the Alternative Complement Pathway, do not Inhibit the Classical Complement Pathway, and are Specific for Components of the AP C3 Convertase Antibodies specific for complement proteins belonging to the alternative pathway (whether part of the CP amplification loop or an alternative pathway by itself), such as C3b, P, Ba, and Bb can be screened using a "Screening Method" described herein to select antibodies to inhibit alternative complement pathway without affecting the CP or the amplification loop of the CP. C3b, P, Ba, and Bb are large proteins of, respectively, 210K, 50K, 33K, and 66K molecular weight. One skilled in the art can generate millions of antibodies to each of these proteins. Production of antibodies to a target is, by itself, meaningless without further selection of those antibodies as having a specific therapeutic function.

In some embodiments, the Screening Method can include a two-stage screening process. The first stage utilizes three successive screening assays to identify Type AP antibodies (antibodies which specifically inhibit the AP). The selection process leads to identification of alternative pathway specific antibodies which are similar in functionality but targeted to a wide variety of antigens. These selected antibodies cannot be differentiated based on the targets they bind to or the species of animals in which they were raised. Upon sequencing, it is clear that such antibodies have widely different CDRs (the regions involved in binding to antigens). The functionality, and ultimate therapeutic value, of these antibodies can't be defined by their sequences alone. The Screening Method described herein can identify and define a genus of antibodies against Properdin (P), Factor C3b (C3b), and/or Factor B (Ba, or Bb) which have the desired functionality and effect.

A1) Step 1: Selection Based on Function

Three distinct types of antibodies can be identified using specific assays. The antibodies can be referred to as Type CP, Type CP/AP, and Type AP, and are defined as follows.

Type CP: These inhibit the classical pathway but not the alternative pathway.

Type CP/AP: These inhibit both the classical pathway and alternative pathway.

Type AP: These inhibit the alternative pathway but not the classical pathway.

Identification of these three different types of complement inhibiting antibodies is accomplished using three different assays; a CP only assay, a combined CP and AP assay, and an AP only assay.

Type CP

Figure 2:
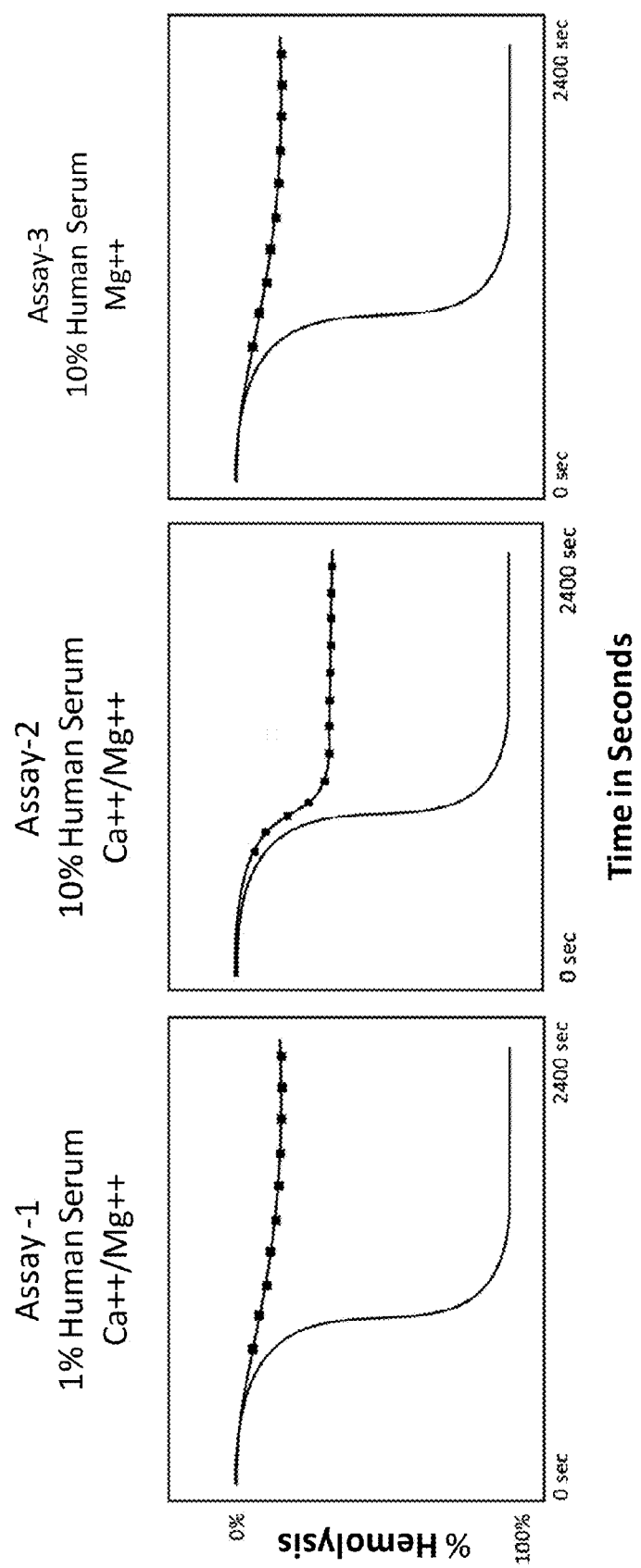
FIG. 2 illustrates graphs showing three assay figures (Step 1 of The Selection Process). These hemolysis graphs are for illustrative purposes only (as representations of model examples) and do not represent any particular set of real data. Selection of buffer and serum concentration is important for selecting antibodies that inhibit the alternative pathway. In Assay-1, a hypothetical antibody-1 inhibits the classical pathway hemolysis (dotted line). In Assay-2, a hypothetical antibody-2 inhibits the amplification loop, and in Assay-3, a hypothetical antibody-3 inhibits only the alternative pathway.
Figure 6:
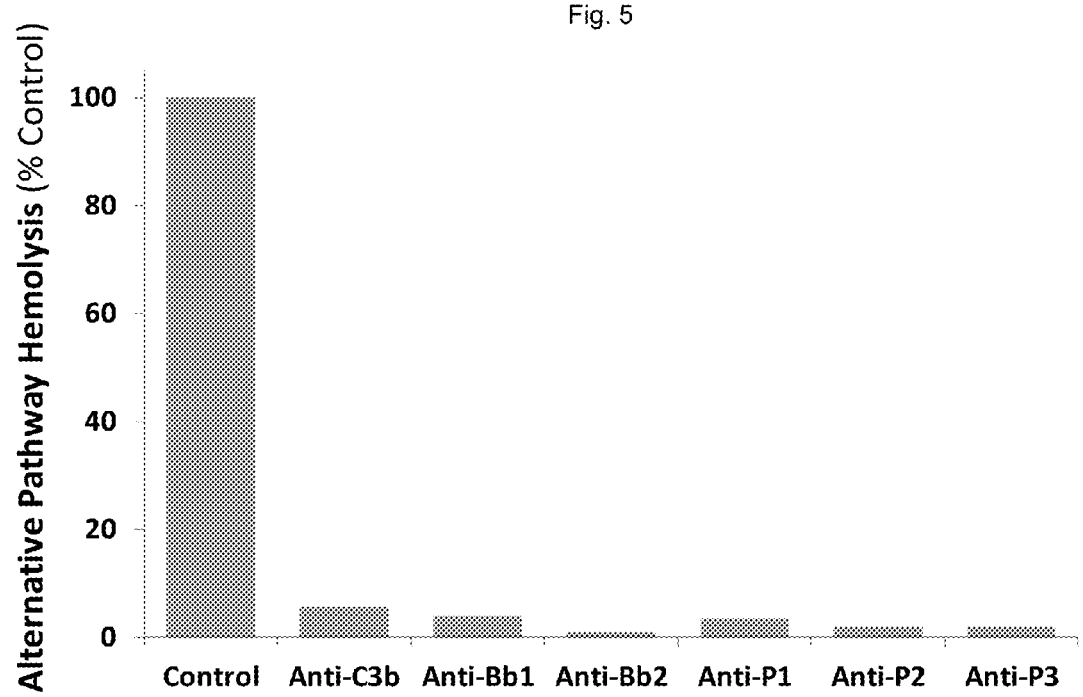
FIG. 6 illustrates a graph showing that the selected antibodies inhibit alternative pathway dependent hemolysis of rabbit erythrocytes (rRBC) in Human Serum (NHS). There exist a multitude of antibodies which inhibit the activities of Properdin (Factor P), Factor Bb, and C3b. All such antibodies inhibit the alternative pathway and not the CP (FIG. 7). However, these antibodies will act on their targets in such a way as to inhibit the alternative pathway without inhibiting the classical pathway.
Figure 7:
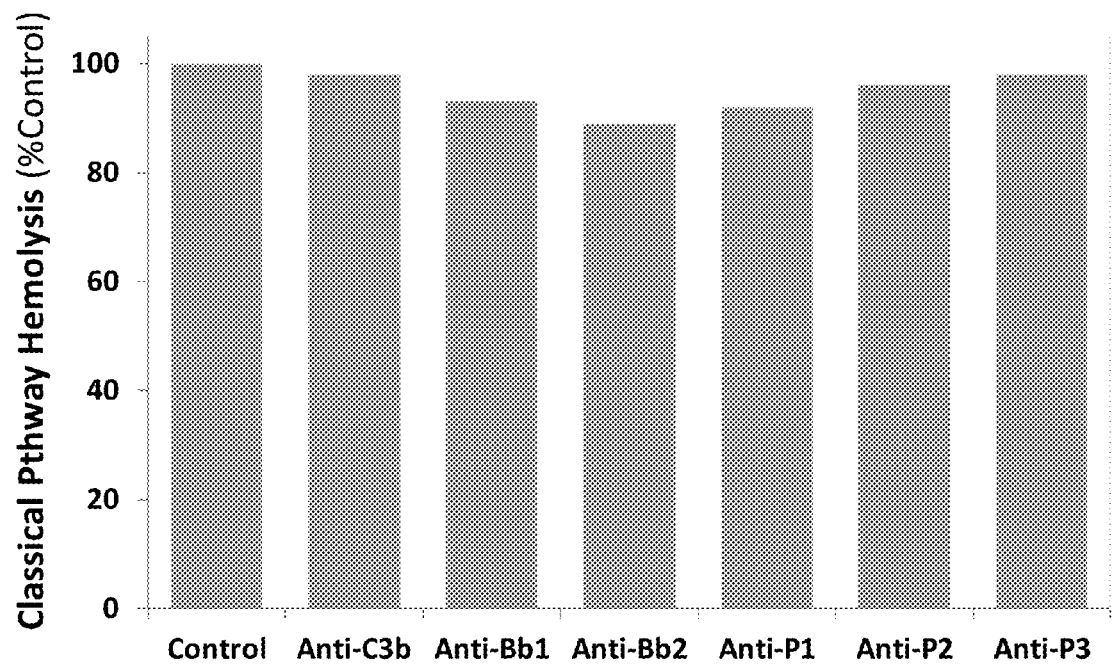
FIG. 7 illustrates a graph showing that the selected antibodies do not inhibit classical pathway dependent lysis of Antibody Sensitized Sheep Erythrocytes (sRBC). The current state of the act teaches that activation of the classical pathway invariably results in activation of the alternative pathway at the amplification loop, which begins with cleavage of C3 by CP produced C3 convertase.

For classical pathway activation, antibody sensitized sheep cells are used as an activator in 1% normal human serum in the presence of Ca2+/Mg2+. The calcium ions are required for the activation of the classical pathway for the initial trigger of the C1q/C1r/s complexes. CP will not occur in the absence of the Calcium ions. Mg2+ is required for alternative pathway activation. In 1% normal human serum containing Ca2+/Mg2+, only the CP proceeds to completion. Without the requisite levels of NHS which is 10%, the alternative pathway will not have a significant presence. FIG. 2, Assay-1 shows that shows that CP activation leads to the lysis of antibody sensitized sheep red blood cells. Antibody bound sRBCs act as a trigger for the classical pathway. The observed CP activity is isolated from AP activity by using a 1% buffer solution containing Ca2+ and Mg2+. FIG. 6 also shows that none of the selected antibodies materially inhibit CP mediated hemolysis of the sRBCs in 1% human serum in classical pathway condition.

Type CP/AP

For classical pathway activation, along with the amplification loop of the alternative pathway, antibody sensitized sheep red blood cells are used as an activator in 10%

Figure 3:
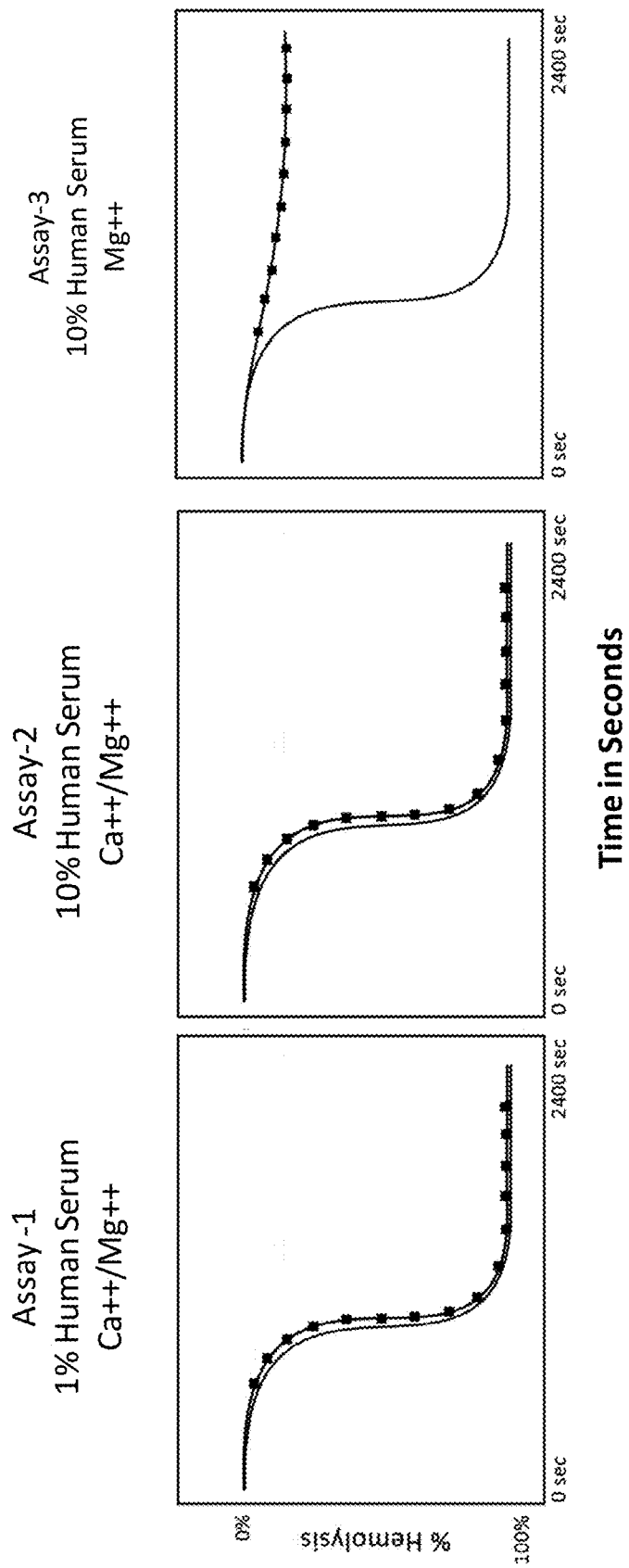
FIG. 3 illustrates graphs showing three assay figures (Step 1 of The Selection Process). These graphs are for illustrative purposes only (as representations of model examples) and do not represent any particular set of real data. The hypothetical antibody of the present invention (dotted line) does not inhibit Assay-1, Assay-2 but inhibits Assay-3 and is therefore selective for the alternative pathway.
Figure 4:
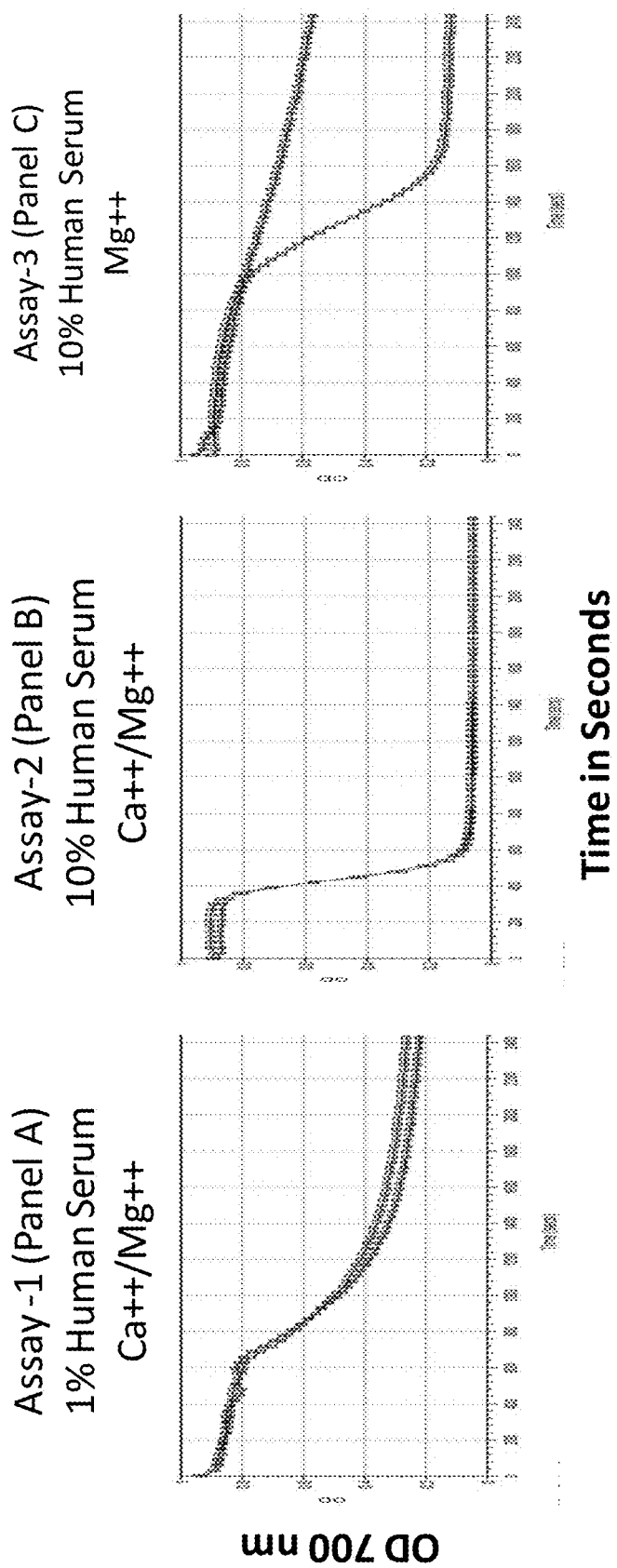
FIG. 4 illustrates graphs showing three assay figure tracings from real data generated from one of the selected antibodies as a representative FIG. 4. One line represents untreated sample whereas the second line represents the antibody treated sample. The Panel A is a CP assay conducted in 1% NHS in CP buffer. The second panel is a CP assay in 10% NHS that allows CP amplification loop to contribute into the AP. The third panel (Panel C) shows inhibition by the selected antibodies of the genus that inhibit the AP without affecting the CP (Panel B). All antibodies showing this pattern would belong to the selected genus.
Figure 5:
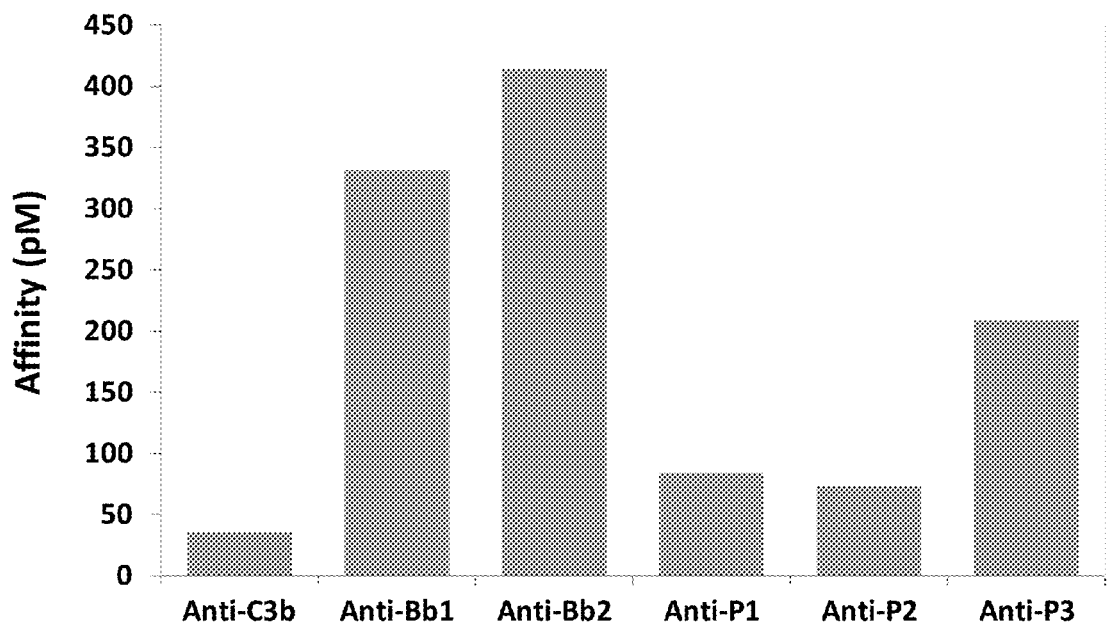
FIG. 5 illustrates a graph showing the binding affinities of the selected antibodies to their respective targets (C3b, Bb, and P). Shown are three different anti-P antibodies and two different Bb antibodies.

Ca2+/Mg2+ in normal human serum. The difference between the assays used to identify Type CP antibodies and those used to identify Type AP/CP antibodies is the concentration of normal human serum which is 10% in Type CP/AP. The concentration of Ca2+/Mg2+ used in the identification of Type AP/CP antibodies, by providing the level of Mg2+ required for AP activation, allows for both the CP and the AP to be active. Antibody sensitized sRBCs only activate the CP. They do not, by themselves, activate the Alternative Pathway. However, in the presence of sufficient NHS, activated CP will utilize the amplification loop of the AP. Thus, the assay system is designed to evaluate the performance of complement inhibitors under conditions in which both pathways are active (FIG. 3, Assay 2 and FIG. 4 Panel B). Under these conditions, the C3b produced via the classical pathway can feed into the alternative pathway causing "amplification of the alternative pathway loop" of the alternative pathway and can serve as a trigger indirectly. In other words, the AP has been activated by the CP. Antibodies that prevent CP initiated activation of the AP have been described in (R Gupta-Bansal, J B Parent, K R Brunden, Molecular immunology. 37(5):191-201). These antibodies reduced hemolysis of the sheep red blood cells in these assays. However, at this stage in The "Screening Method", the antibodies have yet to be differentiated according to how (and where) they inhibit the process. Antibodies which inhibit the classical pathway's activation of the AP by inhibiting any stage of the CP are not included in the selected genus of antibodies. Accordingly, the antibodies that inhibit the classical pathway initiated amplification of the alternative pathway have been excluded from the selected genus of antibodies.

Type AP

Rabbit RBCs (rRBC) are used to activate the AP in 10% normal human serum in the presence of Mg2+ and in the absence of Ca2+. Because the CP requires the presence of Ca2+, the classical pathway will not be active under these conditions. Thus, in 10% NHS in Mg2+, only the AP proceeds to completion. As shown in FIG. 2, Assay-3, AP activation leads to cellular lysis of the rRBCs. It should be noted that this assay demonstrates that the alternative pathway can be activated, and progress to completion, in the absence of active classical pathway function. The AP does not require initiation by the classical pathway in order to proceed. FIG. 4 clearly shows that the invention genus of antibodies inhibits AP dependent hemolysis of rRBCs in 10% normal human serum.

When an antibody's effect on AP activation and progression is observed in isolation, with the AP as a stand-alone process, the information obtained is different than the information obtained from observation of the antibody's effects in conditions where both the CP and the AP are active. The information obtained here is also different than that obtained from observation of the antibody's effect in conditions where only the CP is active.

Analysis of the Three Assays

If the presence of a particular antibody(s) in one of these three assays was found to reduce the rate of hemolysis, it was concluded that that antibody inhibits the pathway, or pathways, which were active in that assay. Thus, for example, if an antibody was found to reduce hemolysis in all three assays, it was concluded that the antibody inhibited both the AP and the CP (Type CP/AP). If an antibody was found to inhibit hemolysis only in assays containing 1% human serum (with Ca2+/Mg2+ buffer) it was concluded that that antibody inhibited the CP but not the AP (Type CP). If an antibody was found to inhibit hemolysis only in the assays containing 10% human serum and Mg2+ (but not Ca2+), it was concluded that the antibody inhibited the AP but not the CP.

|  | CP Only Assay 1% Human Serum Ca2+/Mg2+ | CP & AP Assay 10% Human Serum Ca2+/Mg2+ | AP Only Assay 10% Human Serum Mg2+ only |
|---|---|---|---|
| Type CP | Inhibition of Lysis | Partial Inhibition of Lysis | No Inhibition of Lysis |
| Type CP/AP | No Inhibition of Lysis | Partial Inhibition of Lysis | Inhibition of Lysis |
| Type AP | No Inhibition of Lysis | No Inhibition of Lysis | Inhibition of Lysis |

This is the first stage of The Screening Method. Antibodies passing these selection criteria have been shown to: 1) inhibit the alternative pathway under conditions in which the alternative pathway is active in isolation (i.e., without concurrent activation of the classical pathway), and 2) have no effect on CP activity (either in isolation or when concurrent with AP activity).

The invention uses this combination of assays to first identify Type AP antibodies. However, additional screening steps are needed in order to identify the selected genus of antibodies. Additional screening is necessary because these assays will identify antibodies in both the upstream and the downstream portion of the AP and the CP.

A2) Step 2: Selection of Those Type AP Antibodies which Act on C3 Convertase Formation The second step of the Screening Method is to identify which Type AP antibodies inhibit only the functional activity of AP C3 convertase. In other words, this step identifies those Type AP antibodies which act "up-stream" of the alternative complement pathway system, at the amplification loop of the AP, rather than "down-stream."

This step is accomplished by first establishing a solid phase ELISA based binding assay. This assay allows for the direct detection of C3b and C5b-9 produced via the alternative pathway. Detections of these proteins represent an early component (C3b) and a late component (C5b-9) of the alternative complement pathway. If an antibody inhibits production of C5b-9 but not C3b, it is likely to be acting on the C5 convertase of the AP. By contrast, C3b production will be inhibited by antibodies that inhibit the activity of the C3 convertase. Inhibition of C3b production will also inhibit production of C5b-9 (because C5b-9 is produced downstream of C3b). Thus, Stage 2 of The Screening Method separates antibodies inhibiting C3 convertase (up-stream) from those inhibiting C5 convertase (down-stream).

Figure 8:
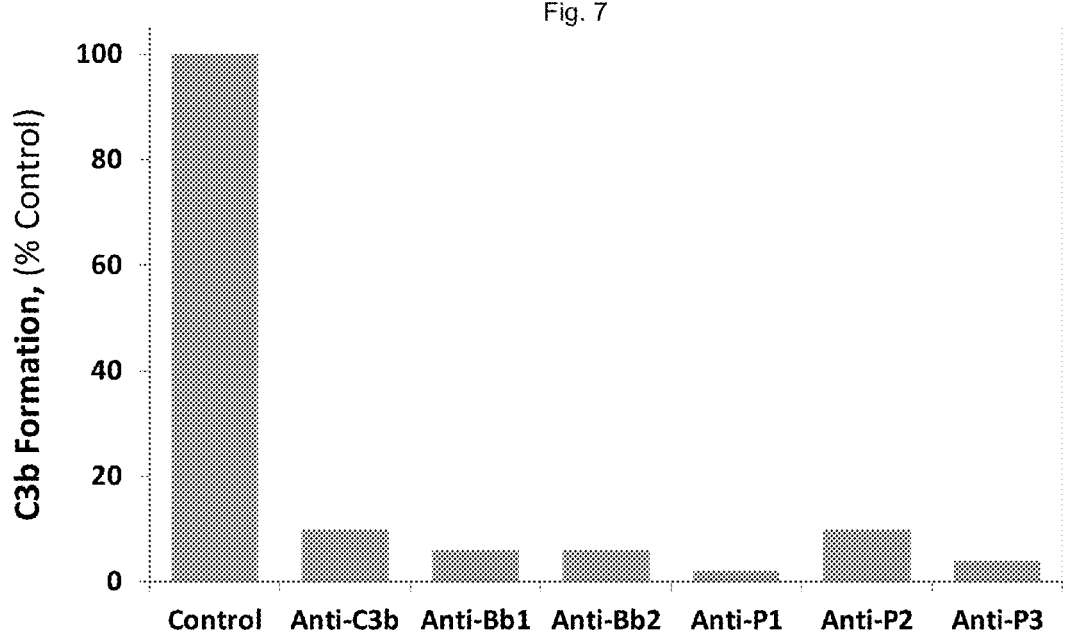
FIG. 8 illustrates a graph showing that the selected antibodies inhibit the formation of C3b in NHS.
Figure 9:
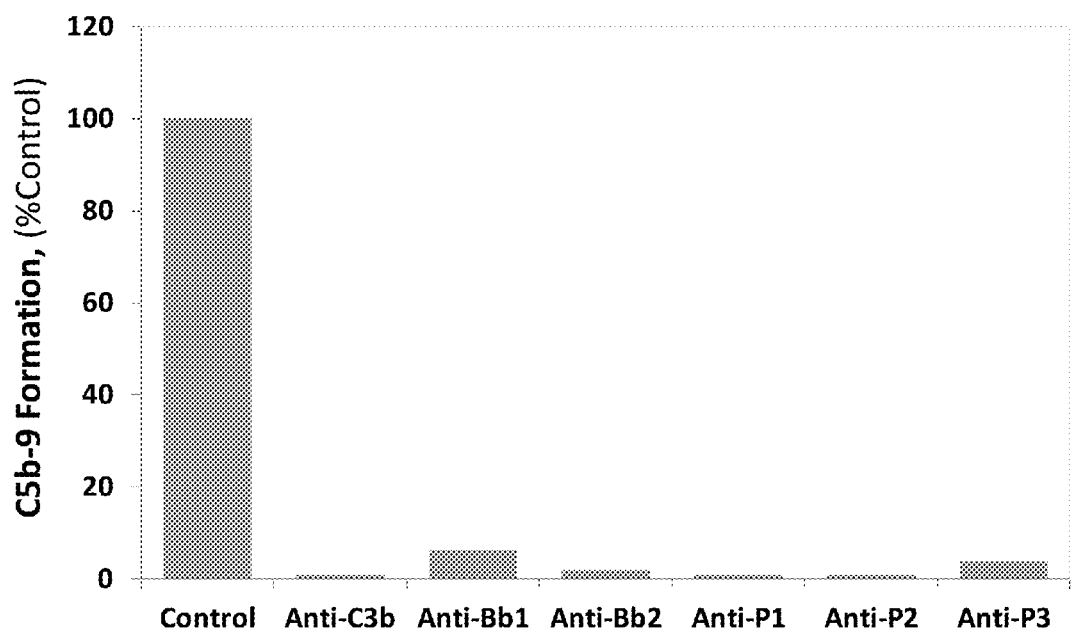
FIG. 9 illustrates a graph showing that the selected antibodies inhibit the formation of C5b-9 in NHS.

The Screening Method identified antibodies that selectively inhibit the AP C3 convertase. This stage of selection utilizes an assay in which human serum at 10% in the presence of Mg++ is allowed to incubate over an LPS coating. LPS is a specific activator of the alternative pathway and can allow formation of AP derived C3 convertase and C5 convertase. As shown in FIG. 8, the selected genus of antibodies prevents the formation of C3b, a central component of the alternative pathway amplification loop. FIG. 9 shows that they also inhibit formation of C5b-9.

At the conclusion of the this stage selection process, antibodies that prevent the AP dependent cellular lysis and C3b formation (FIG. 8) are selected as being members of the selected genus of antibodies. These antibodies are defined by the fact that they all: 1) selectively inhibit the alternative pathway without inhibiting the classical pathway (FIG. 4), and 2) inhibit the alternative pathway dependent C3b formation, by acting on C3 convertase formation, an upstream component of the AP.

Figure 10:
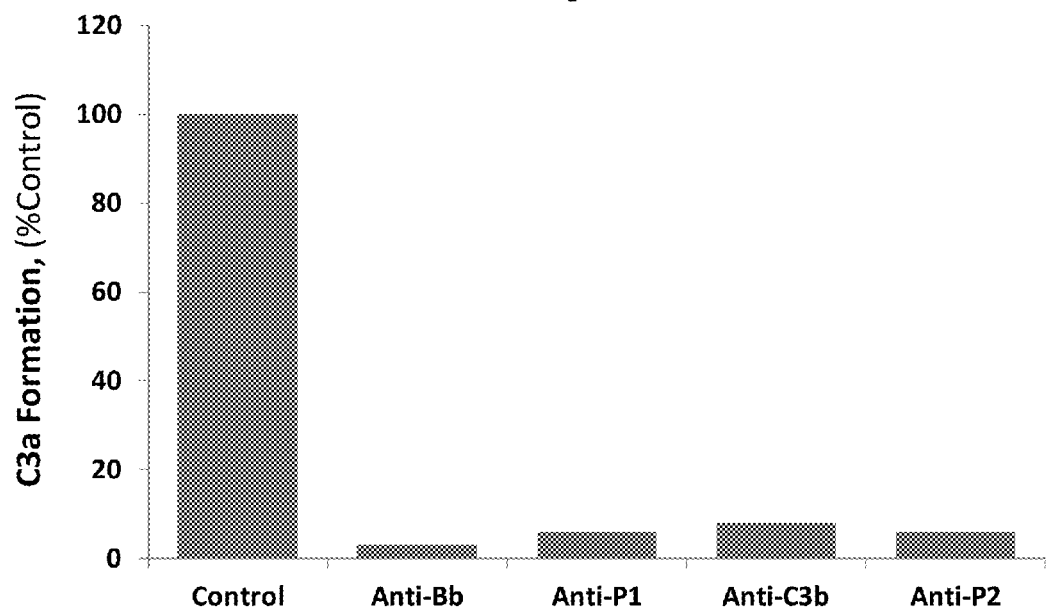
FIG. 10 illustrates a graph showing that the selected antibodies inhibit the formation of C3a in Whole Blood Inflammation. Both C3a (cleaved from C3) and C5a (cleaved from C5) are potent anaphylatoxins (triggers of local inflammation) that are produced upon complement activation. Both the classical pathway and the alternative pathway produce these molecules. The Figure shows the inhibition of C3a derived from the alternative complement pathway. C trigger does not exist in this model.
Figure 11:
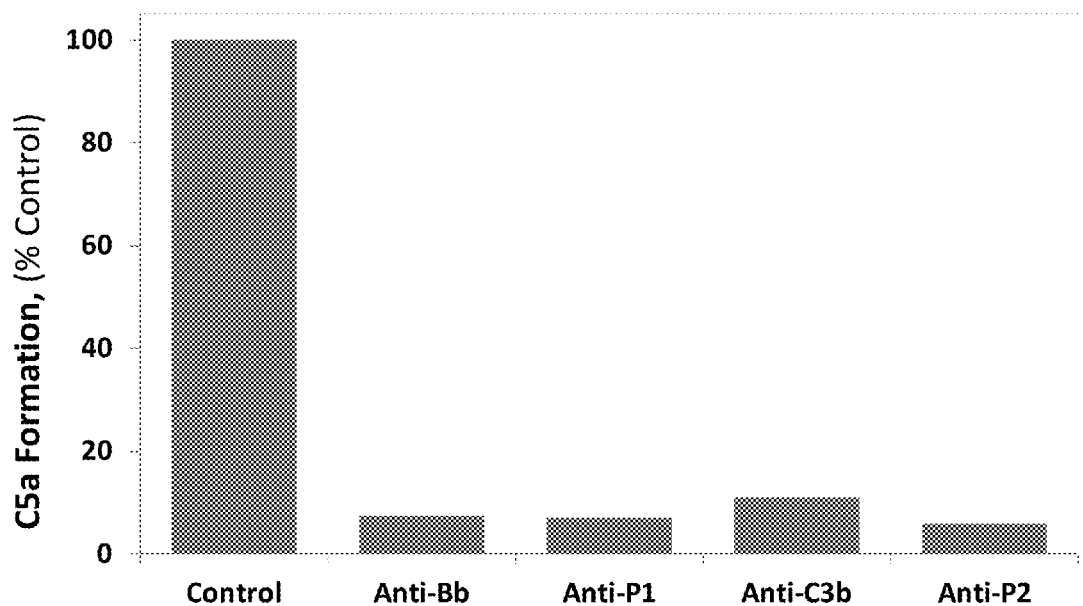
FIG. 11 illustrates a graph showing that the selected antibodies inhibit the formation of C5a in Whole Blood Inflammation. The claimed invention selectively inhibits C3a (FIG. 8) and C5a (FIG. 9) produced from the alternative pathway.
Figure 12:
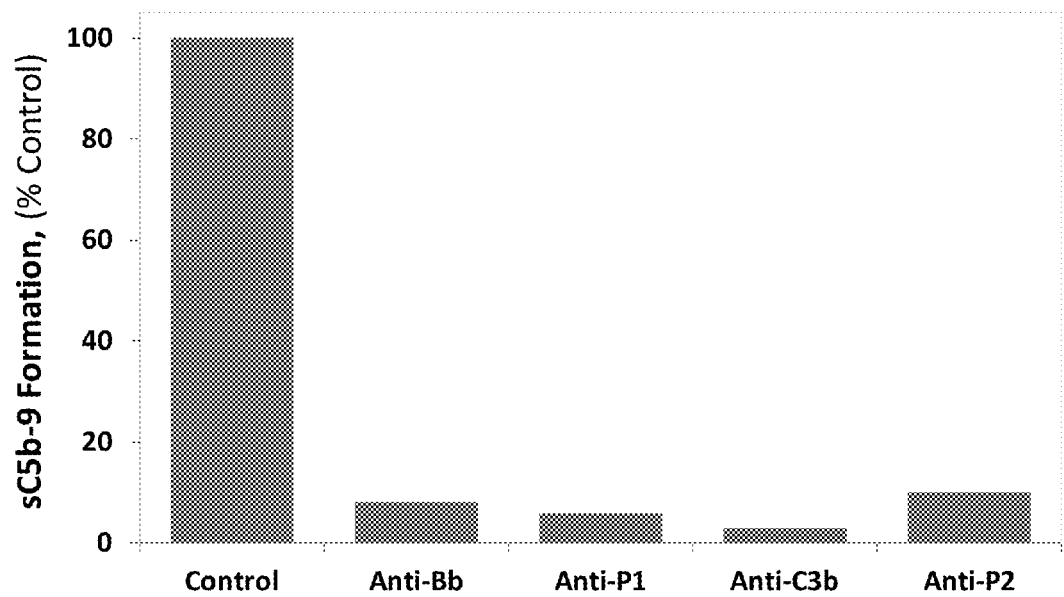
FIG. 12 illustrates a graph showing that the selected antibodies inhibit formation of sC5b-9 in Whole Blood.
Figure 13:
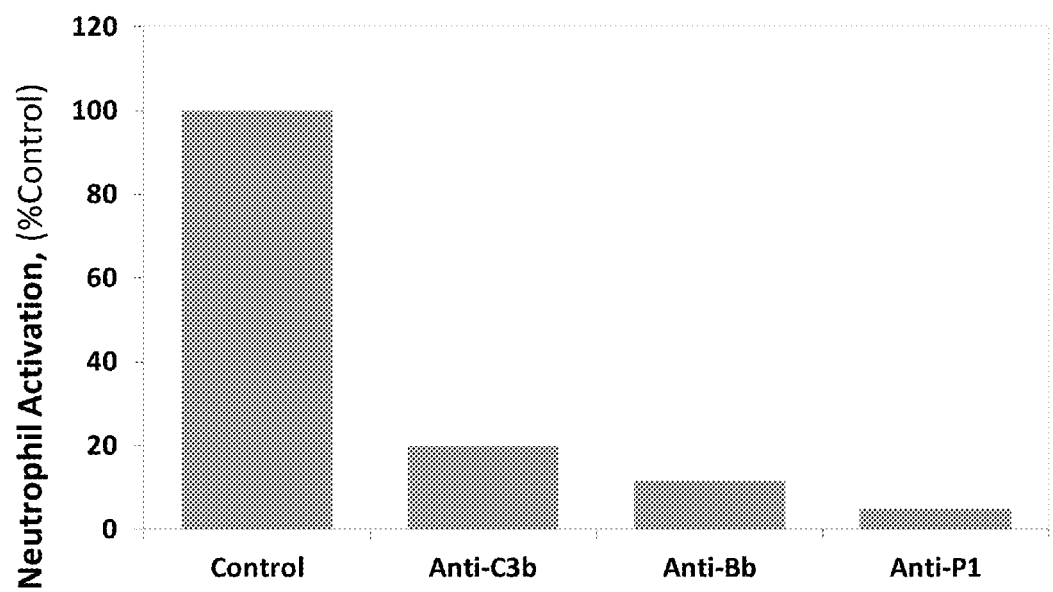
FIG. 13 illustrates a graph showing that the selected antibodies inhibit neutrophil activation. The neutrophils activation occurs due to the activation of the AP and not CP or CP-induced AP.
Figure 14:
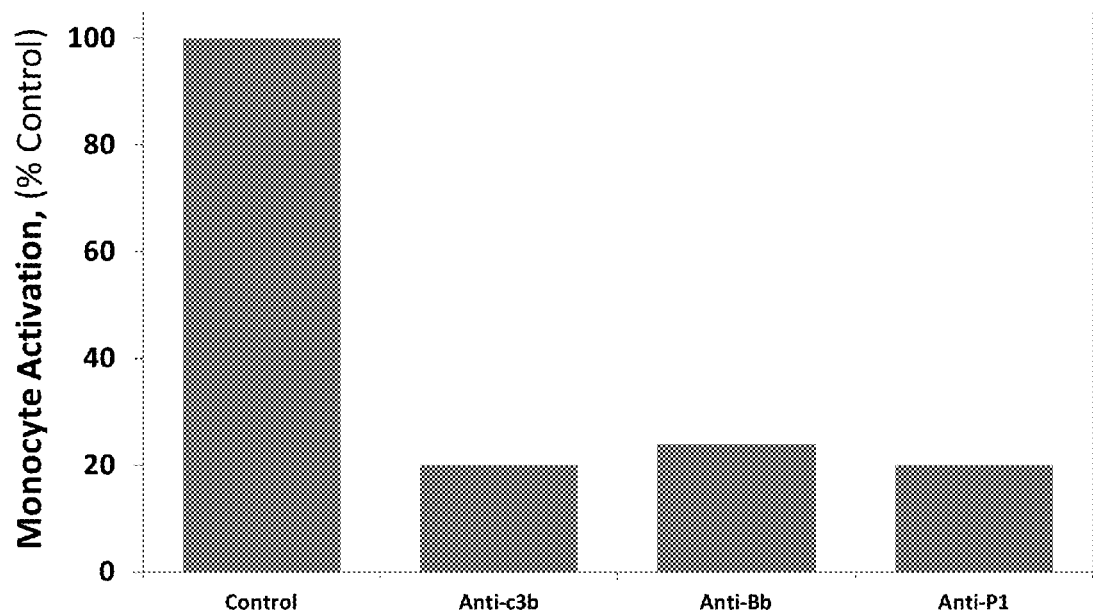
FIG. 14 illustrates a graph showing that the selected antibodies inhibit monocyte activation. The monocyte activation occurs due to the activation of the AP and not CP or CP-induced AP.
Figure 15:
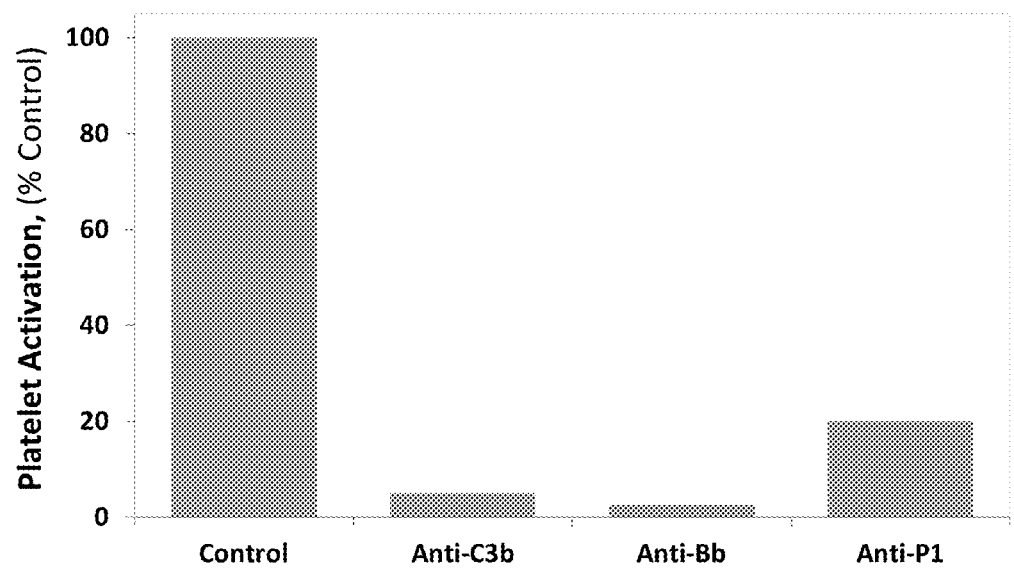
FIG. 15 illustrates a graph showing that the selected antibodies inhibit platelet activation. The platelet activation occurs due to the activation of the AP and not CP or CP-induced AP.
Figure 16:
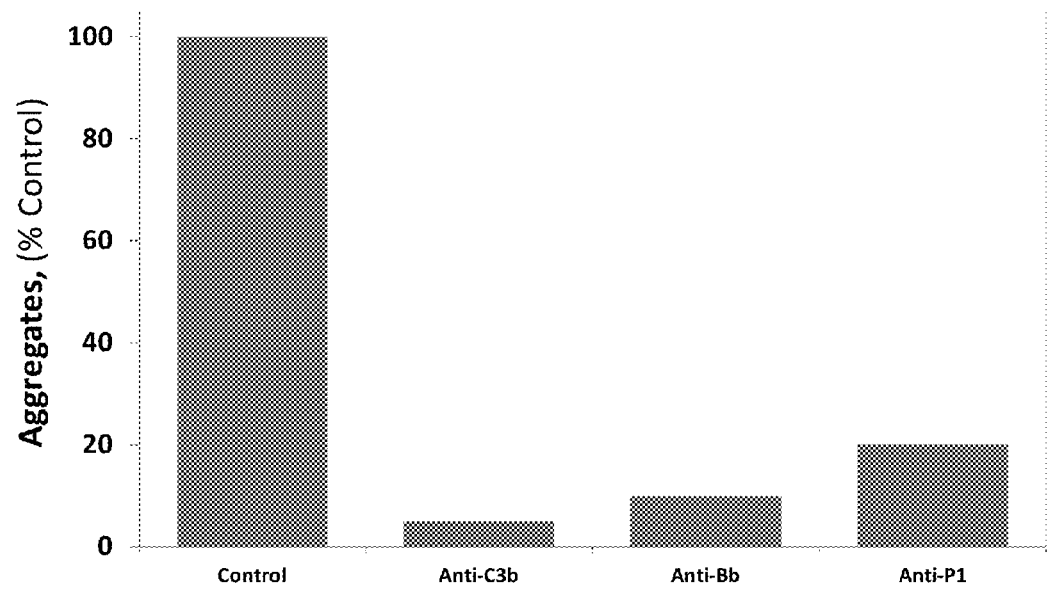
FIG. 16 illustrates a graph showing that the selected antibodies inhibit monocyte-platelet aggregates. The monocyte-platelet aggregation occurs due to the activation of the AP and not CP or CP-induced AP.
Figure 17:
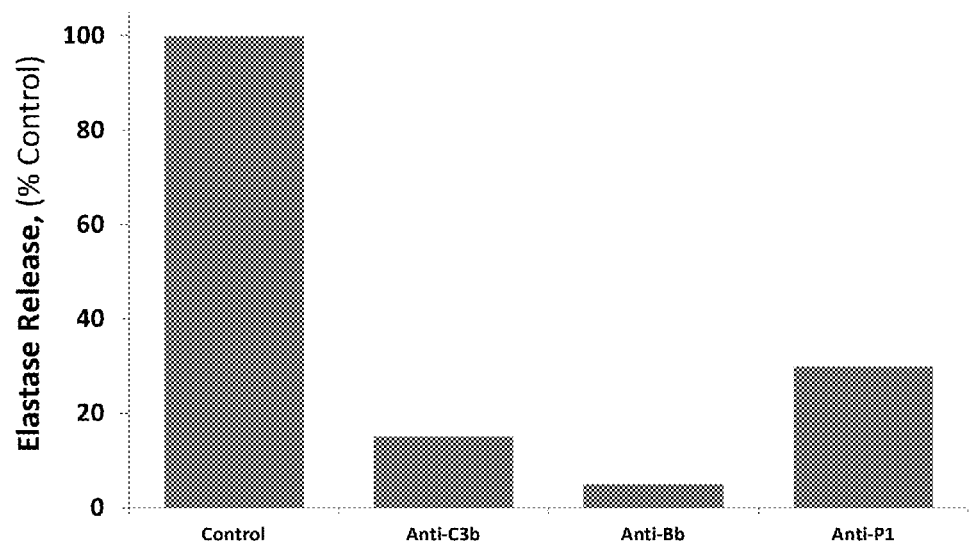
FIG. 17 illustrates a graph showing that the selected antibodies inhibit elastase release from neutrophils. The neutrophil elastase is produced from neutrophils that are activated via the C3a/C5a produced from the alternative pathway.

FIGS. 10 and 11 show that the selected genus of antibodies inhibits formation of complement proteins C3a and C5a, respectively.

Selected Genus of Antibodies

Application of the Screening Method has thus far produced several antibodies from the selected genus of antibodies.

C3b as Target Protein

Mouse Anti Human C3b (Anti-C3b)

C3b is a large protein and therefore multiple antibodies can be produced against various segments of this protein. There exist multiple sites where-on an antibody might bind and inhibit the protein's activity in any variety of ways. Depending on how and where an antibody binds to C3b, the effect of that antibody could range from inconsequential to complete inhibition. Injecting a mouse with Human C3b will result in the production of a myriad of mouse antibodies against the Human C3b protein.

The selected genus of antibodies include those that bind to C3b in such a way as to prevent the interaction of C3b with Factor B. The effect of these antibodies is necessarily isolated to the alternative pathway since no such interaction exists within the classical pathway. These antibodies prevent the formation of C3a/C3b, C5a/C5b, and C5b-9/sC5b-9 critical for pathological outcome causing disease initiation and progression. Inhibition of the formation of each of these molecules, by the alternative pathway, has significant physiological consequences. Inhibition of alternative pathway produced C3b (herein referred to as "aC3b") impacts extravascular hemolysis of erythrocytes. The C3b produced by the classical pathway is not inhibited by these antibodies and therefore is required for opsonization of foreign particles/bacteria that are coated with CP produced C3b (herein referred to as "cC3b"). Thus, the selected genus of antibodies prevents the formation of aC3b and not cC3b by such antibodies that have this as a common function. The inhibition of C3a formation has direct effect on monocytes activation and production of TNF-α which is a validated marker of inflammation.

Properdin as Target Protein

As is the case with C3b, Properdin is a large protein with many potential sites where antibodies can bind. Different antibodies binding in different ways and/or on different sites of the Properdin protein, will inhibit either amplification loop of the classical pathway or alternative pathway. Properdin is known to be part of the amplification loop of the classical pathway. Thus, classical pathway activation can be dampened by the use of specific anti-properdin antibodies that inhibit the amplification loop (U.S. Pat. No. 6,333,034). Some antibodies can inhibit the classical pathway activation where interactions of Properdin to C3b, within the classical pathway, become important for classical pathway amplification. (U.S. Pat. No. 6,333,034)

Properdin binds to itself and generates aggregates. Depending upon the configuration of the aggregate, antibodies binding Properdin can bind mono, di-, tri- and tetramer, with each generating different responses. Thus antibody-to-properdin ratio can be 1:1, 1:2, 1:3, and 1:4. This means that an antibody can bind in any configuration. An assay can be used to separate antibodies in a rank order according to potency, by the ratio at which they bind Properdin. In other words, antibodies that bind at a 1:1 ratio can be separated from those that bind at a 1:2 ratio, a 1:3 ratio and a 1:4 ratio. A binding ratio of 1:1 suggests that the antibody binding is via one arm and not by two arms. Such antibodies demonstrate a 1:1 binding ratio regardless of whether or not the antibody is a Fab (monovalent) or the IgG (divalent).

Properdin is involved directly in the AP activation but indirectly in classical pathway activation via the amplification loop in vivo. Also, Properdin binds both C3b and C5b. An antibody which disrupts Properdin's interaction with C3b may or may not interrupt Properdin's interaction with C5b (and vice versa). Antibodies that prevent one or both may be of distinguishable clinical significance.

Thus, some antibodies targeting Properdin a) inhibit both the classical pathway and alternative pathway, or b) inhibit the alternative pathway alone. The selected genus of antibodies would only include those antibodies targeting Properdin which acted on Properdin in specifically such a way as to only inhibit the AP, and not the CP.

Anti Human P (Anti-P) Derived from Mouse

The protein Properdin (P) is a large protein with a molecular weight of approximately 50,000. A multitude of antibodies can be produced against various protein motifs of this large protein. Not all, or even most, of these antibodies will necessarily have any therapeutic value. Identification and selection of the appropriate antibody, or antibodies, those with optimal therapeutic value, is crucial.

Two mouse anti-human-P antibodies were selected using a proprietary combination of successive screening methods. The Screening Method enabled this inventor to identify those antibodies which 1) bind to human Properdin, 2) selectively inhibit only the activity of the alternative complement pathway, and 3) interrupt the alternative pathway in such a way as to not disrupt the amplification loop of the classical pathway. These antibodies bind properdin as the target antigen. And they do so in such a way as to inhibit the formation of the P(C3b)n, PC3bB and PC3bBb, and by extension, (Bb)n and C3bBb. The inhibition of these specific complexes is one of the essential and defining common characteristics of all the antibodies of the selected genus. In preventing the formation of these complexes, these antibodies all prevent the alternative pathway's production of C3b, C5a, C5b, and C5b-9, as well as TNF-α, IL-1.

Anti Human P (Anti-P) Derived from Rabbit

Three rabbit anti-human-P antibodies were selected using the Screening Method (the same that was used for selecting the anti-human-P mouse antibodies). As can be seen in FIG. 2, these antibodies inhibit the alternative pathway dependent lysis of rabbit red blood cells (rRBC) in normal human serum (NHS) in buffer that lacks calcium and therefore there is no contribution from the classical complement pathway. In doing so, the effect of these antibodies is targeted, and isolated, to a section of the alternative pathway which does not overlap with the classical pathway. These antibodies prevent the formation of C3a, C3b, C5a, C5b, and C5b-9. The formation of these specific proteins is the critical step in the alternative pathway wherein a normal immune system process can become the source of a pathological condition. It's the overproduction of these proteins from the alternative pathway that often cause arthritic conditions.

The selected alternative pathway specific anti-human-P antibodies generated in rabbits are analogous in effect to those from the mouse models. They are analogous in effect because both the mouse and the rabbit derived antibodies were selected using The Screening Method. They inhibit the formation of C3a, C3b, C5a, C5b, and C5b-9; thereby inhibiting the activation of monocytes, neutrophils, platelets, and the formation of TNF-α (which also plays a key role in inflammation).

Sequences of these anti-properdin rabbit antibodies are very different as shown in the tables noted below. Therefore, looking at the protein sequences alone would not necessarily yield any understanding of their effect on Properdin. Unless tested using the Screening Method, it would be difficult to determine if a given antibody belongs to the selected genus of antibodies. Accordingly, the selected genus of antibodies can't be defined by a specific amino acid sequence. Rather, the genus is defined by the ability of its member antibodies to 1) selectively inhibit AP activation without disrupting any function of the CP, and b) act on a specific part of the AP that is isolated from the CP and which is responsible for AP production of C3a, C3b, C5a, C5b, and C5b-9.

Ba as Target Protein
Anti Human Ba (Anti-Ba) Derived from Mouse

The protein Ba (cleaved from Factor B) is a large protein with a molecular weight of approximately 33,000. Thus, like Properdin and C3b, any of a multitude of antibodies can be produced against various protein motifs of, and locations on, the protein. With this protein, as with the other proteins of the AP, the invention is a selected genus of antibodies which bind to the protein in such a way as to inhibit the formation of C3a, C3b, C5a, C5b, and C5b-9, which are required for the pathological progression of the disease.

As can be seen in FIG. 3, these antibodies inhibit the alternative pathway dependent lysis of rabbit red blood cells (rRBC) in normal human serum (NHS) in a buffer that lacks calcium. The classical pathway can't function in a buffer which lacks calcium. Thus, in these conditions, there is no contribution from the classical complement pathway. Such conditions enable one to observe the effect these antibodies have on the alternative complement pathway in the complete absence of the classical pathway. Observing the antibodies under these conditions is one step of the Screening Method by which the antibodies of the invention are identified.

The sequencing of these anti-alternative pathway antibodies are very different. Thus, here again we observe that the selected genus of antibodies can't be defined by a specific amino acid sequence. Rather, the genus is defined by those which are selected by The Screening Method.

Bb as Target Protein
Anti Human Bb (Anti-Bb) Derived from Mouse

The protein Bb (cleaved product of Factor B) is a large protein with a molecular weight of approximately 64,000. Thus, where again we find that several antibodies can be produced against various protein motifs of this protein. Again we apply the Screening Method in order to produce only those antibodies which have the desired effects.

Mouse anti-human-Bb antibodies were raised against factor Bb and therefore would not bind the Ba fragment of the antibody. These monoclonal antibodies were also selected using the Screening Method. They bind Bb and factor B, but not Ba as the target antigen. The selected anti-human-Bb antibodies share the features characteristic of the selected anti-C3b, anti-P, anti-Ba antibodies. Like all of the antibodies from the selected genus of antibodies, these anti-human-Bb antibodies prevent the formation of C3a, C3b, C5a, C5b, and C5b-9 by the alternative pathway. In so doing, these antibodies also prevent the formation of well known markers of inflammation such as TNF-α, IL-1.

Anti Human Bb (Anti-Bb) Derived from Rabbit

Three rabbit anti-Human Bb antibodies were selected using the Screening Method. Members of the selected genus of antibodies which bind Bb do not also bind Ba. Factor B is an integral component of the alternative complement pathway but not the classical complement pathway. Antibodies binding human Bb, which survive The Screening Method, prevent the formation of complexes critical for the propagation of the alternative pathway; C3bB, PC3bB, C3bBb, PC3bBb, P(C3b)n(Bb)n. Like all antibodies of the invention, they prevent the AP induced formation of C3b, C3a, C5b, C5a, and C5b-9, and inhibit the AP at a juncture not shared with the classical pathway. Inhibition of formation of each of these molecules has physiologic consequences. Inhibition of C3b (aC3b) will impact extravascular hemolysis. Inhibition of C3a and C5a will impact cellular activation and subsequent release of inflammatory mediators. Inflammatory mediators, when over-produced, can cause any number of disease pathologies in humans.

As with other antibodies of the selected genus, sequences of these rabbit anti-Bb antibodies are very different. Therefore, looking at the protein sequences alone would not enable one to predict whether such antibodies could have the desired effect.

Table 1 and Table 2 list the amino acid sequences of the heavy and light chains of anti-C3b, anti-P, ant-Ba, and anti-Bb antibodies that were selected using the Screening Method described herein. The Tables identify the heavy chain and light chain CDR1s, CDR2s and CDR3s of the antibodies as well as in the respective frameworks. Accordingly, aspects of the application described herein, relate to an isolated monoclonal antibody, or antigen binding portion thereof comprising: (a) a heavy chain variable region comprising CDR1, CDR2, and CDR3, of the respective antibodies; and (b) a light chain variable region comprising CDR1, CDR2, and CDR3 of the respective antibodies. Other embodiments described herein relate to antibodies that bind to the same epitope on as the VH and VL sequences described in Tables 1 and 2.

TABLE 1

| Target | Species | SEQ ID F1 | CDR1 | FW2 | CDR2 | FW3 | CDR3 | FW4 |
|---|---|---|---|---|---|---|---|---|
| Properdin | Mouse | 1 DIQM TQTT SSLS ASLG DRVT ISC | RASQ DISFF LN | WYQQ KPDG TVKL LIY | YTSR YHS | GVPSR FSGSG SGTDF SLTINN LEQED FATYF C | QHG NTLP WT | FGG G |
| | | 2 | RASQ DISFF LN | | | | | FGG G |
| | | 3 | | | YTSR YHS | | | |
| | | 4 | | | | | QHG NTLP WT | |

TABLE 1-continued

| Target | Species | SEQ ID F1 | CDR1 | FW2 | CDR2 | FW3 | CDR3 | FW4 |
|---|---|---|---|---|---|---|---|---|
| Properdin | Mouse | 5 DIQMTQSPLSLSVSLGDQASISC | RSSQSLVHSNGNTYLH | WYLQKPGQSPKLLIY | KVSYRFS | GVPDRFSGSGSGTDFTLKISRVEAEDLGVYFC | SQNTHVPRT | FGGG |
| | | 6 | RSSQSLVHSNGNTYLH | | | | | |
| | | 7 | | | KVSYRFS | | | |
| | | 8 | | | | | SQNTHVPRT | |
| Properdin | Rabbit | 9 AYDLTQTPASVEAAVGGTVTINC | QASDNIYSLLA | WYQQKPGQPPKLLIY | RASTLAS | GVPSRFKGSGSGTQFTLTISGVECADAATYYC | QQHYDYNYLDVA | FGGGTEVVVKG |
| | | 10 | QASDNIYSLLA | | | | | |
| | | 11 | | | RASTLAS | | | |
| | | 12 | | | | | QQHYDYNYLDVA | |
| Factor Bb | Mouse | 13 DVQITQSPSYLAASPGETITINC | RASKSISKYLA | WYQDKPGKTNKLLIY | SGSTLQS | GIPSRFSGSGSGTDFTLTISSLEPEDFAMYYC | QQHDEYPWT | FGGGTKLEIKR |
| | | 14 | RASKSISKYLA | | | | | |
| | | 15 | | | SGSTLQS | | | |
| | | 16 | | | | | QQHDEYPWT | |
| Factor Bb | Rabbit | 17 AVVLTQTASPVSGVVGGTVTINC | QASENIYSRLA | WYQQKPGQPPRVLIY | YASDLAS | GVPSRFGGSGSGTDYTLTISDLECADAATYYC | HSYYWNSAYSDNT | FGGGTEVVVEG |
| | | 18 | QASENIYSRLA | | | | | |
| | | 19 | | | YASDLAS | | | |
| | | 20 | | | | | HSYYWNSAYSDNT | |
| Factor Bb | Rabbit | 21 DVVMTQTPSSVEAAVGGTVTIKC | QASENIYSYLA | WYQQKPGQPPKLLIY | KASYLAS | GVSSRFKGSGSGTEFTLTISDLECADAATYYC | LSTIASASNFDA | FGGGTEVVVKG |

TABLE 1-continued

| Target | Species | SEQ ID | F1 | CDR1 | FW2 | CDR2 | FW3 | CDR3 | FW4 |
|---|---|---|---|---|---|---|---|---|---|
| | | 22 | | QASENIYSYLA | | | | | |
| | | 23 | | | | KASYLAS | | | |
| | | 24 | | | | | | LSTIASASNFDA | |
| Factor Bb | Rabbit | 25 | DPVLTQTASSVSAPVGGTVTISC | QSSQSVYRSNNVA | WYQQKPGKPPKLLIY | EASSLAS | GVPSRFTGSGSGTQFTLTISGVQCDDAATYYC | AGGYSSSVDFFFA | FGGGTEVVVKG |
| | | 26 | | QSSQSVYRSNNVA | | | | | |
| | | 27 | | | | EASSLAS | | | |
| | | 28 | | | | | | AGGYSSSVDFFFA | |
| Factor C3b | Humanized | 29 | EIVLTQSPATLSASPGEKVTMTC | SATSSITYIH | WYQQKSGTSPKRWIY | DTSRLAS | GVPARFSGSGSGTSYSLTISTMEAEDAATYYC | QQWSSNPPT | FGGGTKLEIK |
| | | 30 | | SATSSITYIH | | | | | |
| | | 31 | | | | DTSRLAS | | | |
| | | 32 | | | | | | QQWSSNPPT | |

TABLE 2

| Target | Species | Seq ID | FW1 | CDR1 | FW2 | CDR2 | FW3 | CDR3 | FW4 |
|---|---|---|---|---|---|---|---|---|---|
| Properdin | Mouse | 33 | EVQLQQSVPELARPGASVKMSCTAS | GYIFTTYPIH | WVKQRPGQGLEWIG | FIDPGGGYDEPDDKFRD | RATLTADKSSTTAYMQLSSLTSEDSAVYYCAR | RGDGYYFDY | WGQG |
| | | 34 | | GYIFTTYPIH | | | | | |
| | | 35 | | | | FIDPGGGYDEPDDKFRD | | | |
| | | 36 | | | | | | RGDGYYFDY | |

TABLE 2-continued

| Target | Species | Seq ID | FW1 | CDR1 | FW2 | CDR2 | FW3 | CDR3 | FW4 |
|---|---|---|---|---|---|---|---|---|---|
| Properdin | Rabbit | 37 | QSLEESGGGLVKPGASLTLTCTAS | GFSFSSGYWIF | WVRQAPGKGLELVG | GIYSGSSGTTYYANWAKG | RFTISKTSSTTVTLQMTSLTAADTATYFCAR | SVDGIDSYDAAFNL | WGPGTLVTVSS |
| | | 38 | | GFSFSSGYWIF | | | | | |
| | | 39 | | | | GIYSGSSGTTYYANWAKG | | | |
| | | 40 | | | | | | SVDGIDSYDAAFNL | |
| Factor Bb | Rabbit | 41 | QSLEESGGRLVTPGTPLTLTCTVS | GFDLSTYAMS | WVRQAPGKGLEWIG | AVSATTGNTYYATWAKG | RFTMSKASTTVDLKITSPTTEDTATYFCVR | YASSGVGTYFDL | WGQGTLVTVSS |
| | | 42 | | GFDLSTYAMS | | | | | |
| | | 43 | | | | AVSATTGNTYYATWAKG | | | |
| | | 44 | | | | | | YASSGVGTYFDL | |
| Factor Bb | Rabbit | 45 | QSLEESGGRLVTPGGSLTLTCTVS | GFSLSNYHLG | WVRRAPGKGLEWIG | VITYGGSTYYASWVKG | RFTISKTSTTVDLKMTSLTTEDTATYFCAR | RDSGGYHLDL | WGQGTLVTISS |
| | | 46 | | GFSLSNYHLG | | | | | |
| | | 47 | | | | VITYGGSTYYASWVKG | | | |
| | | 48 | | | | | | RDSGGYHLDL | |
| Factor Bb | Rabbit | 49 | QSVEESGGRLVTPGGSLTLTCTVS | GFSLSSNAIN | WVRQAPGEGLDWIG | TIHTNTKTYYATWARG | RFTISRTSSTTVDLKVTSLTAADTATYFCGR | ADL | WGQGTLVTVSS |
| | | 50 | | GFSLSSNAIN | | | | | |
| | | 51 | | | | TIHTNTKTYYATWARG | | | |
| | | 52 | | | | | | ADL | |

TABLE 2-continued

| Target | Species | Seq ID | FW1 | CDR1 | FW2 | CDR2 | FW3 | CDR3 | FW4 |
|---|---|---|---|---|---|---|---|---|---|
| Factor C3b | Humanized | 53 | QVQLVQSGAEIVKPGASVKMSCKAS | GYTFTSYWIN | WVKQRPGQGLEWIG | DIYPVRGITNYSEKFKN | KAKMIPDTSTSTVYMQLSSLTSEDTAVYYCSR | GNFGNFDAMDY | WGQGTMVTVSS |
|  |  | 54 |  | GYTFTSYWIN |  |  |  |  |  |
|  |  | 55 |  |  |  | DIYPVRGITNYSEKFKN |  |  |  |
|  |  | 56 |  |  |  |  |  | GNFGNFDAMDY |  |
| Factor Bb | Mouse | 57 | QVQLQQSGAELAKPGASVRMSCKAS | GYTFTNYWIH | WVKQRPGQGLEWIG | YINPNTGYNDYNQKFKD | KATLTADKSSSTVYMQLSSLTSEDSAVYYCAR | GGQLGLRRAMDY | WGQGTSVTVSS |
|  |  | 58 |  | GYTFTNYWIH |  |  |  |  |  |
|  |  | 59 |  |  |  | YINPNTGYNDYNQKFKD |  |  |  |
|  |  | 60 |  |  |  |  |  | GGQLGLRRAMDY |  |

In other embodiments, an antibody described herein can comprises heavy and light chain variable regions comprising amino acid sequences that are homologous to the amino acid sequences of the preferred antibodies described herein, and wherein the antibodies retain the desired functional properties. For example, the invention provides an isolated monoclonal antibody, or antigen binding portion thereof, comprising a heavy chain variable region and a light chain variable region, wherein: (a) the heavy chain variable region comprises an amino acid sequence that is at least 80% homologous to the amino acid sequence of a heavy chain variable region listed in Table 2 for a respective antibody; (b) the light chain variable region comprises an amino acid sequence that is at least 80% homologous to the amino acid sequence of a light chain variable region listed in Table 1 for the respective antibody; and (c) the antibody specifically binds to respective protein, C3b, P, Ba, or Bb.

In various aspects, the antibody can be, for example, a human antibody, a humanized antibody or a chimeric antibody. In other aspects, the $V_H$ and/or $V_L$ amino acid sequences may be 85%, 90%, 95%, 96%, 97%, 98% or 99% homologous to the sequences set forth above. An antibody having $V_H$ and $V_L$ regions having high (i.e., 80% or greater) homology to the $V_H$ and $V_L$ regions of the sequences set forth above, can be obtained by mutagenesis (e.g., site-directed or PCR-mediated mutagenesis) of nucleic acid molecules encoding the amino acid sequences, followed by testing of the encoded altered antibody for retained function using the functional assays described herein.

As used herein, the percent homology between two amino acid sequences is equivalent to the percent identity between the two sequences. The percent identity between the two sequences is a function of the number of identical positions shared by the sequences (i.e., % homology=# of identical positions/total # of positions ×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

In certain aspects, an antibody of the invention can include a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the preferred antibodies described herein, or conservative modifications thereof, and wherein the antibodies retain the desired functional properties. Accordingly, the invention provides an isolated monoclonal antibody, or antigen binding portion thereof, comprising a heavy chain variable region comprising CDR1, CDR2, and CDR3 sequences and a light chain variable region comprising CDR1, CDR2, and CDR3 sequences.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function (i.e., the functions set forth in (c) through (j) above) using the functional assays described herein.

An antibody of the invention further can be prepared using an antibody having one or more of the $V_H$ and/or $V_L$ sequences disclosed herein as starting material to engineer a modified antibody, which modified antibody may have altered properties from the starting antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties. Thus, such antibodies contain the $V_H$ and $V_L$ CDR sequences described in the Tables yet may contain different framework sequences from these antibodies.

Another type of variable region modification is to mutate amino acid residues within the $V_H$ and/or $V_K$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Conservative modifications (as discussed above) are introduced. The mutations may be amino acid substitutions, additions or deletions, but are preferably substitutions. Moreover, typically no more than one, two, three, four or five residues within a CDR region are altered.

In general, therapeutic antibodies, once selected, can be manipulated, altered and engineered in a variety of ways for various different reasons. For example, the inactive (non-binding) parts of a selected antibody may be changed and manipulated in countless ways which do not at all change the defining functions of the antibody. In fact, the functional (protein binging part) of the antibody might be entirely severed from the rest of the antibody. These alterations may have utility for making the antibody easier or less costly to produce. Or, such alterations may make the antibody more chemically stable in human subjects. These manipulations and derivations of the selected antibodies are not new or separate inventions. Accordingly, any such manipulations, alternations and derivations of the selected genus of antibodies which utilize the same defining characteristics of the genus itself are within the scope of the invention.

The invention includes compounds which constitute the functional (target protein binding) components of any one or several of the selected genus of antibodies, as well as the therapeutic use such compounds. These compounds include, but are not limited to, whole antibodies of the selected genus, antigen-binding fragments of antibodies of the selected genus, and chimeric or humanized manifestations of any antibody or antibody fragment derived from the selected genus of antibodies. Such derivations of the inventions may include, but are not limited to, truncated, linear, single-chained, an IgG fragment, a F(ab) fragment, a F(ab') fragment, a F(ab)2 fragment, a F(ab')2 fragment, an Fv fragment or an scFv fragment which may be manifested from any antibody of the selected genus.

The invention includes the result of any member of the antibody genus having its Fc region mutated at the 297 position to generate an aglycosylated antibody. The invention includes the results of any antibody of the selected genus being engineered to elicit reduced Fc-mediated effector functions. Methods of engineering may include, without limitation, amino acid mutations, amino acid additions or deletions, glycan modification or removal, pegylation, and/or truncation.

Methods of Administration

The invention provides methods of treatment comprising administering to a subject an effective amount of an embodiment of the selected genus of antibodies. The subject may be an animal (a mammal such as a cow, pig, rat, or monkey) but is preferably a human. Various delivery systems are known and can be used to administer an embodiment of the invention, (e.g., encapsulation in liposomes, microparticles, microcapsules, recombinant cells capable of expressing the compound, receptor-mediated endocytosis, construction of a nucleic acid as part of a retroviral or other vector, etc.) Methods of introduction can be enteral or parenteral and may include, but are not limited to, intradermal, intramuscular, intraperitoneal, intravenous, subcutaneous, intranasal, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. Administration can be acute or chronic (e.g. daily, weekly, monthly, etc.) or in combination with other agents.

Dosage

For the prevention or treatment of arthritis, the appropriate dosage of an active agent will depend on the type of arthritis to be treated, the severity and course of the disease, whether the agent is administered for preventive or therapeutic purposes, previous therapy, the patient's clinical history and response to the agent, and the professional judgment of the attending physician.

The agent is suitably administered to the patient at one time or over a series of treatments. The compounds of the present invention are administered to a mammal, preferably a human, in accord with known methods, such as intravenous administration as a bolus or by continuous infusion over a period of time, by intramuscular, intraperitoneal, intracerebrospinal, subcutaneous, intra-articular, intra synovial, intrathecal, oral, topical, or inhalation (intranasal, intrapulmonary) routes.

Formulation

The compound can be administered to an individual in a formulation with a pharmaceutically acceptable excipient(s). A wide variety of pharmaceutically acceptable excipients is known in the art and need not be discussed in detail herein.

The compound can be incorporated into a variety of formulations for therapeutic administration. In one example, a subject compound can be formulated into pharmaceutical compositions by combination with appropriate, pharmaceutically acceptable carriers or diluents, and can be formulated into preparations in solid, semi-solid, liquid or gaseous forms, such as tablets, capsules, powders, granules, ointments, solutions, suppositories, injections, inhalants and aerosols.

Dosing Schedule

A compound of the present invention can be administered to an individual with a certain frequency and for a period of time so as to achieve the desired therapeutic effect. For example, an antibody of the present invention can be administered, for example, once per month, twice per month, three times per month, every other week (qow), once per week (qw), twice per week (biw), three times per week (tiw), four times per week, five times per week, six times per week, every other day (qod), daily (qd), twice a day (qid), or three times a day (tid), or substantially continuously, or continuously, over a period of time ranging from about one day to about one week, from about two weeks to about four weeks, from about one month to about two months, from about two months to about four months, from about four months to about six months, or longer.

The selected antibodies can be used in a method for inhibiting AP activation in a subject afflicted with an inappropriate activation or over-activation of the AP system. The subject may be suffering from, or at risk for, any known arthritic condition. These include, but are not limited to; osteoarthritis, osteoporosis, acute gouty arthritis, spondyloarthropathy, polymyositis, dermatomyositis, ankylosing spondylitis, general arthritis, enthesitis-related arthritis, eosinophilic fasciitis, juvenile rheumatoid (idiopathic) arthritis, psoriatic arthritis, myositis and/or any other form of arthritic condition associated with alternative complement pathway activation.

The method is a unique way inhibiting the AP without inhibiting the CP. The method is also unique for its action on the AP with an action specifically targeted to the formation of AP C3 convertase.

The method prevents, with specificity, AP mediated formation of C3a, C3b, C5a, C5b-9, or sC5b-9. In so doing, the method provides a way or mean of inhibiting, with specificity, AP mediated activation of neutrophils, monocytes, platelets, basophils, and mast cells. The method also provides a means of inhibiting, with specificity, AP mediated formation of leukocyte-platelet and platelet-platelet aggregates.

The method can be used for inhibiting AP mediated activation of cells which are activated to produce pro-inflammatory molecules in response to signaling from products of the AP complement system. In so doing, the method can be used for inhibiting formation of TNF-α, neutrophil elastase, and IL-1, which are all pro-inflammatory molecules produced from cells which are activated by products of the AP.

The method can be used for inhibiting, reducing, and/or preventing alternative complement pathway mediated inflammation and the effect that inflammation has on any and all tissues effected by arthritis. This includes the tissues of the joints' components as well as all tissues immediately surrounding the joints.

The selected antibodies can also be used in a coating on a medical device intended to come in contact with human tissue, blood or fluids. The medical device may be without limitation an implantable device, stent, drug delivery vehicle, or dialysis tubing. The invention may also be used as part of a therapeutic kit, along with other medical aids, in treating arthritic conditions.

Administration of the selected genus of antibodies, and/or any functional derivations thereof, may be by any method known in the art. Such administration may be subcutaneous, intraarticular, intramuscular, intradermal, intraperitoneal, intravenous, intranasal, or via oral routes of administration. In one preferred embodiment, the antibody is administered by subcutaneous injection or intravenous injection. In a specific embodiment, the antibody is administered by subcutaneous injection.

In one embodiment, the amount of AP antibody administered is in a dosage range between 0.3 mg/kg to 30 mg/kg. In a more specific embodiment, the AP antibody is administered once a day in a range between 0.5 mg/kg to 10 mg/kg. In another embodiment, AP antibody is administered in a dosage range between 0.3 mg/kg to 30 mg/kg at least once a week. In yet another embodiment, AP antibody is administered in a dosage range between 0.3 mg/kg to 30 mg/kg at least once a month.

AP Specific Antibodies that Inhibit RA

Alternative Pathway in Whole Blood—Inflammation Model

There is direct link between C3a/C5a production and activation of neutrophils, monocytes, and platelets and release of a battery of inflammatory cytokines, proteases, and peroxides. In this model, whole blood from a healthy donor is subjected to AP activation via contact as a stimulus. Anaphylatoxin production, cellular activation and measurement of inflammatory cytokines were determined in the presence and absence of antibodies of the current invention.

In order to demonstrate the effect of the activation of the alternative pathway in vivo, an ex vivo whole blood inflammation model was used. This model produces effects similar to those exhibited by the cells involved in initiating and perpetuating the inflammatory response. The whole blood system contains the full array of complement proteins and cells responsible for carrying out the ultimate inflammatory response which is the end result of alternative pathway activation. The alternative pathway is triggered in whole blood by contact of the plasma with the artificial surfaces of the polypropylene tubing. Even a simple exposure of the plasma to air can trigger AP activation, and the resultant cellular activation and release of inflammatory mediators. In this model, blood circulation in an artificial system generates complement anaphylatoxins, activated cells, and inflammatory mediators such as TNF-α and IL-1. Multiplex analysis further indicated the production of cytokines such as VEGF, IL-1, IL-17, and several macrophage derived cytokines.

These effects in vitro can predict the disease outcome if elevated levels of such components are found in blood or local tissue levels.

Elevated levels of C3a, C5a, and sC5b-9 have been found in patients with RA. Presence of high levels of cytokines and infiltrated activated leukocytes along with the elevated levels of complement activation byproducts in local joints is predictive of inflammation and tissue damage. Based on the tubing loop model and the effect of various antibodies of the current invention, it is easy to conclude that these antibodies prevent AP activation, AP-induced cellular activation and production of cytokines in whole blood inflammation model. These features explicitly demonstrate that the model system can easily be used to depict the onset of inflammation in vivo.

Anti-C3b, Anti-Ba, Anti-Bb, and Anti-P antibodies have the potential to down regulate the formation of TNF-α and therefore prevent the onset and progression of the arthritic condition. The therapeutic value of a reduction of TNF-α in those afflicted with arthritis is a known phenomenon to those of ordinary skill in the art. However, as discussed previously, one skilled in the art cannot predict the outcome of using any given antibody against a given protein in the alternative pathway. Not all Anti-C3b antibodies will have a therapeutic effect. The same is true for Anti-Ba, Anti-Bb and Anti-P antibodies unless selected using the two step process. This invention only targets to reduce the disease induced TNF-α and not the basal levels of TNF-α required for host defense AP Specific Antibodies and Inflammation/Joint Destruction in Humans In addition to the process of developing the selected genus of antibodies, as well as the resultant genus of antibodies, the invention additionally consists of a method of treating arthritis disease and arthritic conditions, of all known causes of such diseases and conditions. The method comprises of administering to the afflicted subject a therapeutically effective amount of a compound which is either a member of the selected genus of antibodies, and/or has been derived from such an antibody and utilizes the same AP inhibiting properties as any antibody from the selected genus of antibodies. Such a compound, or compounds, would inhibit the AP processes which lead to the complement activated inflammation which are known to cause and/or perpetuate arthritis.

In one aspect, the method can include treating an inflammatory disorder or disease in a human with the selected antibodies. The inflammatory disease or disorder can be selected from the group comprising arthritis, rheumatoid arthritis, osteoarthritis, systemic lupus erythematosus, mixed connective tissue disease, or sepsis. The method can involve administering to the human an amount of an alternative pathway specific antibody that binds to an alternative pathway protein without decreasing the amount of an antigen present in the human. The antibody can also have reduced Fc effector functions, and can prevent cartilage, bone damage, inflammation, pannus tissue formation, or osteophyte formation in the human.

In another aspect, the inflammatory disorders or diseases that can be treated by the methods can include, but are not limited to, rheumatoid arthritis, osteoarthritis, juvenile arthritis, psoriatic arthritis, gouty arthritis septic arthritis, Lupus, gout, or ankylosing spondylitis. The methods of the present invention can be used to treat any other arthritic conditions.

In a further aspect, the methods described herein can be used to treat an inflammatory disorder, which can be induced in a human by physical damage to at least one tendon located within a joint of the human.

In another aspect, the methods described herein can be used to alleviate joint damage in the human through the administration of the Type-AP antibody to the human. The type of joint damage in the human that can be treated by the methods can include, but are not limited to, osteoarthritic joint damage, rheumatoid arthritis joint damage, inflammatory joint damage, acute joint damage, or chronic joint damage.

In yet another aspect, the methods can be used to alleviate joint inflammation in the human through the administration of the alternative pathway specific antibody to the human.

In one aspect, the methods can be used to alleviate cartilage damage in a human. The cartilage damage in the human can occur as a result of osteoarthritis or rheumatoid arthritis.

In another aspect, the methods can selectively inhibit the activation of the alternative pathway in a human. The Type-AP antibody can inhibit activation of the alternative pathway without affecting activation of the classical pathway or the amplification loop of the CP.

In another aspect, the alternative pathway specific antibody can be selected from the group comprising, but is not limited to, an anti-C3b antibody, and anti-Factor Ba antibody, an anti-Factor Bb antibody, anti-factor B antibody, an anti-Factor D antibody, or an anti-Properdin antibody.

In a further aspect, the alternative pathway protein that the alternative specific antibody of the present invention can bind to can be selected from the group comprising, but is not limited to, C3b, Factor B, Factor Ba, Factor Bb, Factor D, or Properdin.

In yet another aspect, the methods described herein can be used to prevent the formation of byproducts that can form as a result of activation of the alternative pathway in a human. In one example, the methods of the present invention can prevent the formation of anaphylatoxins. Anaphylatoxins can include, but are not limited to, C3a and C5a. In another example, the methods of the present invention can prevent the formation of C5b-9 or sC5b-9 (otherwise known as MAC). In a further example, the methods of the present invention can prevent the activation of neutrophils, macrophages, and platelets in a subject. In yet another example, the methods of the present invention can prevent the formation of cytokines. Cytokines can include, but are not limited to, IL-1 and TNF-α.

In one aspect, the alternative pathway specific antibody can be a monoclonal antibody, a polyclonal antibody, an aglycosylated antibody, or an antibody that has one or more mutations.

In another aspect, the alternative pathway specific antibody can be selected from the group including, but not limited to, human, humanized, recombinant, chimeric, de-immunized, truncated, aglycosylated, linear, single-chained, an IgG fragment, a F(ab) fragment, a F(ab') fragment, a F(ab)2 fragment, a F(ab')2 fragment, an Fv fragment or an scFv fragment.

In a further aspect, the alternative pathway specific antibody can be conjugated to an agent. In one example, the agent can be a synthetic organic molecule. In another example, the agent can (1) reduce the immunogenicity of the alternative pathway specific antibody when the agent and the antibody are conjugated in vivo, (2) increase the pharmacokinetic activity of the alternative pathway specific antibody when the agent and the antibody are conjugated in vivo, or (3) decrease the proteolysis of the alternative pathway specific antibody when the agent and the antibody are conjugated in vivo.

In one aspect, the alternative pathway specific antibody can be made from the serum of a human and/or the serum of a mammal.

In another aspect, the methods can include an alternative pathway specific antibody that can have a reduced effector function. Reduced effector functions can include, but are not limited to, reduced Fc binding, lack of Fc activation, an Fc region that contains mutations that prevent the Fc effector functions, or the prevention of activation of platelets and cells that bear Fc receptors.

In another aspect, an effective amount of the alternative pathway specific antibody can be administered to the subject. In one example, the alternative pathway specific antibody or antigen binding fragment thereof can be administered to the subject in a therapeutically effective amount. In another example, the alternative pathway specific antibody or antigen binding fragment thereof can be administered to the subject in a prophylactically effective amount. In a further example the alternative pathway specific antibody can be effective in a therapeutic setting in vivo or ex vivo. In yet another example, the alternative pathway specific antibody can be effective in a prophylactic setting in vivo or ex vivo.

In yet another aspect, the alternative pathway specific antibodies described herein can contain antigen binding regions termed as complementarity determining regions, or CDRs. In one example, the CDRs of the alternative pathway specific antibody can be present in a fusion protein. In another example, the CDRs of the alternative pathway specific antibody can be derived from a rabbit alternative pathway specific monoclonal antibody or a mouse alternative pathway specific monoclonal antibody. In a further example, the CDRs of the alternative pathway specific antibody can have greater than 50% homology to the native CDRs of the alternative pathway specific antibody.

In another aspect, the alternative pathway specific antibody can bind to the alternative pathway protein without reducing the levels of that protein in the human.

In one aspect, the methods can be used to treat joint instability in a subject using an alternative pathway specific antibody. In one example, the administration of the alternative pathway specific antibody can reduce joint instability in a human by preventing cartilage damage, bone damage, inflammation, or osteophyte formation in the human. In another example, the alternative pathway specific antibody can bind to an alternative pathway protein without decreasing the amount of an antigen in the human. In a further example, the antibody can also have reduced effector functions. The antibody can inhibit activation of the alternative pathway without affecting activation of the classical pathway.

In another aspect, the methods can be used to treat joint instability. In one example, the methods can be used to treat joint instability that results from a tendon, ligament, or tissue tear around the area of a joint of a human. In another example, the methods can be used to treat joint instability that result from the physical damage of tissue within a joint of a human, including, but not limited to, damage to the meniscus, tendons, and ligaments of the joint of a human. In a further example, the methods can be used to treat joint instability that results from a genetic cause or a physical cause in the human. In yet another example, the methods can be used to treat joint instability that results from cartilage loss, cartilage damage, bone damage, tissue inflammation, pannus tissue formation, or osteophyte formation in a human. In a further example, the methods of the present invention can be used to treat joint instability that results from excessive production of inflammatory cytokines within a joint of the human.

In a further aspect, the methods described herein can include administration of an alternative pathway specific antibody to a human to alleviate a joint disorder in a human. In one example, the methods of the present invention can include administration of an alternative pathway specific antibody to a human to alleviate joint pain in a human. In another example, the methods of the present invention can include administration of an alternative pathway specific antibody to a human to alleviate joint inflammation in a human.

Another aspect relates to a method of treating osteoarthritis in a human. The method can involve administering to the human an amount of an alternative pathway specific antibody that binds to an alternative pathway protein without decreasing the amount of an antigen present in the human. The antibody can also have reduced Fc effector functions, and can prevent cartilage, bone damage, inflammation, or osteophyte formation in the human. The antibody can inhibit activation of the alternative pathway without affecting activation of the classical pathway.

In another aspect, the method can be used for treating rheumatoid arthritis in a human. The method can involve administering to the human an amount of an alternative pathway specific antibody that binds to an alternative pathway protein without decreasing the amount of an antigen present in the human. The antibody can also have reduced Fc effector functions, and can prevent cartilage, bone damage, inflammation, or pannus tissue formation in the human. The antibody can inhibit activation of the alternative pathway without affecting activation of the classical pathway.

In another aspect, the method can be used for treating arthritis, osteoarthritis, rheumatoid arthritis, an autoimmune disease, or joint instability in a subject. The methods can provide for administering to the subject an effective amount of an alternative pathway specific antibody or antigen binding fragment thereof that binds to an alternative pathway protein and can selectively block activation of the alternative pathway in a subject. By treating arthritis, osteoarthritis, rheumatoid arthritis, an autoimmune disease, or joint instability, the methods of the present invention can improve joint mobility and can prevent cartilage damage, bone damage, osteophyte formation, and pannus tissue formation in a subject.

AP Specific Antibodies and Other Diseases

The selected genus of antibodies may be used to treat any disease, or disease condition, associated with inappropriate activation, or over activation, of the alternative pathway. Examples of alternative complement pathway associated disorders are numerous. The following is a list of some, but not all, of the diseases, and/or disease symptoms and conditions, which may be ameliorated through administration of the invention genus of antibodies.

Pathologies of the Auditory System—Ménière's disease [1], in which complement factors H and B are over-expressed Pathologies of the Cardiovascular System—Kawasaki's disease (arteritis) [2] Cardiac surgery complications [3] Henoch-Schonlein purpura nephritis [4], wherein studies suggest that generation of MAC may be involved in the pathogenesis of vascular injury in a significantly large number of skin lesions and of HSP nephritis, Vascular leakage syndrome [5] (associated with elevated c3a), Percutaneous coronary intervention (PCI)/coronary angioplasty [6], Ischemia-reperfusion following acute myocardial infarction [7, 8], Myocardial infarction [9], which elevates C3 and C4, Atherosclerosis [10], where C5a is present in atherosclerotic plaques, Immune complex vasculitis [11, 12], in which MAC alters the membrane integrity of endothelial cells, Arteritis [13], which contain C3 and C4 deposits, Aneurysm [14], where it has been shown that C5 inhibition attenuates injury in abdominal aortic aneurysm model, Cardiomyopathy [15], where c5b-9 activates TNF-α, vasculitis [16, 17], where it has been shown that C5−/− mice and factor B−/− mice do not develop disease, Takayasu's arteritis [18], Dilated cardiomyopathy [19], where c5b-9 activates TNF-α, Venous gas embolus (VGE) [20], Wegener's granulomatosis [21], Behcet's syndrome [22], Autoimmune cardiomyopathy [15, 23, 24], Balloon angioplasty [25], in which high levels of C5a are associated with restenosis, Myocarditis [26], where C3a and TNF-α are present, Percutaneous transluminal coronary angioplasty (PTCA) [6], IL-2 induced vascular leakage syndrome [5], Coronary artery disease (CAD) [27], where there are high C3 levels, Dressler's syndrome (postmyocardial infarction syndrome) [28], in which C3d levels are elevated, Giant cell arteritis (temporal or cranial arteritis) [29], Ischemic heart disease [30], Ischemia-reperfusion injury [8], which generates C3a and c5a, Leukocytoclastic vasculitis [31], in which c3d, g and Terminal complement complexes are present, Mesenteric artery reperfusion [32, 33], where it has been shown binding C3b attenuates injury, Microscopic polyangiitis [34], Pauci-immune vasculitis [35], associated with MAC, c3d, factor P, and factor B, Pulmonary vasculitis [36], Raynaud phenomenon [37], Post-ischemic reperfusion conditions [38], Pulmonary embolisms and infarcts [39], Restenosis following stent placement [40], Subacute bacterial endocarditis [41], where C3d is present Vasculitis associated with rheumatoid arthritis [42] and C3 deposits.

Pathologies of Connective Tissue—Mixed connective tissue disease [43] and Polymyalgia rheumatica [44], which C3 and C4 are deposited.

Pathologies of the Skin—Pemphigoid [45], Epidermolysis bullosa acquisita [46], in which Factor B deficient mice display delayed and less severe blistering in a disease model, Autoimmune bullous dermatoses [47], Bullous pemphigoid [45, 48], which is associated with C3 and C5, scleroderma [49], where c5b-9 and C5a receptors are activated, Angioedema [50], Hereditary angioneurotic edema (HAE) [51], Erythema multiforme [52], Herpes gestationis [53], Sjogren's syndrome [54], with activated c5b-9, Psoriasis [55, 56], Alopecia areata [57], Atopic dermatitis (eczema) [58], where levels of C3 and C4 are increased, Cicatricial pemphigoid [59], Dermatitis herpetiformis [60], Diffuse systemic sclerosis [61], Discoid lupus erythematosus [62], Eosinophilic spongiosis [63], Erythema nodosum [64], Lichen planus [60], Linear iga disease [65], Localized systemic sclerosis (morphea) [61], Mucha-Habermann disease [66], Occular cicatricial pemphigoid [59], Pemphigus [60], Pemphigus vulgaris [60], Pyoderma gangrenosum [67], Vitiligo [68] Urticaria [50].

Pathologies of the Endocrine System—Hashimoto's thyroiditis [69], Diabetes mellitus type 1[70], in which C3, c3d, and C4 levels are increased, Stress anxiety [71], Pancreatitis [72], Addison's disease [73], Insulin resistance [74], which increases factor H, Diabetic angiopathy [75] Graves' disease [76].

Conditions Associated with Extracorporeal Procedures—Post-cardiopulmonary bypass inflammation [77, 78], Heparin-induced extracorporeal LDL precipitation (HELP) [83], where C5a is increased, Postperfusion syndrome [84], Postoperative pulmonary dysfunction [86], Post-pump syndrome in cardiopulmonary bypass or renal bypass [87], which increases c5b-9, and complement activation during cardiopulmonary bypass operations [88], hemodialysis [79], cardiopulmonary bypass [77, 78], leukopheresis [80], plasmapheresis [81], plateletpheresis [82], and extracorporeal membrane oxygenation (ECMO) [85], which can activate SC5b-9 via alternative pathway.

Pathologies of the Gastrointestinal System—Crohn's disease [89], Celiac Disease/gluten-sensitive enteropathy [90], associated with c3b, Intestinal ischemia [91], Inflammatory bowel disease (IBD) [92], associated with c5a, Ulcerative colitis [93], where it has been shown a C5a antibody attenuates damage in colitis model, Eosinophilic gastroenteritis [94], Gastritis [95], where levels of c3b, ic3b, and C3c are increased Pancreatitis [72].

Hematologic Disorders—Catastrophic anti-phospholipid syndrome (CAPS) [96], Cold Agglutinin Disease (CAD) [97], which increases c3b, Thrombotic thrombocytopenic purpura (TTP) [98], which increases CD46, factor H, and factor I, Idiopathic thrombocytopenic purpura [99], where C3 and C4 detected are on platelets, Serum sickness [100], where abnormal factor H leads to increased glomerular C3 deposition, Endotoxemia [101], Sepsis [102], Atypical hemolytic uremic syndrome (ahus) [103], where there is enhanced formation of c3bbb convertase and resistance to complement regulators, Paroxysmal Nocturnal Hemoglobinuria (PNH) [104, 105], where it has been shown a C5 antibody treatment reduced thromboembolism risk, Septic shock [106], sickle cell anemia [107], which elevates c3b, Hypereosinophilic syndrome [108], which increases c5a, anti-phospholipid [109], Autoimmune lymphoproliferative syndrome [110], Dego's disease [111], where c5b-9 is activated, Evan's syndrome [112], essential mixed cryoglobulinemia [113], and pure red cell aplasia [114].

Pathologies of the Hepatic System—Autoimmune chronic active hepatitis [115, 116], which increase c3d, Infectious hepatitis [117], Primary biliary cirrhosis inflammation (PBC) [118], associated with higher c1q, C3, factor B, and properdin levels, Primary sclerosing cholangitis [119, 120], where C3 is increased Autoimmune hepatitis [121].

Pathologies of Hypersensitivity—Anaphylactic shock [122], in which blocking C3a and C5a has shown to be effective therapy, Anaphylactoid reactions from use of radiographic contrast media [123, 124], adverse drug reaction [125], Allergy [126].

Pathologies of the Musculoskeletal System—Osteoarthritis [127], Osteoporosis [128], Acute gouty arthritis [129], where C6 and MAC are activated, Spondyloarthropathy [130], Polymyositis [131], Dermatomyositis [131, 132], which increases C3b and c5b-C9, Ankylosing spondylitis [133], associated with increased c3b, Arthritis [10], where C5a levels rise, Enthesitis-related arthritis [134], Eosinophilic fasciitis [135], Juvenile rheumatoid (idiopathic) arthritis [136], with increased c1q, C4, and MAC, Myositis [137], Psoriatic arthritis [138], where it has been shown that anti-C5a prevents arthritis, Reiter's syndrome (reactive arthritis) [139] Relapsing polychondritis [140].

Pathologies of the Nervous System—Myasthenia gravis [141], Multiple sclerosis (MS) [142], Guillain Barre syndrome [143], which activates C3a and c5a, stroke [144], where C4 and scc3b-5 is elevated, Cranial nerve damage in meningitis, Variant Creutzfeldt-Jakob disease (vcjd) [145, 146], Neuropathic pain [147-149], Alzheimer's disease (AD) [150], where it has been shown that treatment with C5a receptor antagonist reduced pathology, Multifocal motor neuropathy (MMN) [151, 152], Huntington's disease (HD) [153] where there is deposition of C3 and C9 and upregulation of C5a receptors, Amyotrophic lateral sclerosis (ALS) [154, 155], which increases C5a and c5a, Parkinson's disease [156, 157], degenerative disc disease (DDD) [131, 132], Idiopathic polyneuropathy [158, 159], allergic neuritis [160-163], where C3 depletion can result in less injury, Acute disseminated encephalomyelitis [164], Acute hemorrhagic leukoencephalitis [165], Autoimmune peripheral neuropathy [166], Chronic inflammatory demyelinating polyneuropathy [167], demyelination [168], where reduction in C3 and C4 has shown to prevent demyelination, Idiopathic inflammatory demyelinating diseases [169], Lambert-Eaton myasthenic syndrome [170], Meningitis [171], in which C5a is correlated with prognosis and c5ar deficient mice suffered less brain damage, Miller-Fisher syndrome [172], Neuromyelitis optica (NMO) [173], Perivenous encephalomyelitis [174], where it has been shown C6 deficient mice are unable to form MAC and exhibit no demyelination, progressive inflammatory neuropathy [175], opsoclonus myoclonus syndrome [176], Rasmussen's encephalitis [177], pediatric autoimmune neuropsychiatric disorders associated with streptococcus [178], stiff person syndrome [179], Susac syndrome [180] anxiety [181].

Pathologies of Vision—Endophthalmitis [182], where there is higher levels of C3a and C4a in the vitreous, Diabetic retinopathy [183], where there are C3d and c5b-9 deposits in choriocapillaris, Diabetic retinal microangiopathy [184], with C5b-9 in the retina, Histoplasmosis of the eye [185], Purtscher's retinopathy [186], Age-related macular degeneration (AMD) [187, 188], Dry Age-Related Macular Degeneration (AMD) [189], with elevated c3a, choroidal neurovascularization (CNV) [190, 191], Uveitis [192], Diabetic macular edema [192], Pathological myopia, Central retinal vein occlusion (CRVO) [193], Retinal neovascularization, Retinal pigment epithelium (RPE) [194], Choroidal neovascularization (CNY) [190, 191], Dominant drusen [195], where C3a and C5a promote coronial neurovasculization, Photoreceptor and/or Retinal Pigmented Epithelial (RPE) loss [196], Stargardt's disease [197] Scleritis [198].

Oncological Pathologies—Hemangiomas [199], Tumor cell metastasis [200].

Pathologies of the Renal System—Glomerulonephritis [17], Poststreptococcal glomerulonephritis (PSGN) [201-203], Goodpasture's disease [204, 205], Membranous nephritis [206, 207], Berger's Disease/iga nephropathy [208, 209], Mesangioproliferative glomerulonephritis [210], where c5b-9 is elevated, Membranoproliferative glomerulonephritis (Dense Deposit Disease) [211, 212], Membranous glomerulonephritis [213-215], Renal cortical necrosis (RCN), Renal reperfusion injury [216-220], where it has been shown C5 inhibition protects from renal injury, Cryoglobulinemic glomerulonephritis [221], ABO Incompatible Renal Transplant [222], Atypical hemolytic uremic syndrome (ahus) [103], Lupus (SLE) nephritis [223]

Pathologies of the Respiratory System—Eosinophilic pneumonia [224], Hypersensitivity pneumonitis [225], Bronchiecstasis [226], Reactive airway disease syndrome [227], where it has been shown C5 and c5ar deficient mice show no airway hyperreactivity, Respiratory syncytial virus (RSV) infection [228-230], Parainfluenza virus infection [231], Rhinovirus infection, Adenovirus infection [232], Allergic bronchopulmonary aspergillosis (ABPA) [233, 234], Tuberculosis [235, 236], Parasitic lung disease [237], Pollution-induced asthma [238, 239], in which higher C3c and C4 in serum has been shown in children living in polluted areas, Airway hyperresponsiveness (AHR) [233, 234], Adult respiratory distress syndrome [240-242], which elevates C3 and c3a, Exercise-induced asthma [243, 244], Cough variant asthma, occupational asthma [245], Allergic asthma [246, 247], Pollen-induced asthma [248, 249], Severe asthma [250], Chronic obstructive pulmonary disease (COPD) [251, 252], Emphysema [253], bronchitis [253, 254], Cystic fibrosis [255], Interstitial lung disease [256], Acute respiratory distress syndrome (ARDS) [240-242], Transfusion-related acute lung injury (TRALI) [257, 258], Acute lung injury [259, 260], Byssinosis [261, 262], Asbestos-induced inflammation [263], Bronchoconstriction [264], Fibrosing alveolitis (idiopathic pulmonary fibrosis) [265, 266], which elevates factor Ba, Ischemia/reperfusion acute lung injury [32, 33], Organic dust diseases [267, 268], where C3, c3d, and factor B levels increase, Pneumonia [269], Pathologies caused by inert dusts and minerals (e.g., silicon, coal dust, beryllium, and asbestos) [270].

Systemic Disorders—Systemic lupus erythematosis (SLE) [271-273], Rheumatoid arthritis [274, 275], Acquired Immune Deficiency Syndrome (AIDS) [276-281], Sarcoid [282, 283], Systemic inflammatory response syndrome (SIRS) [284-286], Systemic juvenile rheumatoid arthritis [287], which elevates Factor Bb and SC5b-9, Castleman's disease [288], Complement component 2 deficiency [289], Multiple organ failure [290], Interleukin-2 induced toxicity during IL-2 therapy [5, 51], Barraquer-Simons Syndrome (acquired partial lipodystrophy) [121].

Complications of Organ and Tissue Transplants—Transplant rejection [291-295], where it has been shown anti-C5 antibodies improved graft survival, Xenograft rejection [296-298], Allotransplantation of organs or grafts [299], where it has been shown C5 inhibition reduces antibody mediated rejection, Hyperacute rejection [300-302], Graft versus host disease [303-309], Hyperacute allograft rejection [310], Presensitized Renal Transplant—Living Donor [311], Revascularization to transplants and/or replants [312].

Associated with Trauma—Hemorrhagic shock [313], where it has been shown C5a receptor antagonist attenuates multiple organ injury, Hypovolemic shock [314], Spinal cord injury [129, 315-318], Cerebral trauma and/or hemorrhage [319], Severe burns [320, 321], where it has been shown C5a blockade improves burn-induced cardiac dysfunction, Frostbite [322], Crush injury [323-326], Wound healing [327], Brain trauma [319, 328, 329], Cerebral ischemia reperfusion [8, 330], which elevates C5 Smoke injury [331].

Pathologies of the Urogenital and/or Reproductive System—Spontaneous abortion [238], Sensory bladder disease [332], Interstitial cystitis (painful bladder syndrome) [333-335], Fetomaternal tolerance [336-338], Preeclampsia [339, 340], Sinusitis [341, 342], Complications of pregnancy [343], Chronic abacterial cystitis [332], Hemolysis, elevated liver enzymes, and low platelets (HELLP) syndrome [344], Infertility [345], Placental dysfunction and miscarriage and pre-eclampsia [346], Recurrent fetal loss [347].

Other relevant diseases and conditions—Agammaglobulinemia [348], antisynthetase syndrome [349], atopic allergy [350], autoimmune enteropathy [351], autoimmune inner ear disease [352], autoimmune polyendocrine syndrome type 1 (Whitaker's syndrome) [353], autoimmune polyendocrine syndrome type 2 (Schmidt syndrome) [353], autoimmune progesterone dermatitis [354], Balo disease/Balo concentric sclerosis [355], Vitelliform macular dystrophy (best disease) [356], Bickerstaff's encephalitis [357], Blau syndrome [358], Cancer [359], chemical injury (due to irritant gasses and chemicals, e.g., chlorine, phosgene, sulfur dioxide, hydrogen sulfide, nitrogen dioxide, ammonia, and hydrochloric acid) [360], chronic recurrent multifocal osteomyelitis [361], Churg-Strauss syndrome [362], Cogan syndrome [352], corneal neovascularization [363], Cushing's syndrome [364], cutaneous leukocytoclastic angiitis [365], Dercum's disease [366], fibrodysplasia ossificans progressiva [367], fibrogenic dust diseases [368], gastrointestinal pemphigoid [369], Hashimoto's encephalitis [370], hemolytic uremic syndrome (HUS) [371], hemoptysis [372], hypogammaglobulinemia [373], immune complex-associated inflammation [374], ischemia-related retinopathies [375], lichen sclerosus [376], lupoid hepatitis [377], juvenile lymphocytic thyroiditis [378], Majeed syndrome [379], malattia leventinese (radial drusen) [380], neuromyotonia [381], North Carolina macular dystrophy [382], ord's thyroiditis [383], palindromic rheumatism [384], paraneoplastic cerebellar degeneration [385], parasitic diseases [386], Parry Romberg syndrome [387], pars planitis [388], Parsonage-Turner syndrome [389], pattern dystrophy [390], pernicious anaemia [391], POEMS syndrome [392], polyarteritis nodosa [393], proliferative nephritis [394], restless leg syndrome [395], retroperitoneal fibrosis [396], rheumatic fever [397], rotational atherectomy [398], Schnitzler syndrome [399], Sorsby's fundus dystrophy [380], Still's disease [400], Surgical trauma [401], Sydenham chorea [402], sympathetic ophthalmia [403], Tolosa-Hunt syndrome [404], transverse myelitis [405], undifferentiated spondyloarthropathy [406], vasculitis associated with systemic lupus erythematosus [407], vasculitis associated with hepatitis A[377], von Hippel-Lindau disease (VHL) [408], Whipple's disease [409], Autoimmune Neutropenia [410], Chemotherapy [411], Hemodialysis [412], Human Immunodeficiency Virus (HIV) [413], Malaria [414], Epstein Barr Virus [415], Vitamin Deficiencies [416], Hypersplenism [417], Idiopathic Thrombocytopenic Purpura (ITP) [418], Disseminated Intravascular Coagulation (DIC) [419], Post-Transfusion Purpura [420], Neonatal Allo-Immune Thrombocytopenia [421], Onyalai [422], Cyclic Neutropenia [423], Snake bites [424], Administration of Interferon [425], Administration of Tumor Necrosis Factor [426], administration of Radiotherapy [427], and application of Corticosteroids [428].

EXAMPLE 1

Predicted & Proposed Schematics for the Selection of Antibodies that do not inhibit the CP or the Classical Pathway Triggered Activation of the Alternative Pathway. (See FIG. 1)

Shown in FIG. 2 are the three typical assays that can be used, in combination, to confirm the selected genus of antibodies.

In FIG. 2, the graph under Assay 1 represents the profile typical of an antibody or antibodies which would inhibit the classical pathway. Assay 1 uses 1% normal human serum and antibody sensitized sheep red blood cells to allow for the activation of the classical pathway. Compounds that inhibit the classical pathway would be identified using such an assay. Such antibodies will be positive in Assay 1, but not necessarily positive in Assay 2 and/or Assay 3. (+/−/−).

In FIG. 2, Assay 2, consists of antibody sensitized sheep RBCs are incubated in 10% normal human serum in the presence of Ca/Mg buffer. In this situation, compounds that inhibit the amplification loop of the classical pathway will be identified. These compounds will affect the activity of the classical pathway. Such compounds would inhibit the alternative pathway in isolation (such as would exist in a Mg2+ only buffer). However, if the nature of the compounds is to participate in both the classical and alternative pathway, they would not be considered alternative pathway specific antibodies. Such antibodies will show a positive response in both Assay 2 and Assay 3 (−/+/+). Such antibodies have been patented in previous inventions.

FIG. 3 shows the profile of antibodies that exclusively inhibit the AP without inhibiting the classical pathway to any degree. The selected genus of antibodies does not impact any degree of amplification of the CP which may or may not, under normal circumstances, be a contribution of the AP. Rather, the selected genus of antibodies has no impact at all on the CP at all. If the AP plays any role in the amplification of the CP, this particular effect is not interrupted by the selected genus of antibodies. In these assays, the selected genus of antibodies will show, by definition, a negative result in Assay 1 and Assay 2, but a positive result in Assay 3. (−/−/+).

FIG. 4 shows the data generated with the antibodies of the current invention. These antibodies inhibit the AP but not the CP in 1% or 10% normal human serum as shown. Panel A shows the control and antibody treated data sets in 1% normal human serum in CP buffer. Panel B shows the control and antibody treated data sets in 10% normal human serum and panel C shows the data sets in 10% AP buffer.

The AP selective antibodies are the focus of this invention. Based on the hemolysis data it is easy to conclude that such antibodies inhibit the formation of functional C5b-9, which is responsible for cell lysis. These assays will identify anti-P, anti-Ba, anti-Bb, anti-C3b, anti-C5b, anti-C6, anti-C7, anti-C8, and anti-C9 antibodies that exclusively inhibit the AP.

Step 2 of The Screening Method is to inhibit the formation of alternative pathway dependent C3b ("aC3b"). Both pathways result in the formation of C3b. However, it is aC3b that is important for the present invention. The assay of Step 2 will evaluate the inhibition of aC3b formation. The selected antibodies from Step 1 of The Screening Method are screened through the C3b formation assays in order to identify those that inhibit the formation of C3b. It is expected that anti-P, anti-C3b, anti-Ba, and anti-Bb will inhibit C3b formation in normal human serum. Such antibodies are AP selective.

The two step process of identification is used to identify antibodies that are AP selective.

EXAMPLE 2

Cellular Assay to Demonstrate Inhibition of AP Activation in a Subject using Exemplary Compounds of the Invention Genus of Antibodies To assess the ability of the exemplary compounds of the present invention to inhibit AP activation in a in vivo-like system, an erythrocyte hemolysis assay was used. Rabbit red blood cells (rRBCs) were incubated with normal human serum (NHS) in an AP enabling buffer. The presence of rRBCs ("the foreign body") preferentially induces activation of the AP, resulting in C5b-9 deposition on the erythrocytes and ultimately causing cell lysis. The extent of cell lysis is detected based on light scattering at optical density of 700 nm. Exemplary compounds of the invention genus of antibodies inhibited hemolysis of rRBCs in a dose dependent manner, as shown in FIG. 3.

Introducing rabbit Erythrocytes (rRBC) into 10% human serum (with Mg2+/EGTA) represent the introduction of a foreign cell surface which initiates the alternative complement cascade. Activation of the AP results in the formation of MAC which causes lysis of the foreign cells (the rRBCs). The selected antibodies of the present invention prevent lysis of these erythrocytes. This process was quantified after examining the light scattering caused by intact red blood cells.

It is well established that rabbit erythrocytes specifically activate the AP, with a resulting lysis of the rRBCs by the C5b-9 (MAC) complex. A progressive decrease in light scatter (due to lysis of intact cells) was measured at 700 nm as a function of time in a temperature-controlled ELISA plate reader. The data were recorded and analyzed with a SpectraMax 190 plate reader and SoftMax Pro software. The results were plotted with MicroCal Origin Software.

As shown in FIG. 4, anti-C3b, anti-Ba, anti-Bb, and anti-P antibodies of the present invention inhibit AP activation and therefore lysis of rRBC in human serum only under conditions that promotes alternative pathway dependent lysis.

Lysis of cells occurs in several diseases including hemolytic diseases. Inhibition of lysis would provide significant benefit in disease conditions where cell death occurs as a result of production of C5b-9 (FIG. 4, Panel C). Lysis of cells also is indicative of tissue injury seen in "OTHER DISEASES" where role of complement in tissue injury appears to be well established.

EXAMPLE 3

The Antibody of the Present Invention does not Inhibit the Classical Pathway

To test the activity of the antibodies for CP inhibition, antibody-sensitized, sheep erythrocytes (sRBC) were incubated in 1% normal human serum in CP buffer (Ca2+/Mg2+). These sRBCs activate the CP, which induces lysis of cell membranes. Lysis of the cell membranes results in a gradual decrease in light scattered by cells. When an alternative pathway specific antibody of the present invention was incubated with sRBCs at 37° C. in 1% NHS with a buffer containing Ca2+ and Mg2+ ("the CP buffer") no effect on hemolysis was observed within the time period beginning with the start of hemolysis and concluding with maximal hemolysis. This implies that the alternative pathway specific antibody of the present invention does not affect CP hemolytic activity in NHS (FIG. 4, Panels A & B) and is not expected to compromise the CP's expected contribution to host defense against pathogens.

Monoclonal antibodies of the present invention, irrespective of the target antigen against which they have been raised, do not inhibit the classical pathway. In a typical assay, antibody sensitized sheep erythrocytes are incubated with Normal Human Serum, with CP buffer containing Ca++. These conditions allow for selective activation of the classical pathway. Mechanistically, the antigen-Antibody complex on the surface of the sheep cells activates the classical complement pathway which causes erythrocyte lysis.

As shown in FIG. 4, the one representative antibody of the present invention that inhibits the AP but not the CP or the CP amplification loop. Development of monoclonal antibodies of this invention will leave the classical pathway intact for host defense against infection.

Lack of inhibition of CP activation by the antibodies of the current genus suggests that host defense will not be compromised as classical pathway is required for host defense. Classical pathway, upon activation, generates C3b which is required for opsonization. In a disease state during AP activation. Thus critical C3b mediated opsonization is no inhibited by the antibody of this invention.

EXAMPLE 4

The Antibody of the Present Invention does not Inhibit the Amplification Process Required for the Full Potential of the Classical Pathway A specifically designed assay was used in order to test candidate antibodies for any inhibitory effect on any amplification process which may affect the full potential of the Classical Pathway. In this assay, antibody-sensitized sheep erythrocytes (sRBC) were incubated in 10% normal human serum in CP buffer (Ca2+/Mg2+) These sRBCs activate the CP via an antibody-antigen bond complex, which induces lysis of cell membranes. Lysis of cell membranes results in a gradual decrease in light scattered by intact cells. When the alternative pathway specific antibody of the present invention was incubated with sRBCs at 37° C. in Ca2+ and Mg2+ containing buffer ("the CP buffer") in 10% normal human serum (NHS), no effect on hemolysis was observed (FIG. 4 Panel B) within the time period beginning with the start of hemolysis and concluding with maximal hemolysis. This implies that the alternative pathway specific antibody of the present invention does not affect CP hemolytic activity in NHS and is not expected to compromise the CP's expected contribution to host defense against pathogens. It also implies that the alternative pathway specific antibodies of the present invention do not affect any amplification process which may be required for the full potential of the CP. Accordingly, antibodies of the invention genus are not expected to compromise the CP's full contribution to normal host defense to pathogens.

Monoclonal antibodies of the present invention were evaluated for their effect on the on amplification of the alternative pathway. This was done using an assay of normal human serum (10% NHS with AP isolating Mg2+ only buffer) at 37 degree C. with a fixed number of rabbit erythrocytes (Covance) in a temperature controlled ELISA plate reader capable of reading at 700 nm. A progressive decrease in light scatter (due to lysis of intact cells) was measured at 700 nm as a function of time. The data were recorded and analyzed with a SpectraMax 190 plate reader and SoftMax Pro software.

As shown in FIG. 4, the alternative pathway specific antibody of the present invention does not inhibit amplification of the CP which might be initiated by the AP amplification loop. The antibody of the present invention does not inhibit the CP amplification loop (also called an amplification loop) and therefore is a specific inhibitor of the AP. Host defense will remain intact.

EXAMPLE 5

The Antibody of the Present Invention Inhibits C3b Formation in AP Buffer in 10% NHS Alternative pathway activation generates C3b via the cleaving of C3 by AP C3 convertase. C3 is thereby split into C3b and C3a. Antibodies were evaluated for inhibition of C3b using LPS to activate the Alternative Pathway. Microtiter plates were coated with LPS (Lipopolysaccharide from *Salmonella Typhosa*) 2 µg/50 µl in PBS overnight. The wells were incubated with 1% BSA in PBS to block the unoccupied sites on the plate. Following 2 hour incubation at room temperature, the plate was rinsed with PBS and incubated with Normal human serum (10% final concentration in AP buffer) was mixed with antibodies of the invention and incubated with LPS coated wells. The plate was again incubated for 2 hours 37° C. to allow C3b formation to occur. The plates were extensively washed with PBS, and components of the C3 convertase were detected appropriately with antibodies. We detected C3b with rabbit anti-human C3c at 1:2000 in blocking solution. Following incubation, the plates were rinsed with PBS and prepared with peroxidase labeled goat anti-rabbit at 1:2000 in blocking solution for C3b detection. All plates were developed with TMB following extensive washing with PBS. In the presence of an AP specific antibody of the present invention inhibition of C3b formation was observed.

As shown in FIG. 8, the alternative pathway specific antibodies of the present invention inhibit formation of C3b produced in excess via the alternative complement pathway. C3b coated cells are generally destroyed via what is known as extravascular hemolysis in PNH disease. Other nucleated cells can be removed as well via the same mechanism. Thus neutropenia, leokopenia and thrombocytopenia are some examples where the end result is the reduction in the number of cells. The genus of antibodies selected in the current application is expected to prevent the formation of C3b responsible for removal of cells via extravascular route. Extravascular lysis is important in indications such as paroxysmal nocturnal hemoglobinuria where C3b coated erythrocytes are removed from circulation via the unwanted extravascular route.

EXAMPLE 6

Inhibition of Formation of Inflammatory Mediators in Whole Blood Inflammation Model by Compounds (Antibodies of the Current Genus).

Alternative pathway activation generates C3b, which is cleaved from C3 by AP C3 convertase. C3 is cleaved into C3b and C3a. Inhibition of aC3b formation has been addressed in Example 5. Formation of C3a is measured using an ELISA (Quidel Corp). Antibodies of the present invention inhibit the formation of C3a. C3a receptors, which bind C3a, are found on monocytes. C3a is known to activate monocyte which release TNF-α, a potent inflammatory cytokine and an inflammatory mediator. TNF-α plays a role in the development and progression of arthritis. Anti-TNF-α therapies alone have provided significant, though incomplete, benefits for patients with various arthritic conditions and diseases, including rheumatoid arthritis and osteoarthritis. Inhibition of C3a formation is directly linked to the inhibition of monocyte activation and inhibition of TNF-α formation and arthritis inflammation.

AP activation in whole blood replicates conditions that are primary to disease induction and progression. Blood inflammation is linked to AP activation and production of inflammatory cytokines. When whole human blood is subjected to AP activation via an artificial trigger, inflammation in whole blood forwards to completion. This includes the formation of anaphylatoxins (e.g., C3a, C5a), the MAC complex (C5b-9/sC5b-9), activation of pro-inflammatory cells such as neutrophils, monocytes and platelets, and formation and release of pro-inflammatory cytokines including TNF-α, IL-1β, IL-6, IL-8, and IL-17.

In this blood inflammation (BI) model, a 2 mL aliquot of freshly isolated heparinized human blood was circulated in polyvinyl chloride tubing at 37° C. for 2 hours. Blood samples following the tubing loop rotation were evaluated for C3a, C5a, and C5b-9/sC5b-9 formation. Additionally inflammation markers such as TNF-α and neutrophil elastase were also measured.

The results shown in FIG. 10 demonstrate that antibodies of the invention inhibit C3a formation. Elevated levels of C3a have been found in several diseases where significant pathology exists. Excessive C3a production results in excessive monocyte activation and a progressively severe pathology. Many diseases where C3a is found elevated can be treated with the antibodies of this invention. Inhibition of C3a suggests inhibition of monocytes activation and inhibition of inflammation in vivo. Thus ex vivo assays are relective of in vivo inflammation which occurs in "OTHER DISEASES".

Results shown in FIG. 11 demonstrate that antibodies of the invention inhibit C5a formation. C5a activates neutrophils and monocytes by binding their respective receptors on each of these cell types. Activated neutrophils express CD11b and release elastase and are responsible for edema in several models of inflammation. As shown in FIG. 11, the alternative pathway specific antibodies of the present invention inhibit neutrophil activation and, consequently, neutrophil mediated pathological outcomes in vivo. As shown in FIG. 19-25 inhibition of AP activation prevents tissue inflammation, synovitis, bone and cartilage degradation.

Figure 18:
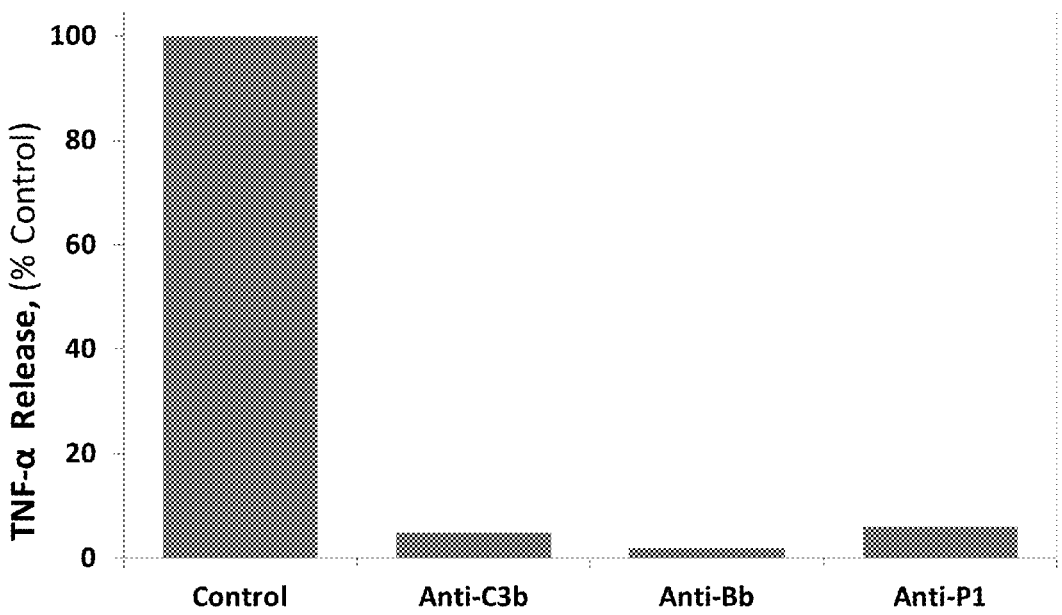
FIG. 18 illustrates a graph showing that the selected antibodies inhibit TNF-a release in Whole Blood Inflammation, which is functional correlate of monocyte activation.

The control bar in FIG. 18 shows the elevation in TNF-α, among other cytokines, that results from activation of neutrophils and monocytes. FIG. 18 also shows that antibodies of the current invention prevent the formation of TNF-α in disease conditions where elevated levels of TNF-α cause disease pathology.

The blood inflammation model exhibits features similar to those of in vivo diseases. Thus, the experiment predicts that disease outcomes will be improved with treatment utilizing antibodies of the current invention. When blood comes in contact with the foreign surfaces alternative pathway is activated which produces C3a, C5a, C5b-9, and sC5b-9. These molecules activate a variety of cells and cause the cells to release inflammatory mediators such as TNF, IL-1, VEGF, IL-8, and IL-17. The blood in vivo and in ex vivo condition is similar in generating symptoms that can lead to a full blown inflammatory response. Complement activators, AP products, AP-activated cells, inflammatory cytokines are present in disease state in vivo and can be produced in ex vivo in whole blood. Inhibition of cytokine production is important for down regulating/inhibiting the disease process as shown in FIGS. 19-22.

EXAMPLE 7

C3a/Monocyte/TNF-α and Arthritis

There is a direct correlation between TNF-α production and arthritis. The FDA has approved several anti-TNF-α antibodies that neutralize TNF-α and reduce inflammatory response that is the ultimate cause of the arthritic condition. These anti-TNF-α antibodies have been used for the treatment of arthritis in humans. Given that these anti-TNF-α antibodies have already proved successful in the treatment of arthritis, one can logically conclude that the invention genus of antibodies, which inhibit production of TNF-α by inhibiting the AP and all its products, will also be successful.

a) Rabbit Model of Arthritis

As predicted by this hypothesis, the compounds of the present invention inhibit AP activation, formation of TNF-α, and reduce inflammation and joint destruction in a rabbit model of arthritis. Accordingly, we can expect compounds that prevent TNF-α release to have important clinical significance in the treatment of human arthritis as well.

To evaluate the effect of the antibodies of the current invention, a rabbit arthritis model was used. In this model, arthritis was induced using the mBSA method described in literature which is readily accessible to those skilled in the art. This model possesses the key features of the arthritic disease condition, especially with regards to inflammation and expected changes in joint morphology, cartilage destruction, synovitis, pannus formation, and bone erosion.

Figure 19:
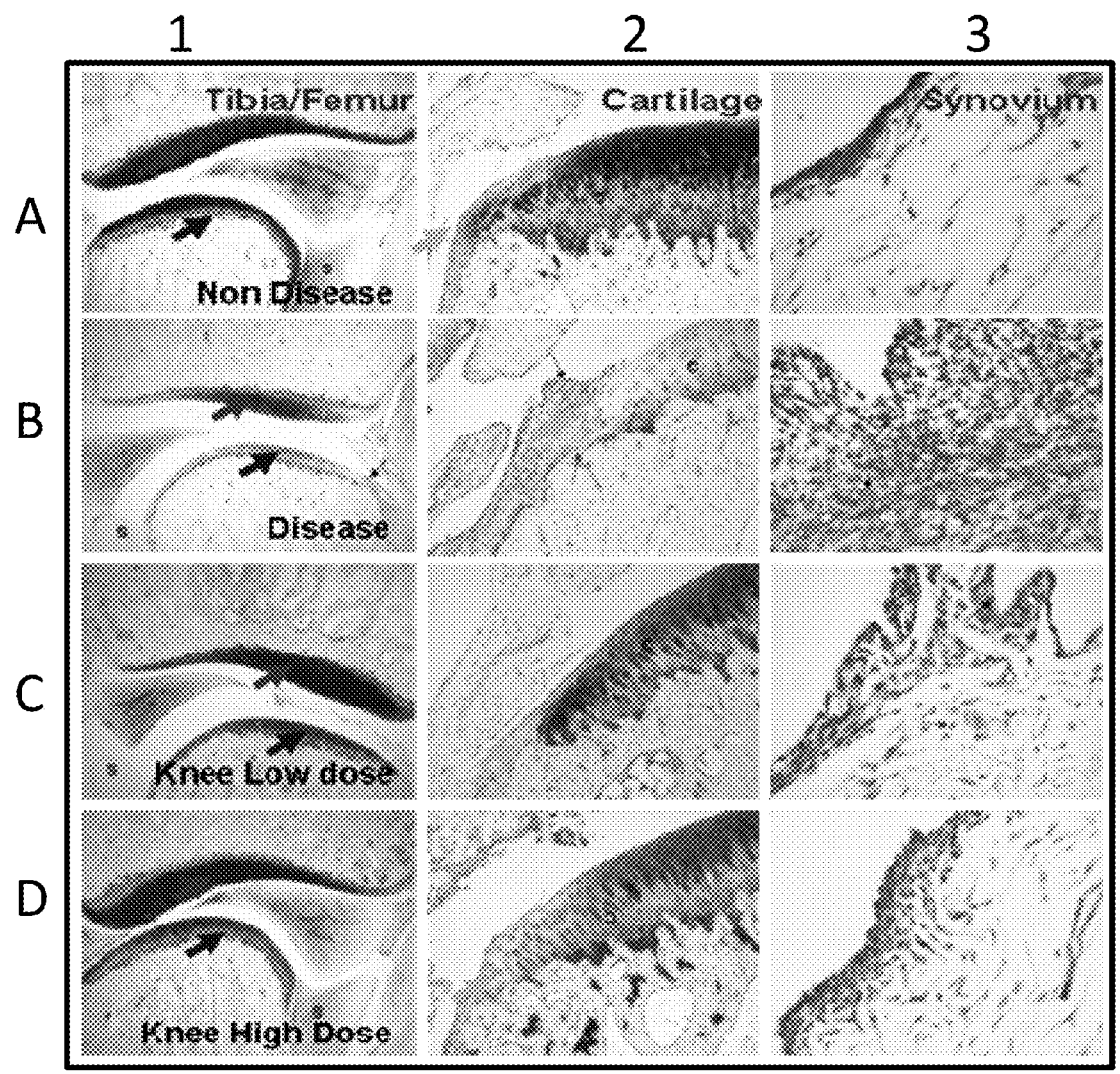
FIG. 19 illustrates images showing histological assessment of a knee section (Femur-Tibia joint) from rabbits having rheumatoid arthritis treated with an intra-articular dose of an anti-P antibody. The top row (A) shows the normal knee with the joint showing Tibia/femur. A2 shows cartilage on the Femur and A3 shows the synovial membrane within the pannus region in healthy rabbits. Row B is from a disease rabbit showing pannus in B2 and synovitis in B3. Rows C and D show treated rabbits at two different doses of the drug. C and D in column 3 show decreased infiltration of neutrophils and inflammatory cells. C2/D2 show reduced cartilage loss
Figure 20:
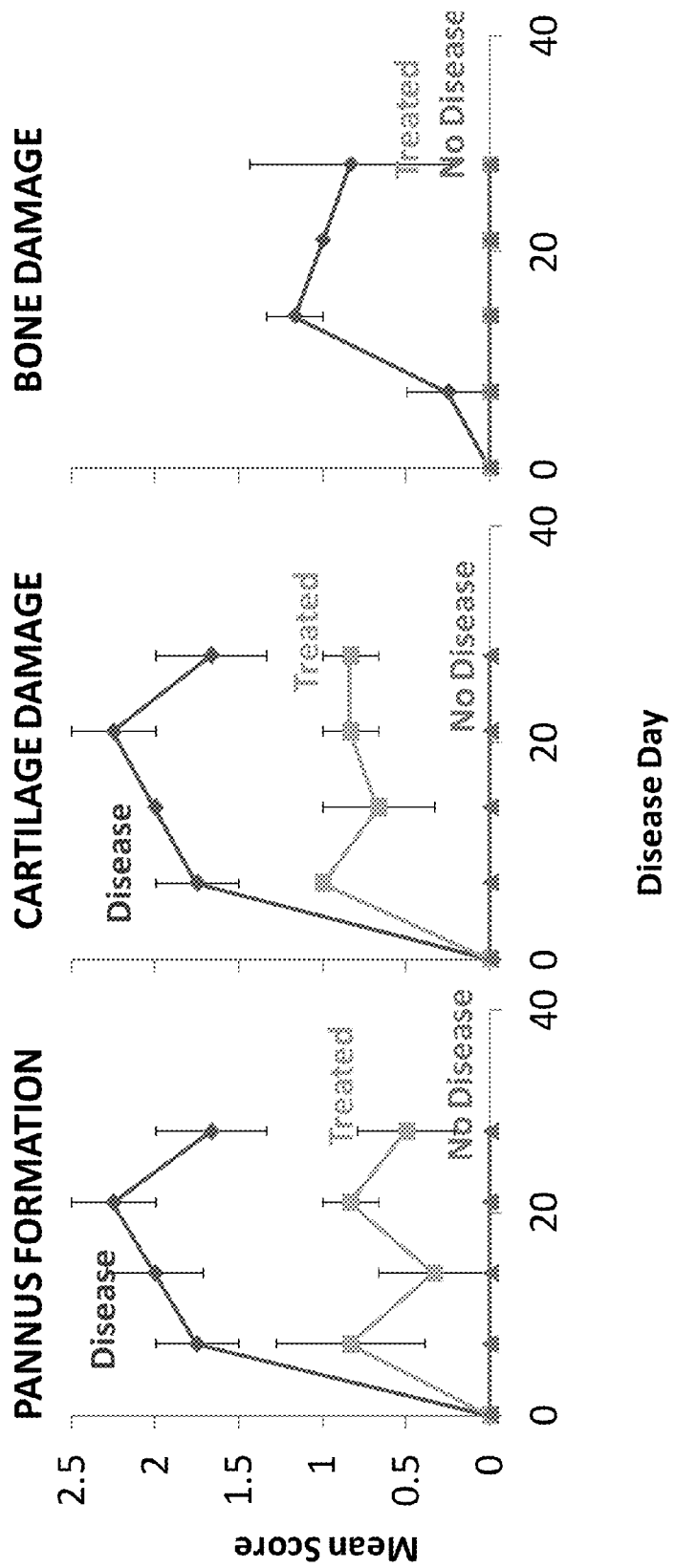
FIG. 20 illustrates graphs showing inhibition of pannus formation, cartilage damage, and bone damage in model of arthritis in rabbit by Anti-P antibody.
Figure 21:
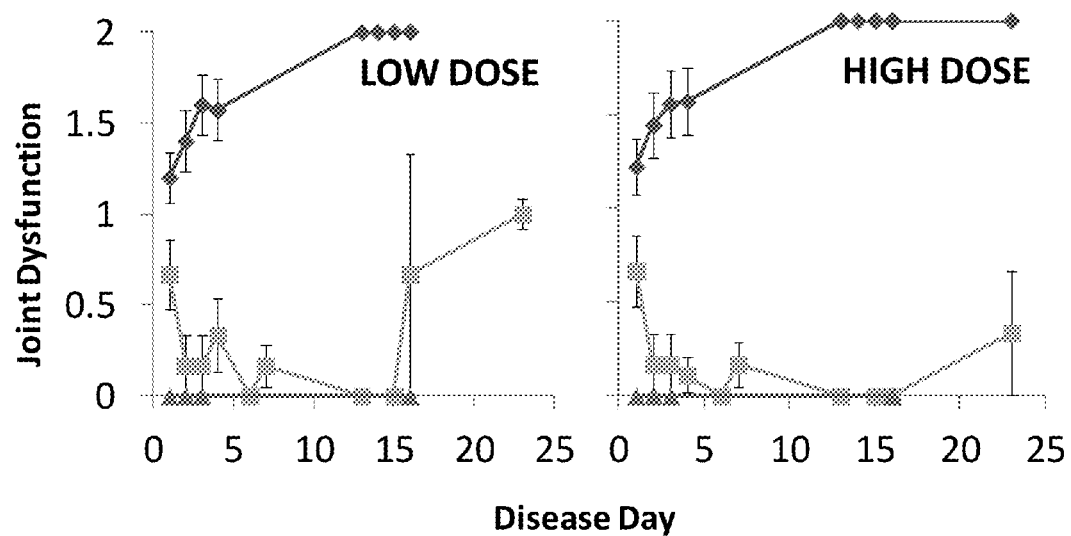
FIG. 21 illustrates graphs showing reduced joint dysfunction and improved mobility in rabbits treated with intra-articular dose of Anti-P antibody (low dose and high dose).

The antibody was administered at day "zero," at the same time that the mBSA challenge was used to induce the RA disease. The studies were ended at day 7, 14, 21, and 28. Analysis of disease progression and/or resolution was performed through histological evaluation of the joint tissues. This staining technology identifies the level of cartilage degradation, pannus formation as well as bone loss.

b) Inhibition of Inflammation, Pannus Formation, Cartilage Damage, and Bone Damage The images in FIG. 19 show diseased vs. treated knee joints. These images provide clear visual evidence of antibody-mediated inhibition of pannus formation, cartilage loss, and synovitis. FIG. 20 shows numerically quantified data demonstrating antibody-mediated inhibition of pannus formation, cartilage damage, and bone damage. Both figures demonstrate the therapeutic value of the alternative pathway specific antibodies of the present invention. FIG. 21 shows that the effect of the invention to prevent joint dysfunction is dose dependent.

c) Joint Dysfunction and Mobility Improvement

Mobility as a marker for joint dysfunction was also quantified in a 28 day rabbit AIA model of RA. Mobility was quantified at several time points between Day 0 and Day 28.

FIG. 21 shows that untreated rabbits had mobility impairment and joint dysfunction, while the alternative pathway specific antibody of the present invention treated animals displayed a significant reduction in these traits.

Inhibition of AP activation in vitro is well translated for its direct effect on inflammation and inflammatory conditions. Inflammation and cellular destruction & tissue injury are related. Inhibition of AP activation will prevent inflammation, cartilage and bone destruction. Conditions where inflammation plays a role in disease pathology can be corrected with the antibodies of the present invention.

EXAMPLE 8

Rabbit Osteoarthritis (OA) Model Experiments

To test the effect of compounds on another type of arthritis, osteoarthritis was induced in a rabbit model via the anterior cruciate ligament transaction (ACLT). This model has been described in literature which is readily accessible to those of ordinary skill in the art. In this model, rabbits were anesthetized, knees were shaven, the patella was shifted and a vertical cut was made to expose the joint capsule. An ACL incision was then made in each hind limb and each joint was sewn back in place. Eight animals per group were used (2 limbs from each). Prior to ACLT, saline was administered to the control group while the test group was given a treatment consisting of compounds of the present invention. Nine weeks after surgery the animals were euthanized and their hind limbs were analyzed for cartilage loss, cartilage degradation, and osteophyte formation. The results are shown in FIGS. 22 through 25.

Analysis of Cartilage Degeneration

In this rabbit model of OA, the parameters measured for cartilage degeneration included chondrocyte death/loss, proteoglycan (PG) loss, collagen loss, fibrillation and cartilage atrophy. The scores ranged from 0 for "no degeneration" to 5 for "severe degeneration." The three-zone sums for cartilage degeneration were also calculated.

Figure 22:
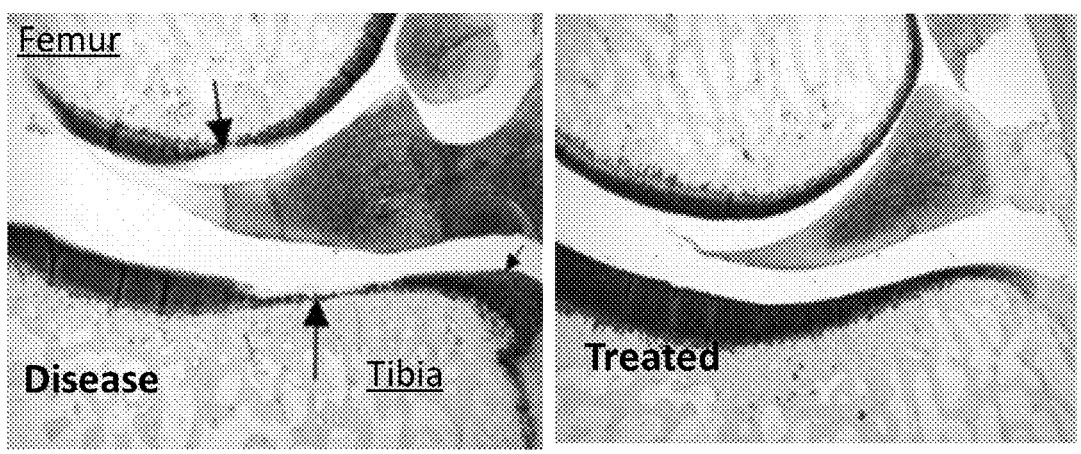
FIG. 22 illustrates images showing a joint having osteoarthritis and a joint treated with an alternative pathway specific anti-P antibody. Anti-P antibody prevents, cartilage loss and osteophyte formation.

FIG. 22 shows comparison of medial and lateral sides of both tibia and femur for the control (disease) rabbits and the treated rabbits. Comparison of the corresponding bars in each sub-group shows that the alternative pathway specific antibody of the present invention (the administered treatment) significantly reduces the cartilage degeneration scores.

b) Analysis of Total Cartilage Degeneration Width

Total Cartilage Degeneration Width is the measure of the total extent of tibial plateau affected by any type of degeneration (i.e. cell loss, proteoglycan loss, collagen damage, etc).

Figure 23:
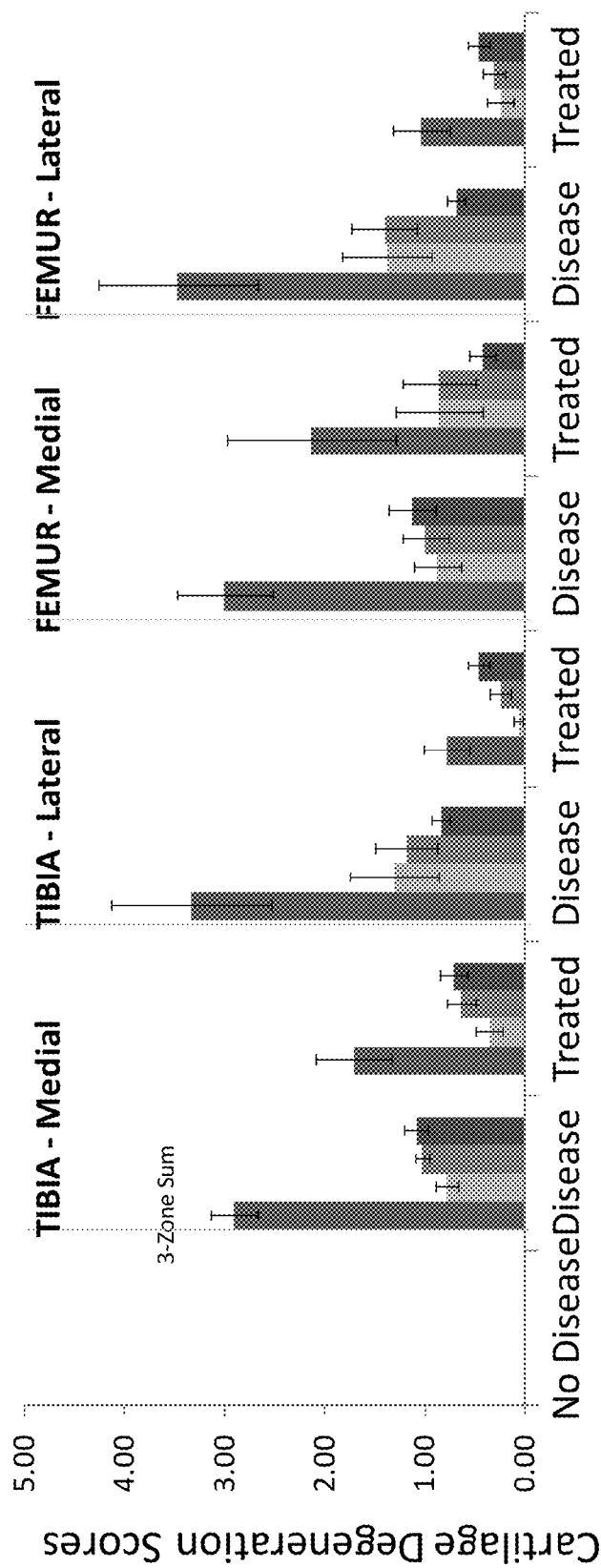
FIG. 23 illustrates a graph showing cartilage degeneration widths of both the tibia and femur of rabbits treated with an alternative pathway specific antibody are substantially decreased as opposed the cartilage degeneration widths of saline-injected rabbits. The graph compares the medial and lateral sides of a tibia and femur for saline-injected rabbits and rabbits treated with an alternative pathway specific antibody.

As shown in FIG. 23, the cartilage degeneration widths of both tibia and femur substantially decrease in rabbits treated with the alternative pathway specific antibody of the present invention from the saline injected animals.

c) Osteophytes with and without Cartilage Loss

Looking at osteophyte width and score, both these measurements are significantly reduced in those animals treated with the alternative pathway specific antibody of the present invention (when compared to the untreated control animals). The pathology of the disease animals highlights the efficacy of our monoclonal antibodies in rabbit OA model. Overall, the ACL surgical procedure caused significant changes in the cartilage over a nine week period.

Figure 24:
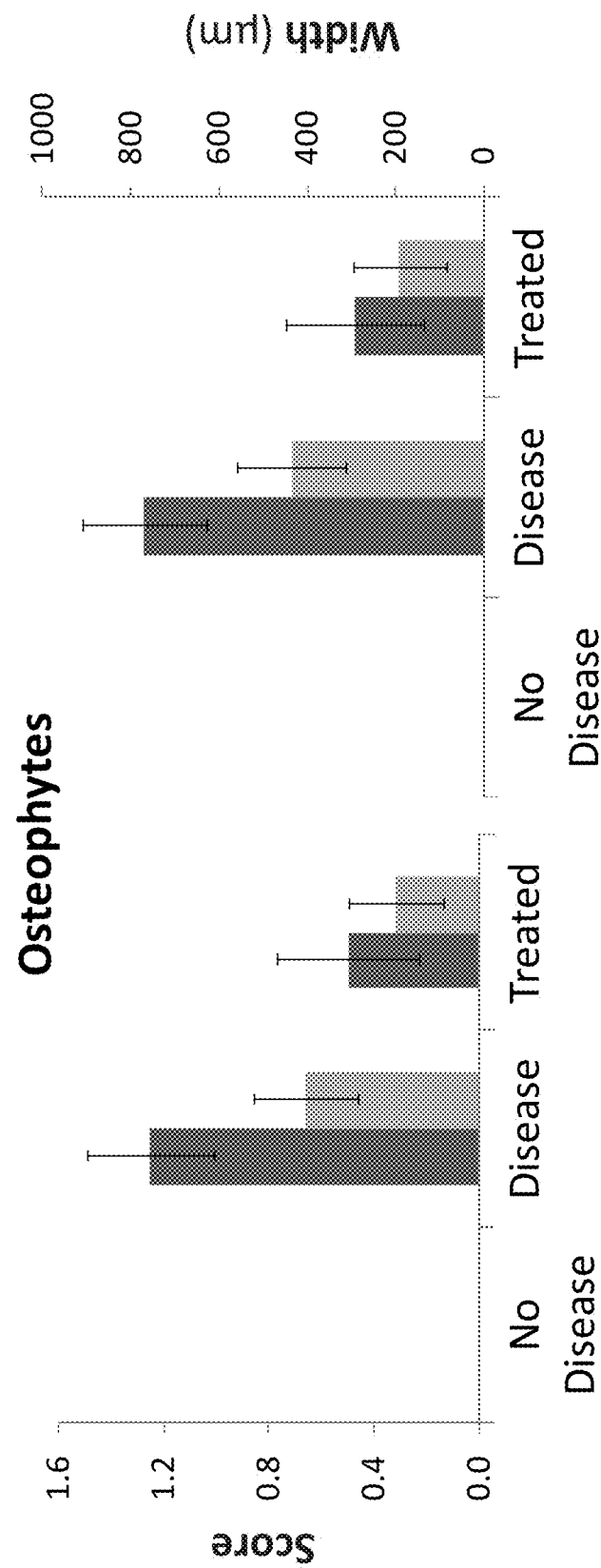
FIG. 24 illustrates a graph showing that osteophyte width in the joint of a rabbit treated with an alternative pathway specific antibody of the present invention are substantially decreased as opposed to the osteophyte widths in a joint of saline-injected rabbits.
Figure 25:
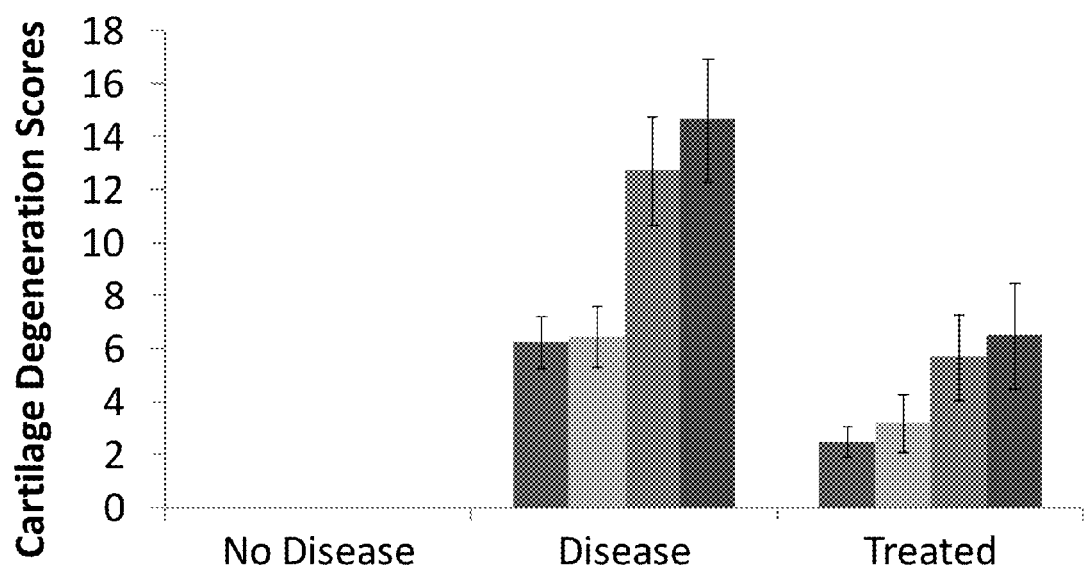
FIG. 25 illustrates a graph showing that the total cartilage degeneration from the tibia and femur of rabbits treated with an alternative pathway specific antibody of the present invention are substantially decreased as opposed the osteophyte total cartilage degeneration from the tibia and femur of saline-injected rabbits.

FIGS. 22, 24 and 25 show that untreated rabbits experienced extensive cartilage loss and osteophytes while the treated animals suffered significantly less. These results show that the alternative pathway specific antibody of the present invention is useful in arresting and halting the progression of OA.

EXAMPLE 9

The Antibody of the Present Invention Inhibits C35b-9 Formation in AP Buffer in 10% NHS Alternative pathway activation generates C3b via the cleaving of C3 by AP C3 convertase. C3 is thereby split into C3b and C3a. AP C5 convertase cleaves C5 into C5a and C5b. The C5b molecule inserts itself into the plasma membrane and generates C5b-9 molecules on the cell surface leading to cellular laysis and damage of the cell wall. Antibodies were evaluated for inhibition of C5b-9 using LPS to activate the Alternative Pathway. Microtiter plates were coated with LPS (Lipopolysaccharide from *Salmonella Typhosa*) 2 µg/50 µl in PBS overnight. The wells were incubated with 1% BSA in PBS to block the unoccupied sites on the plate. Following 2 hour incubation at room temperature, the plate was rinsed with PBS and incubated with Normal human serum (10% final concentration in AP buffer) was mixed with antibodies of the invention and incubated with LPS coated wells. The plate was again incubated for 2 hours 37° C. to allow C5b-9 formation to occur. The plates were extensively washed with PBS, and components of the C5b-9 were detected appropriately with neo antibody to C5b-9. We detected C5b-9 with mouse anti-MAC at 1:2000 in blocking solution. Following incubation, the plates were rinsed with PBS and prepared with peroxidase labeled goat anti-rabbit at 1:2000 in blocking solution for C3b detection. All plates were developed with TMB following extensive washing with PBS. In the presence of an AP specific antibody of the present invention inhibition of C3b formation was observed.

The alternative pathway specific antibodies of the present invention inhibit formation of C5b-9 produced in excess via the alternative complement pathway. C5b-9 coated cells are destroyed via intravsacular hemolysis in PNH disease. Other nucleated cells can be removed as well via the same mechanism. Thus neutropenia, leokopenia and thrombocytopenia are some examples where the end result is the reduction in the number of cells. The genus of antibodies claimed in the current application is expected to prevent the formation of C5b-9 responsible for removal of cells via extravascular route. Extravascular lysis is important in indications such as paroxysmal nocturnal hemoglobinuria where C5b-9 coated erythrocytes are removed from circulation via the intravascular lysis.

It is to be understood that this invention is not limited to particular embodiments described, as such may, of course, vary. It is also to be understood that the terminology used herein is for describing particular embodiments only, and is not intended to be limiting, since the scope of the present invention will be limited only by the appended claims. All patents, patent applications, publications listed or identified in this disclosure are herein incorporated by reference in their entirety.

1. Chiarella, G., et al., Proteomics in Meniere disease. J Cell Physiol, 2012. 227(1): p. 308-12.
2. Rieger, C. H., et al., Complement and protease inhibitors in the mucocutaneous lymph node syndrome. Eur J Pediatr, 1983. 140(2): p. 92-7.
3. Hoedemaekers, C. W., M. van Deuren, and J. G. van der Hoeven, Complement activation after cardiac surgery follows a biphasic pattern. Ann Thorac Surg, 2008. 86(5): p. 1723; author reply 1723.
4. Kawana, S., et al., Membrane attack complex of complement in Henoch-Schonlein purpura skin and nephritis. Arch Dermatol Res, 1990. 282(3): p. 183-7.
5. Thijs, L. G., et al., Activation of the complement system during immunotherapy with recombinant IL-2. Relation to the development of side effects. J Immunol, 1990. 144(6): p. 2419-24.
6. Kowalski, J., et al., Complement activates neutrophils during PTCA procedure in patients with unstable angina pectoris. Int J Cardiol, 1997. 58(3): p. 229-40.
7. Murohara, T., et al., Cardioprotective effects of selective inhibition of the two complement activation pathways in myocardial ischemia and reperfusion injury. Methods Find Exp Clin Pharmacol, 1995. 17(8): p. 499-507.
8. Banz, Y. and R. Rieben, Role of complement and perspectives for intervention in ischemia-reperfusion damage. Ann Med, 2012. 44(3): p. 205-17.
9. Iltumur, K., et al., Complement activation in acute coronary syndromes. APMIS, 2005. 113(3): p. 167-74.
10. Speidl, W. S., Atherosclerosis and complement: anaphylatoxin C5a as a new risk marker and therapeutic target. Clinical Lipidology, 2011. 6(2): p. 123-126.
11. Kawana, S., The membrane attack complex of complement alters the membrane integrity of cultured endothelial cells: a possible pathophysiology for immune complex vasculitis. Acta Derm Venereol, 1996. 76(1): p. 13-6.
12. Cochrane, C. G., The role of complement in experimental disease models. Springer Seminars in Immunopathology, 1984. 7: p. 263-279.
13. Vaith, P., et al., A new serological reaction in patients with polymyalgia rheumatica and/or giant cell (temporal) arteritis: deposition of complement C4 and C3 components on rat kidney structures detected by indirect immunofluorescence. Rheumatol Int, 1986. 6(6): p. 255-61.
14. Harkin, D. W., et al., C5 complement inhibition attenuates shock and acute lung injury in an experimental model of ruptured abdominal aortic aneurysm. Br J Surg, 2005. 92(10): p. 1227-34.
15. Afanasyeva, M. and N. R. Rose, Cardiomyopathy is linked to complement activation. Am J Pathol, 2002. 161(2): p. 351-7.
16. Langlois, P. F., G. E. Sharon, and M. S. Gawryl, Plasma concentrations of complement-activation complexes correlate with disease activity in patients diagnosed with isolated central nervous system vasculitis. J Allergy Clin Immunol, 1989. 83(1): p. 11-6.
17. Xiao, H., et al., Alternative complement pathway in the pathogenesis of disease mediated by anti-neutrophil cytoplasmic autoantibodies. Am J Pathol, 2007. 170(1): p. 52-64.
18. Tripathy, N. K., et al., Complement and cell mediated cytotoxicity by antiendothelial cell antibodies in Takayasu's arteritis. J Rheumatol, 2001. 28(4): p. 805-8.
19. Zwaka, T. P., et al., Complement and dilated cardiomyopathy: a role of sublytic terminal complement complex-induced tumor necrosis factor-alpha synthesis in cardiac myocytes. Am J Pathol, 2002. 161(2): p. 449-57.
20. Zhang, J., et al., Venous gas emboli and complement activation after deep repetitive air diving. Undersea Biomed Res, 1991. 18(4): p. 293-302.
21. Castellino, G., et al., Wegener's granulomatosis associated with antiphospholipid syndrome. Lupus, 2000. 9(9): p. 717-20.
22. Arbesfeld, S. J. and A. K. Kurban, Behcet's disease. New perspectives on an enigmatic syndrome. J Am Acad Dermatol, 1988. 19(5 Pt 1): p. 767-79.
23. Fairweather, D., et al., Complement receptor 1 and 2 deficiency increases coxsackievirus B3-induced myocarditis, dilated cardiomyopathy, and heart failure by increasing macrophages, IL-1beta, and immune complex deposition in the heart. J Immunol, 2006. 176(6): p. 3516-24.
24. Aiello, V. D., et al., A possible role for complement in the pathogenesis of chronic chagasic cardiomyopathy. J Pathol, 2002. 197(2): p. 224-9.
25. Speidl, W. S., et al., Complement component C5a predicts restenosis after superficial femoral artery balloon angioplasty. J Endovasc Ther, 2007. 14(1): p. 62-9.
26. Pomara, C., et al., C3a, TNF-alpha and interleukin myocardial expression in a case of fatal sudden cardiac failure during clinic reactivation of systemic lupus erythematosus. Lupus, 2010. 19(10): p. 1246-9.
27. Szeplaki, G., et al., Association of high serum concentration of the third component of complement (C3) with pre-existing severe coronary artery disease and new vascular events in women. Atherosclerosis, 2004. 177(2): p. 383-9.
28. Earis, J. E., E. C. Marcuson, and A. Bernstein, Complement activation after myocardial infarction. Chest, 1985. 87(2): p. 186-90.
29. Feigal, D. W., D. L. Robbins, and J. C. Leek, Giant cell arteritis associated with mononeuritis multiplex and complement-activating 19S IgM rheumatoid factor. Am J Med, 1985. 79(4): p. 495-500.
30. Testa, L., et al., Pexelizumab in ischemic heart disease: a systematic review and meta-analysis on 15,196 patients. J Thorac Cardiovasc Surg, 2008. 136(4): p. 884-93.
31. Dauchel, H., et al., Local and systemic activation of the whole complement cascade in human leukocytoclastic cutaneous vasculitis; C3d, g and terminal complement complex as sensitive markers. Clin Exp Immunol, 1993. 92(2): p. 274-83.
32. Chen, J., et al., A novel inhibitor of the alternative pathway of complement attenuates intestinal ischemia/reperfusion-induced injury. J Surg Res, 2011. 167(2): p. e131-6.

33. Lapchak, P. H., et al., Platelets orchestrate remote tissue damage after mesenteric ischemia-reperfusion. Am J Physiol Gastrointest Liver Physiol, 2011. 302(8): p. G888-97.
34. Flores-Suarez, L. F., [The complement system in the pathogenesis of antineutrophil cytoplasm antibodies-associated vasculitis]. Reumatol Clin, 2011. 7 Suppl 3: p. S18-21.
35. Xing, G. Q., et al., Complement activation is involved in renal damage in human antineutrophil cytoplasmic autoantibody associated pauci-immune vasculitis. J Clin Immunol, 2009. 29(3): p. 282-91.
36. Bowers, T. K., et al., Hyperacute pulmonary vasculitis in rabbits receiving prolonged infusions of activated complement. A possible model for triggering events in adult respiratory distress syndrome. Inflammation, 1983. 7(1): p. 1-13.
37. Kahaleh, M. B., Raynaud's phenomenon and the vascular disease in scleroderma. Curr Opin Rheumatol, 1995. 7(6): p. 529-34.
38. Kirklin, J. K. and D. C. McGiffin, Control of the inflammatory response in extended myocardial preservation of the donor heart. Ann Thorac Surg, 1999. 68(5): p. 1978-82.
39. Huang, K. L. and Y. C. Lin, Activation of complement and neutrophils increases vascular permeability during air embolism. Aviat Space Environ Med, 1997. 68(4): p. 300-5.
40. Nilsson, B., et al., The role of complement in biomaterial-induced inflammation. Mol Immunol, 2007. 44(1-3): p. 82-94.
41. Reyes, P. A., et al., Association of rheumatoid factor with complement activation in rheumatoid arthritis and other diseases. Clin Exp Immunol, 1983. 53(2): p. 391-6.
42. Voskuyl, A. E., et al., Diagnostic strategy for the assessment of rheumatoid vasculitis. Ann Rheum Dis, 2003. 62(5): p. 407-13.
43. Vianna, M. A., et al., Myositis in mixed connective tissue disease: a unique syndrome characterized by immunohistopathologic elements of both polymyositis and dermatomyositis. Arq Neuropsiquiatr, 2004. 62(4): p. 923-34.
44. Vaith, P., G. M. Hansch, and H. H. Peter, C-reactive protein-mediated complement activation in polymyalgia rheumatica and other systemic inflammatory diseases. Rheumatol Int, 1988. 8(2): p. 71-80.
45. Dahl, M. V., et al., Deposition of the membrane attack complex of complement in bullous pemphigoid. J Invest Dermatol, 1984. 82(2): p. 132-5.
46. Mihai, S., et al., The alternative pathway of complement activation is critical for blister induction in experimental epidermolysis bullosa acquisita. J Immunol, 2007. 178 (10): p. 6514-21.
47. Mutasim, D. F., Management of autoimmune bullous diseases: pharmacology and therapeutics. J Am Acad Dermatol, 2004. 51(6): p. 859-77; quiz 878-80.
48. Liu, Z., et al., The role of complement in experimental bullous pemphigoid. J Clin Invest, 1995. 95(4): p. 1539-44.
49. Sprott, H., et al., Detection of activated complement complex C5b-9 and complement receptor C5a in skin biopsies of patients with systemic sclerosis (scleroderma). J Rheumatol, 2000. 27(2): p. 402-4.
50. Gelfand, J. A., The role of complement in urticaria and angioedema. Clin Immunol Rev, 1981. 1(2): p. 257-309.
51. Asghar, S. S. and M. C. Pasch, Therapeutic inhibition of the complement system. Y2K update. Front Biosci, 2000. 5: p. E63-81.
52. Grimwood, R., J. C. Huff, and W. L. Weston, Complement deposition in the skin of patients with herpes-associated erythema multiforme. J Am Acad Dermatol, 1983. 9(2): p. 199-203.
53. Katz, S. I., K. C. Hertz, and H. Yaoita, Herpes gestationis. Immunopathology and characterization of the HG factor. J Clin Invest, 1976. 57(6): p. 1434-41.
54. Sanders, M. E., et al., Detection of activated terminal complement (C5b-9) in cerebrospinal fluid from patients with central nervous system involvement of primary Sjogren's syndrome or systemic lupus erythematosus. J Immunol, 1987. 138(7): p. 2095-9.
55. Acevedo, F. and H. Hammar, Complement C3 proteins in psoriasis. Br J Dermatol, 1989. 121(3): p. 329-35.
56. Rosenberg, E. W., et al., Complement activation in psoriasis. Clin Exp Dermatol, 1990. 15(1): p. 16-20.
57. Fairhurst, D. A., A. Mitra, and S. MacDonald-Hull, Direct Immunofluorescence studies of patients with alopecia areata in affected and clinically normal areas of scalp. Journal of the European Academy of Dermatology and Venereology, 2009. 23(3): p. 347-348.
58. Kapp, A., H. Wokalek, and E. Schopf, Involvement of complement in psoriasis and atopic dermatitis—measurement of C3a and C5a, C3, C4 and C1 inactivator. Arch Dermatol Res, 1985. 277(5): p. 359-61.
59. Chan, L. S., Ocular and oral mucous membrane pemphigoid (cicatricial pemphigoid). Clinics in Dermatology, 2012. 30(1): p. 34-37.
60. Kotnik, V., Complement in skin diseases. Acta Dermatovenerol Alp Panonica Adriat, 2011. 20(1): p. 3-11.
61. Papp, G., et al., Altered T-cell and regulatory cell repertoire in patients with diffuse cutaneous systemic sclerosis. Scand J Rheumatol, 2011. 40(3): p. 205-10.
62. Wild, J. H., et al., C3 metabolism in a patient with deficiency of the second component of complement (C2) and discoid lupus erythematosus. Clin Exp Immunol, 1976. 24(2): p. 238-48.
63. Tagami, H., The role of complement-derived mediators in inflammatory skin diseases. Arch Dermatol Res, 1992. 284 Suppl 1: p. S2-9.
64. Lahiri, R., et al., Activation of complement by *Mycobacterium leprae* requires disruption of the bacilli. Lepr Rev, 2008. 79(3): p. 311-4.
65. Fahad, A. S. and A. R. Ammar, Unusual clinicopathological and immunological presentation of chronic bullous dermatosis of childhood (linear IgA dermatosis). Indian J Dermatol, 2011. 56(5): p. 573-5.
66. Faber, W. R. and T. van Joost, Pityriasis lichenoides, an immune complex disease? Acta Derm Venereol, 1980. 60(3): p. 259-61.
67. Coors, E. A. and P. von den Driesch, Pyoderma gangrenosum in a patient with autoimmune haemolytic anaemia and complement deficiency. Br J Dermatol, 2000. 143(1): p. 154-6.
68. Venneker, G. T., et al., Molecular Heterogeneity of the Fourth Component of Complement (C4) and its Genes in Vitiligo. J Investig Dermatol, 1992. 99(6): p. 853-858.
69. Tandon, N., et al., Expression and function of multiple regulators of complement activation in autoimmune thyroid disease. Immunology, 1994. 81(4): p. 643-7.
70. Morimoto, Y., et al., Complements in diabetes mellitus: activation of complement system evidenced by C3d elevation in IDDM. Diabetes Res Clin Pract, 1988. 5(4): p. 309-12.
71. Maes, M., et al., Effects of psychological stress on serum immunoglobulin, complement and acute phase protein concentrations in normal volunteers. Psychoneuroendocrinology, 1997. 22(6): p. 397-409.
72. Foulis, A. K., et al., Endotoxaemia and complement activation in acute pancreatitis in man. Gut, 1982. 23(8): p. 656-61.
73. McNatty, K. P., et al., The cytotoxic effect of serum from patients with Addison's disease and autoimmune ovarian failure on human granulosa cells in culture. Clin Exp Immunol, 1975. 22(3): p. 378-84.
74. Moreno-Navarrete, J. M., et al., Complement factor H is expressed in adipose tissue in association with insulin resistance. Diabetes. 59(1): p. 200-9.
75. Flyvbjerg, A., Diabetic angiopathy, the complement system and the tumor necrosis factor superfamily. Nat Rev Endocrinol, 2010. 6(2): p. 94-101.
76. Potlukova, E., et al., Autoantibodies against complement C1q correlate with the thyroid function in patients with autoimmune thyroid disease. Clin Exp Immunol, 2008. 153(1): p. 96-101.
77. Sonntag, J., et al., Complement and contact activation during cardiovascular operations in infants. Ann Thorac Surg, 1998. 65(2): p. 525-31.
78. Mollnes, T. E., et al., Complement activation and bio-incompatibility. The terminal complement complex for evaluation and surface modification with heparin for improvement of biomaterials. Clin Exp Immunol, 1991. 86 Suppl 1: p. 21-6.
79. Agostoni, A. and M. Gardinali, Complement activation during hemodialysis. J Biomater Appl, 1989. 4(2): p. 102-22.
80. Nishise, S., et al., Complement activation is involved in biological responses to leukocyte adsorptive apheresis. Dig Dis Sci, 2006. 51(5): p. 934-41.
81. Shiga, Y., et al., Complement activation as a cause of transient hypotension during plasmapheresis. Artif Organs, 1998. 22(12): p. 1067-9.
82. Hetland, G., T. E. Mollnes, and P. Garred, Activation of complement during apheresis. Clin Exp Immunol, 1991. 84(3): p. 535-8.
83. Wurzner, R., et al., Complement activation and depletion during LDL-apheresis by heparin-induced extracorporeal LDL-precipitation (HELP). Eur J Clin Invest, 1991. 21(3): p. 288-94.
84. Pekna, M., et al., Complement activation during cardiopulmonary bypass: effects of immobilized heparin. Ann Thorac Surg, 1994. 58(2): p. 421-4.
85. Vallhonrat, H., et al., Rapid activation of the alternative pathway of complement by extracorporeal membrane oxygenation. ASAIO J, 1999. 45(1): p. 113-4.
86. Kirklin, J. K., et al., Complement and the damaging effects of cardiopulmonary bypass. J Thorac Cardiovasc Surg, 1983. 86(6): p. 845-57.
87. Salama, A., et al., Deposition of terminal C5b-9 complement complexes on erythrocytes and leukocytes during cardiopulmonary bypass. N Engl J Med, 1988. 318(7): p. 408-14.
88. Thiara, A. S., et al., Biocompatibility and pathways of initial complement pathway activation with Phisio- and PMEA-coated cardiopulmonary bypass circuits during open-heart surgery. Perfusion, 2011. 26(2): p. 107-14.
89. Zimmermann-Nielsen, E., et al., Complement activation capacity in plasma before and during high-dose prednisolone treatment and tapering in exacerbations of Crohn's disease and ulcerative colitis. BMC Gastroenterol, 2005. 5: p. 31.
90. Halstensen, T. S., et al., Association of subepithelial deposition of activated complement and immunoglobulin G and M response to gluten in celiac disease. Gastroenterology, 1992. 102(3): p. 751-9.
91. Eror, A. T., et al., Antiinflammatory effects of soluble complement receptor type 1 promote rapid recovery of ischemia/reperfusion injury in rat small intestine. Clin Immunol, 1999. 90(2): p. 266-75.
92. Woodruff, T. M., et al., Increased potency of a novel complement factor 5a receptor antagonist in a rat model of inflammatory bowel disease. J Pharmacol Exp Ther, 2005. 314(2): p. 811-7.
93. Chen, G., et al., Blockade of complement activation product C5a activity using specific antibody attenuates intestinal damage in trinitrobenzene sulfonic acid induced model of colitis. Lab Invest, 2010. 91(3): p. 472-483.
94. Barbie, D. A., A. A. Mangi, and G. Y. Lauwers, Eosinophilic gastroenteritis associated with systemic lupus erythematosus. J Clin Gastroenterol, 2004. 38(10): p. 883-6.
95. Berstad, A. E., et al., Complement activation directly induced by *Helicobacter pylori*. Gastroenterology, 2001. 120(5): p. 1108-16.
96. Erkan, D. and M. D. Lockshin, Antiphospholipid syndrome. Curr Opin Rheumatol, 2006. 18(3): p. 242-8.
97. Jaffe, C. J., J. P. Atkinson, and M. M. Frank, The role of complement in the clearance of cold agglutinin-sensitized erythrocytes in man. J Clin Invest, 1976. 58(4): p. 942-9.
98. Tsai, H. M., The molecular biology of thrombotic microangiopathy. Kidney Int, 2006. 70(1): p. 16-23.
99. Hed, J., Role of complement in immune or idiopathic thrombocytopenic purpura. Acta Paediatr Suppl, 1998. 424: p. 37-40.
100. Alexander, J. J., et al., Complement factor h limits immune complex deposition and prevents inflammation and scarring in glomeruli of mice with chronic serum sickness. J Am Soc Nephrol, 2005. 16(1): p. 52-7.
101. McPhaden, A. R. and K. Whaley, The complement system in sepsis and trauma. Br Med Bull, 1985. 41(3): p. 281-6.
102. Markiewski, M. M., R. A. DeAngelis, and J. D. Lambris, Complexity of complement activation in sepsis. Journal of Cellular and Molecular Medicine, 2008. 12(6a): p. 2245-2254.
103. Goicoechea de Jorge, E., et al., Gain-of-function mutations in complement factor B are associated with atypical hemolytic uremic syndrome. Proc Natl Acad Sci USA, 2007. 104(1): p. 240-5.
104. Hillmen, P., et al., Effect of the complement inhibitor eculizumab on thromboembolism in patients with paroxysmal nocturnal hemoglobinuria. Blood, 2007. 110(12): p. 4123-8.
105. Devine, D. V., R. S. Siegel, and W. F. Rosse, Interactions of the platelets in paroxysmal nocturnal hemoglobinuria with complement. Relationship to defects in the regulation of complement and to platelet survival in vivo. J Clin Invest, 1987. 79(1): p. 131-7.
106. Sprung, C. L., et al., Complement activation in septic shock patients. Crit Care Med, 1986. 14(6): p. 525-8.
107. Chudwin, D. S., et al., Increased activation of the alternative complement pathway in sickle cell disease. Clin Immunol Immunopathol, 1985. 37(1): p. 93-7.
108. Wymann, M. P., et al., Activation of the respiratory burst in eosinophil leucocytes—a transduction sequence decoupled from cytosolic Ca2+ rise. Eur J Clin Invest, 1995. 25(1): p. 25-31.
109. Barros, M. M., et al., Expression levels of CD47, CD35, CD55, and CD59 on red blood cells and signalregulatory protein-alpha, beta on monocytes from patients with warm autoimmune hemolytic anemia. Transfusion, 2009. 49(1): p. 154-60.
110. Bussone, G. and L. Mouthon, Autoimmune manifestations in primary immune deficiencies. Autoimmun Rev, 2009. 8(4): p. 332-6.
111. Magro, C. M., et al., Degos disease: a C5b-9/interferon-alpha-mediated endotheliopathy syndrome. Am J Clin Pathol, 2011. 135(4): p. 599-610.
112. Moncharmont, P., J. Troncy, and D. Rigal, IgA anti-red blood cell auto-antibodies in Evans syndrome. Hematology, 2007. 12(6): p. 587-9.
113. Corvetta, A., et al., Complement activation and impaired capacity to solubilize immune complexes or to prevent their formation in essential mixed cryoglobulinemia. Diagn Immunol, 1983. 1(4): p. 315-23.
114. Higuchi, T., et al., Hypocomplementemia and hematological abnormalities in immunoblastic lymphadenopathy and immunoblastic lymphadenopathy-like T cell lymphoma. Acta Haematol, 1996. 96(2): p. 68-72.
115. Lin, R. Y., et al., Immunological abnormalities in autoimmune chronic active hepatitis. J Rheumatol, 1989. 16(11): p. 1489-93.
116. Munoz, L. E., et al., Complement activation in chronic liver disease. Clin Exp Immunol, 1982. 47(3): p. 548-54.
117. Kosmidis, J. C. and L. K. Leader-Williams, Complement levels in acute infectious hepatitis and serum hepatitis. Clin Exp Immunol, 1972. 11(1): p. 31-5.
118. Barak, V., et al., Serum inflammatory cytokines, complement components, and soluble interleukin 2 receptor in primary biliary cirrhosis. J Autoimmun, 2009. 33(3-4): p. 178-82.
119. Lundgren, B. A., et al., Identification of complement C3 as an autoantigen in inflammatory bowel disease. Eur J Gastroenterol Hepatol, 2010. 22(4): p. 429-36.
120. Garred, P., et al., Deposition of C3, the terminal complement complex and vitronectin in primary biliary cirrhosis and primary sclerosing cholangitis. Liver, 1993. 13(6): p. 305-10.
121. Savage, D. B., et al., Complement abnormalities in acquired lipodystrophy revisited. J Clin Endocrinol Metab, 2009. 94(1): p. 10-6.
122. Kaneko, I., K. Kamoshida, and S. Takahashi, Complestatin, a potent anti-complement substance produced by *Streptomyces lavendulae*. I. Fermentation, isolation and biological characterization. J Antibiot (Tokyo), 1989. 42(2): p. 236-41.
123. Gyoten, M., [Activation of the complement system and cytokine production by radiographic contrast media in vascular endothelial cells in vitro]. Nippon Igaku Hoshasen Gakkai Zasshi, 1998. 58(14): p. 811-5.
124. Lieberman, P. L. and R. L. Seigle, Reactions to radiocontrast material. Anaphylactoid events in radiology. Clin Rev Allergy Immunol, 1999. 17(4): p. 469-96.
125. Daniel, V. and D. Stephen, Adverse reactions to drugs. BMJ, 1998. 316.
126. Gerard, N. and C. Gerard, Complement in allergy and asthma. 2002(0952-7915 (Print)).
127. Sofat, N., Analysing the role of endogenous matrix molecules in the development of osteoarthritis. Int J Exp Pathol, 2009. 90(5): p. 463-79.
128. Kamen, D. L. and J. D. Alele, Skeletal manifestations of systemic autoimmune diseases. Current Opinion in Endocrinology, Diabetes and Obesity, 2010. 17(6).
129. Tramontini, N., et al., Central role of complement membrane attack complex in monosodium urate crystal-induced neutrophilic rabbit knee synovitis. Arthritis Rheum, 2004. 50(8): p. 2633-9.
130. Lindsley, C. B., Juvenile rheumatoid arthritis and spondyloarthropathies. Curr Opin Rheumatol, 1995. 7(5): p. 425-9.
131. Dalakas, M. C., Therapeutic targets in patients with inflammatory myopathies: present approaches and a look to the future. Neuromuscul Disord, 2006. 16(4): p. 223-36.
132. Basta, M. and M. C. Dalakas, High-dose intravenous immunoglobulin exerts its beneficial effect in patients with dermatomyositis by blocking endomysial deposition of activated complement fragments. J Clin Invest, 1994. 94(5): p. 1729-35.
133. Happonen, K. E., et al., Serum COMP-C3b complexes in rheumatic diseases and relation to anti-TNF-alpha treatment. Arthritis Res Ther, 2012. 14(1): p. R15.
134. Li, C. W., J. Hu, and S. H. Pi, [Clinical characteristics of children with enthesitis related arthritis]. Zhonghua Er Ke Za Zhi, 2003. 41(11): p. 835-8.
135. Barnes, L., et al., Eosinophilic fasciitis. A pathologic study of twenty cases. Am J Pathol, 1979. 96(2): p. 493-518.
136. Gilliam, B. E., et al., Significance of complement components C1q and C4 bound to circulating immune complexes in juvenile idiopathic arthritis: support for classical complement pathway activation. Clin Exp Rheumatol, 2011. 29(6): p. 1049-56.
137. Gunn, B. M., et al., Mannose Binding Lectin Is Required for Alphavirus-Induced Arthritis/Myositis. PLoS Pathog, 2012. 8(3): p. e1002586.
138. Ballanti, E., et al., Role of the complement system in rheumatoid arthritis and psoriatic arthritis: relationship with anti-TNF inhibitors. Autoimmun Rev, 2011. 10(10): p. 617-23.
139. Li, C. W., et al., [Reiter's syndrome in children: a clinical analysis of 22 cases]. Zhonghua Er Ke Za Zhi, 2010. 48(3): p. 212-5.
140. Hansson, A.-S., et al., Relapsing Polychondritis, Induced in Mice with Matrilin 1, Is an Antibody- and Complement-Dependent Disease. The American journal of pathology, 2004. 164(3): p. 959-966.
141. Barohn, R. J. and R. L. Brey, Soluble terminal complement components in human myasthenia gravis. Clin Neurol Neurosurg, 1993. 95(4): p. 285-90.
142. Ingram, G., et al., Complement in multiple sclerosis: its role in disease and potential as a biomarker. Clin Exp Immunol, 2009. 155(2): p. 128-39.
143. Hartung, H. P., et al., Guillain-Barre syndrome: activated complement components C3a and C5a in CSF. Neurology, 1987. 37(6): p. 1006-9.
144. Szeplaki, G., et al., Strong complement activation after acute ischemic stroke is associated with unfavorable outcomes. Atherosclerosis, 2009. 204(1): p. 315-20.
145. Klein, M. A., et al., Complement facilitates early prion pathogenesis. Nat Med, 2001. 7(4): p. 488-92.
146. Mabbott, N. A., et al., Temporary depletion of complement component C3 or genetic deficiency of C1q significantly delays onset of scrapie. Nat Med, 2001. 7(4): p. 485-7.
147. Levin, M. E., et al., Complement activation in the peripheral nervous system following the spinal nerve ligation model of neuropathic pain. Pain, 2008. 137(1): p. 182-201.

148. Li, M., et al., Complement activation contributes to leukocyte recruitment and neuropathic pain following peripheral nerve injury in rats. Eur J Neurosci, 2007. 26(12): p. 3486-500.
149. Twining, C. M., et al., Peri-sciatic proinflammatory cytokines, reactive oxygen species, and complement induce mirror-image neuropathic pain in rats. Pain, 2004. 110(1-2): p. 299-309.
150. Fonseca, M. I., et al., Treatment with a C5aR Antagonist Decreases Pathology and Enhances Behavioral Performance in Murine Models of Alzheimer's Disease. The Journal of Immunology, 2009. 183(2): p. 1375-1383.
151. Stangel, M., K. V. Toyka, and R. Gold, Mechanisms of high-dose intravenous immunoglobulins in demyelinating diseases. Arch Neurol, 1999. 56(6): p. 661-3.
152. Uetz-von Allmen, E., et al., Antiganglioside GM1 antibodies and their complement activating capacity in central and peripheral nervous system disorders and in controls. Eur Neurol, 1998. 39(2): p. 103-10.
153. Woodruff, T. M., et al., Therapeutic activity of C5a receptor antagonists in a rat model of neurodegeneration. FASEB J, 2006. 20(9): p. 1407-17.
154. Woodruff, T. M., et al., Role of complement in motor neuron disease: animal models and therapeutic potential of complement inhibitors. Adv Exp Med Biol, 2008. 632: p. 143-58.
155. McCombe, P. A. and R. D. Henderson, The Role of immune and inflammatory mechanisms in ALS. Curr Mol Med, 2011. 11(3): p. 246-54.
156. Loeffler, D. A., D. M. Camp, and S. B. Conant, Complement activation in the Parkinson's disease substantia nigra: an immunocytochemical study. J Neuroinflammation, 2006. 3: p. 29.
157. Goldknopf, I. L., et al., Complement C3c and related protein biomarkers in amyotrophic lateral sclerosis and Parkinson's disease. Biochem Biophys Res Commun, 2006. 342(4): p. 1034-9.
158. Winer, J. B., et al., A prospective study of acute idiopathic neuropathy. III. Immunological studies. J Neurol Neurosurg Psychiatry, 1988. 51(5): p. 619-25.
159. Whitaker, J. N., et al., Serum immunoglobulin and complement (C3) levels: a study in adults with idiopathic, chronic polyneuropathies and motor neuron diseases. Neurology, 1973. 23(11): p. 1164-73.
160. Vriesendorp, F. J., et al., Systemic complement depletion reduces inflammation and demyelination in adoptive transfer experimental allergic neuritis. Acta Neuropathol, 1998. 95(3): p. 297-301.
161. Vriesendorp, F. J., et al., Soluble complement receptor 1 (sCR1) is not as effective as cobra venom factor in the treatment of experimental allergic neuritis. Int J Neurosci, 1997. 92(3-4): p. 287-98.
162. Vriesendorp, F. J., et al., Complement depletion affects demyelination and inflammation in experimental allergic neuritis. J Neuroimmunol, 1995. 58(2): p. 157-65.
163. Feasby, T. E., et al., Complement depletion suppresses Lewis rat experimental allergic neuritis. Brain Res, 1987. 419(1-2): p. 97-103.
164. Mader, S., et al., Complement activating antibodies to myelin oligodendrocyte glycoprotein in neuromyelitis optica and related disorders. J Neuroinflammation, 2011. 8: p. 184.
165. Graham, D. I., P. O. Behan, and I. A. More, Brain damage complicating septic shock: acute haemorrhagic leucoencephalitis as a complication of the generalised Shwartzman reaction. J Neurol Neurosurg Psychiatry, 1979. 42(1): p. 19-28.
166. O'Hanlon, G. M., et al., Calpain inhibitors protect against axonal degeneration in a model of anti-ganglioside antibody-mediated motor nerve terminal injury. Brain, 2003. 126(Pt 11): p. 2497-509.
167. Mandi-Rogers, M. and Y. A. Rajabally, Overview of the pathogenesis and treatment of chronic inflammatory demyelinating polyneuropathy with intravenous immunoglobulins. Biologics, 2010. 4: p. 45-9.
168. Dyer, J. K., J. A. Bourque, and J. D. Steeves, The role of complement in immunological demyelination of the mammalian spinal cord. Spinal Cord, 2005. 43(7): p. 417-425.
169. Wingerchuk, D. M. and C. F. Lucchinetti, Comparative immunopathogenesis of acute disseminated encephalomyelitis, neuromyelitis optica, and multiple sclerosis. Curr Opin Neurol, 2007. 20(3): p. 343-50.
170. Dalakas, M. C., The use of intravenous immunoglobulin in the treatment of autoimmune neuromuscular diseases: evidence-based indications and safety profile. Pharmacol Ther, 2004. 102(3): p. 177-93.
171. Woehrl, B., et al., Complement component 5 contributes to poor disease outcome in humans and mice with pneumococcal meningitis. The Journal of Clinical Investigation, 2011. 121(10): p. 3943-3953.
172. Kaida, K. and S. Kusunoki, Antibodies to gangliosides and ganglioside complexes in Guillain-Barre syndrome and Fisher syndrome: mini-review. J Neuroimmunol, 2010. 223(1-2): p. 5-12.
173. Kim, W., S. H. Kim, and H. J. Kim, New insights into neuromyelitis optica. J Clin Neurol, 2011. 7(3): p. 115-27.
174. Mead, R. J., et al., The membrane attack complex of complement causes severe demyelination associated with acute axonal injury. J Immunol, 2002. 168(1): p. 458-65.
175. Spalice, A. a. P., Pasquale and Papetti, Laura and Nicita, Francesco and Ursitti, Fabiana and Del Balzo, Francesca and Properzi, Enrico and Verrotti, Alberto and Ruggieri, Martino and Iannetti, Paola, Clinical and Pharmacological Aspects of Inflammatory Demyelinating Diseases in Childhood: An Update. Current Neuropharmacology, 2010. 8(2): p. 135-148.
176. Pranzatelli, M. R., et al., Rituximab (anti-CD20) adjunctive therapy for opsoclonus-myoclonus syndrome. J Pediatr Hematol Oncol, 2006. 28(9): p. 585-93.
177. Whitney, K. D., P. I. Andrews, and J. O. McNamara, Immunoglobulin G and complement immunoreactivity in the cerebral cortex of patients with Rasmussen's encephalitis. Neurology, 1999. 53(4): p. 699-708.
178. Yaddanapudi, K., et al., Passive transfer of streptococcus-induced antibodies reproduces behavioral disturbances in a mouse model of pediatric autoimmune neuropsychiatric disorders associated with streptococcal infection. Mol Psychiatry, 2010. 15(7): p. 712-26.
179. Dalakas, M. C., Intravenous immunoglobulin in autoimmune neuromuscular diseases. JAMA, 2004. 291(19): p. 2367-75.
180. Kleffner, I., et al., A brief review of Susac syndrome. Journal of the Neurological Sciences, 2012(0).
181. Kulkarni, A. P., et al., Modulation of anxiety behavior by intranasally administered vaccinia virus complement control protein and curcumin in a mouse model of Alzheimer's disease. Curr Alzheimer Res, 2011. 8(1): p. 95-113.
182. Mondino, B. J., Y. Sidikaro, and H. Sumner, Anaphylatoxin levels in human vitreous humor. Invest Ophthalmol Vis Sci, 1988. 29(7): p. 1195-8.

183. Gerl, V. B., et al., Extensive deposits of complement C3d and C5b-9 in the choriocapillaris of eyes of patients with diabetic retinopathy. Invest Ophthalmol Vis Sci, 2002. 43(4): p. 1104-8.
184. Zhang, J., C. Gerhardinger, and M. Lorenzi, Early complement activation and decreased levels of glycosyl-phosphatidylinositol-anchored complement inhibitors in human and experimental diabetic retinopathy. Diabetes, 2002. 51(12): p. 3499-504.
185. Speth, C., et al., The role of complement in invasive fungal infections. Mycoses, 2004. 47(3-4): p. 93-103.
186. Behrens-Baumann, W., G. Scheurer, and H. Schroer, Pathogenesis of Purtscher's retinopathy. An experimental study. Graefes Arch Clin Exp Ophthalmol, 1992. 230(3): p. 286-91.
187. Rohrer, B., et al., A targeted inhibitor of the alternative complement pathway reduces angiogenesis in a mouse model of age-related macular degeneration. Invest Ophthalmol Vis Sci, 2009. 50(7): p. 3056-64.
188. Hecker, L. A., et al., Genetic control of the alternative pathway of complement in humans and age-related macular degeneration. Hum Mol Genet. 19(1): p. 209-15.
189. Machalinska, A., et al., Elevated plasma levels of C3a complement compound in the exudative form of age-related macular degeneration. Ophthalmic Res, 2009. 42(1): p. 54-9.
190. Li, W., et al., Complement 5b-9 complex-induced alterations in human RPE cell physiology. Med Sci Monit. 16(1): p. BR17-23.
191. Yanai, R., A. Thanos, and K. M. Connor, Complement involvement in neovascular ocular diseases. Adv Exp Med Biol, 2012. 946: p. 161-83.
192. Jha, P., P. S. Bora, and N. S. Bora, The role of complement system in ocular diseases including uveitis and macular degeneration. Molecular Immunology, 2007. 44(16): p. 3901-3908.
193. Lockington, D., et al., Visual improvement in established central retinal vein occlusion with long-standing macular edema following systemic eculizumab treatment. Can J Ophthalmol, 2010. 45(6): p. 649.
194. Chen, H., et al., The aged retinal pigment epithelium/choroid: a potential substratum for the pathogenesis of age-related macular degeneration. PLoS One, 2008. 3(6): p. e2339.
195. Nozaki, M., et al., Drusen complement components C3a and C5a promote choroidal neovascularization. Proc Natl Acad Sci USA, 2006. 103(7): p. 2328-33.
196. Johnson, L. V., et al., Cell culture model that mimics drusen formation and triggers complement activation associated with age-related macular degeneration. Proc Natl Acad Sci U S A, 2011. 108(45): p. 18277-82.
197. Radu, R. A., et al., Complement System Dysregulation and Inflammation in the Retinal Pigment Epithelium of a Mouse Model for Stargardt Macular Degeneration. Journal of Biological Chemistry, 2011. 286(21): p. 18593-18601.
198. Brawman-Mintzer, O, B. J. Mondino, and F. J. Mayer, Distribution of complement in the sclera. Invest Ophthalmol Vis Sci, 1989. 30(10): p. 2240-4.
199. Gay-Crosier, F., et al., Complement activation by pulsed tunable dye laser in normal skin and hemangioma. J Invest Dermatol, 1990. 94(4): p. 426-31.
200. Orr, F., et al., Detection of a complement-derived chemotactic factor for tumor cells in human inflammatory and neoplastic effusions. Am J Pathol, 1983. 110(1): p. 41-47.
201. Matsell, D. G., et al., Plasma terminal complement complexes in acute poststreptococcal glomerulonephritis. Am J Kidney Dis, 1991. 17(3): p. 311-6.
202. Sjoholm, A. G., Complement components and complement activation in acute poststreptococcal glomerulonephritis. Int Arch Allergy Appl Immunol, 1979. 58(3): p. 274-84.
203. Ohsawa, I., et al., Evidence of lectin complement pathway activation in poststreptococcal glomerulonephritis. Kidney Int, 1999. 56(3): p. 1158-9.
204. Otten, M. A., et al., Both complement and IgG fc receptors are required for development of attenuated antiglomerular basement membrane nephritis in mice. J Immunol, 2009. 183(6): p. 3980-8.
205. Teisberg, P., et al., Serial complement studies in a patient with Goodpasture's syndrome treated with bilateral nephrectomy and renal transplantation. Am J Med, 1975. 59(4): p. 563-7.
206. Gunnarsson, I., et al., Occurrence of anti-C1q antibodies in IgA nephropathy. Nephrol Dial Transplant, 1997. 12(11): p. 2263-8.
207. Humair, L. M., Beta-10-globulin and complement in nephritis. Serological and immunohistological studies in acute, chronic, membranous and lupus glomerulonephritis. Helv Med Acta, 1968. 34(4): p. 279-96.
208. Stachura, I., Immune complexes in IgA nephropathy (Berger's disease). Pathol Annu, 1983. 18 Pt 2: p. 295-314.
209. Stachura, I., G. Singh, and T. L. Whiteside, Immune abnormalities in IgA nephropathy (Berger's disease). Clin Immunol Immunopathol, 1981. 20(3): p. 373-88.
210. Brandt, J., et al., Role of the complement membrane attack complex (C5b-9) in mediating experimental mesangioproliferative glomerulonephritis. Kidney Int, 1996. 49(2): p. 335-43.
211. Sethi, S., et al., Glomeruli of Dense Deposit Disease contain components of the alternative and terminal complement pathway. Kidney Int, 2009. 75(9): p. 952-60.
212. Zipfel, P. F. and C. Skerka, Complement regulators and inhibitory proteins. Nat Rev Immunol, 2009. 9(10): p. 729-40.
213. Kotnik, V., et al., Demonstration of apoptosis-associated cleavage products of DNA, complement activation products SC5b-9 and C3d/dg, and immune complexes CIC-C3d, CIC-IgA, and CIC-IgG in the urine of patients with membranous glomerulonephritis. Croat Med J, 2003. 44(6): p. 707-11.
214. Honkanen, E., et al., Urinary excretion of cytokines and complement SC5b-9 in idiopathic membranous glomerulonephritis. Nephrol Dial Transplant, 1994. 9(11): p. 1553-9.
215. Moseley, H. L. and K. Whaley, Control of complement activation in membranous and membranoproliferative glomerulonephritis. Kidney Int, 1980. 17(4): p. 535-44.
216. de Vries, B., et al., The mannose-binding lectin-pathway is involved in complement activation in the course of renal ischemia-reperfusion injury. Am J Pathol, 2004. 165(5): p. 1677-88.
217. Farrar, C. A., et al., Independent pathways of P-selectin and complement-mediated renal ischemia/reperfusion injury. Am J Pathol, 2004. 164(1): p. 133-41.
218. de Vries, B., et al., Complement factor C5a mediates renal ischemia-reperfusion injury independent from neutrophils. J Immunol, 2003. 170(7): p. 3883-9.
219. De Vries, B., et al., Inhibition of complement factor C5 protects against renal ischemia-reperfusion injury: inhi- 219. bition of late apoptosis and inflammation. Transplantation, 2003. 75(3): p. 375-82.
220. Castellano, G., et al., Therapeutic targeting of classical and lectin pathways of complement protects from ischemia-reperfusion-induced renal damage. Am J Pathol, 2010. 176(4): p. 1648-59.
221. Kowalewska, J., Cryoglobulinemic glomerulonephritis—lessons from animal models. Folia Histochem Cytobiol, 2011. 49(4): p. 537-46.
222. Biglarnia, A. R., et al., Desensitization with antigen-specific immunoadsorption interferes with complement in ABO-incompatible kidney transplantation. Transplantation, 2012. 93(1): p. 87-92.
223. Bao, L. and R. J. Quigg, Complement in lupus nephritis: the good, the bad, and the unknown. Semin Nephrol, 2007. 27(1): p. 69-80.
224. Kiss, A., et al., A new mechanism regulating the initiation of allergic airway inflammation. J Allergy Clin Immunol, 2007. 120(2): p. 334-42.
225. Tschernig, T., et al., Use of monoclonal antibodies to assess expression of anaphylatoxin receptors in rat and murine models of lung inflammation. Exp Toxicol Pathol, 2007. 58(6): p. 419-25.
226. Fevang, B., et al., Common variable immunodeficiency and the complement system; low mannose-binding lectin levels are associated with bronchiectasis. Clin Exp Immunol, 2005. 142(3): p. 576-84.
227. Kawikova, I., et al., Airway hyper-reactivity mediated by B-1 cell immunoglobulin M antibody generating complement C5a at 1 day post-immunization in a murine hapten model of non-atopic asthma. Immunology, 2004. 113(2): p. 234-45.
228. Taggart, E. W., et al., Comparison of complement fixation with two enzyme-linked immunosorbent assays for the detection of antibodies to respiratory viral antigens. Am J Clin Pathol, 2006. 125(3): p. 460-6.
229. Yoder, S. M., et al., Role of complement in neutralization of respiratory syncytial virus. J Med Virol, 2004. 72(4): p. 688-94.
230. Smith, T. F., et al., Activation of complement by cells infected with respiratory syncytial virus. Infect Immun, 1981. 33(1): p. 43-8.
231. Johnson, J. B., G. A. Capraro, and G. D. Parks, Differential mechanisms of complement-mediated neutralization of the closely related paramyxoviruses simian virus 5 and mumps virus. Virology, 2008. 376(1): p. 112-23.
232. Tsai, V., et al., Complement component C1q and anti-hexon antibody mediate adenovirus infection of a CAR-negative cell line. Viral Immunol, 2008. 21(4): p. 469-76.
233. Schonheyder, H. and P. Andersen, Complement-binding antibodies to Aspergillus fumigatus in patients with pulmonary aspergillosis. Acta Pathol Microbiol Immunol Scand B, 1983. 91(1): p. 1-7.
234. Geha, R. S., Circulating immune complexes and activation of the complement sequence in acute allergic bronchopulmonary aspergillosis. J Allergy Clin Immunol, 1977. 60(6): p. 357-9.
235. Porcel, J. M., et al., Usefulness of pleural complement activation products in differentiating tuberculosis and malignant effusions. Int J Tuberc Lung Dis, 2000. 4(1): p. 76-82.
236. Cywes, C., et al., Nonopsonic binding of *Mycobacterium tuberculosis* to complement receptor type 3 is mediated by capsular polysaccharides and is strain dependent. Infect Immun, 1997. 65(10): p. 4258-66.
237. Lamontagne, L. R., et al., The acute phase response in parasite infection. *Nippostrongylus brasiliensis* in the mouse. Immunology, 1984. 52(4): p. 733-41.
238. Yu, G., et al., LPS-induced murine abortions require C5 but not C3, and are prevented by upregulating expression of the CD200 tolerance signaling molecule. Am J Reprod Immunol, 2008. 60(2): p. 135-40.
239. Shima, M., et al., Serum complement levels in children in communities with different levels of air pollution in Japan. Arch Environ Health, 1999. 54(4): p. 264-70.
240. Zilow, G., et al., Complement activation and the prognostic value of C3a in patients at risk of adult respiratory distress syndrome. Clin Exp Immunol, 1990. 79(2): p. 151-7.
241. Solomkin, J. S., et al., Complement activation and clearance in acute illness and injury: evidence for C5a as a cell-directed mediator of the adult respiratory distress syndrome in man. Surgery, 1985. 97(6): p. 668-78.
242. Langlois, P. F., et al., Accentuated complement activation in patient plasma during the adult respiratory distress syndrome: a potential mechanism for pulmonary inflammation. Heart Lung, 1989. 18(1): p. 71-84.
243. Papageorgiou, N., et al., Complement receptor enhancement as evidence of neutrophil activation after exercise-induced asthma. Lancet, 1983. 2(8361): p. 1220-3.
244. Gwynn, C. M. and R. A. Thompson, Complement changes during exercise-induced asthma. Clin Allergy, 1978. 8(5): p. 483-6.
245. Larsen, C. P., R. R. Regal, and J. F. Regal, Trimellitic anhydride-induced allergic response in the guinea pig lung involves antibody-dependent and -independent complement system activation. J Pharmacol Exp Ther, 2001. 296(2): p. 284-92.
246. Kohl, J. and M. Wills-Karp, A dual role for complement in allergic asthma. Curr Opin Pharmacol, 2007. 7(3): p. 283-9.
247. Karp, C. L., et al., Identification of complement factor 5 as a susceptibility locus for experimental allergic asthma. Nat Immunol, 2000. 1(3): p. 221-6.
248. Bowser, C., et al., Correlation of plasma complement split product levels with allergic respiratory disease activity and relation to allergen immunotherapy. Ann Allergy Asthma Immunol. 104(1): p. 42-9.
249. Ventura, M. T., et al., Allergic bronchial asthma: eosinophil chemotaxis and antihistaminic drug modulation. Allergy, 1996. 51(11): p. 777-81.
250. Nakano, Y., et al., Elevated complement C3a in plasma from patients with severe acute asthma. J Allergy Clin Immunol, 2003. 112(3): p. 525-30.
251. Marc, M. M., et al., Complement factors c3a, c4a, and c5a in chronic obstructive pulmonary disease and asthma. Am J Respir Cell Mol Biol, 2004. 31(2): p. 216-9.
252. Miller, R. D., F. Kueppers, and K. P. Offord, Serum concentrations of C3 and C4 of the complement system in patients with chronic obstructive pulmonary disease. J Lab Clin Med, 1980. 95(2): p. 266-71.
253. Kosmas, E. N., et al., Decreased C4 complement component serum levels correlate with the degree of emphysema in patients with chronic bronchitis. Chest, 1997. 112(2): p. 341-7.
254. Monie, R. D., R. Fifield, and B. H. Davies, Acute asthma compared with exacerbations of chronic bronchitis: changes in complement. Clin Allergy, 1979. 9(2): p. 141-5.
255. Gotz, M. and G. Lubec, Complement in cystic fibrosis. Eur J Pediatr, 1978. 127(2): p. 133-9.

256. Lambie, P. B. and F. P. Quismorio, Jr., Interstitial lung disease and cryoglobulinemia in polymyositis. J Rheumatol, 1991. 18(3): p. 468-9.
257. Dry, S. M., et al., The pathology of transfusion-related acute lung injury. Am J Clin Pathol, 1999. 112(2): p. 216-21.
258. Reissman, P., et al., Transfusion-related adult respiratory distress syndrome. Isr J Med Sci, 1993. 29(5): p. 303-7.
259. Zimmerman, J. L., et al., Phase I trial of the recombinant soluble complement receptor 1 in acute lung injury and acute respiratory distress syndrome. Crit Care Med, 2000. 28(9): p. 3149-54.
260. Weinberg, P. F., et al., Biologically active products of complement and acute lung injury in patients with the sepsis syndrome. Am Rev Respir Dis, 1984. 130(5): p. 791-6.
261. Mundie, T. G., P. A. Pilia, and S. K. Ainsworth, Byssinosis: serum immunoglobulin and complement concentrations in cotton mill workers. Arch Environ Health, 1985. 40(6): p. 326-9.
262. Mundie, T. G., R. J. Boackle, and S. K. Ainsworth, In vitro alternative and classical activation of complement by extracts of cotton mill dust: a possible mechanism in the pathogenesis of byssinosis. Environ Res, 1983. 32(1): p. 47-56.
263. Governa, M., et al., In vitro cleavage by asbestos fibers of the fifth component of human complement through free-radical generation and kallikrein activation. J Toxicol Environ Health A, 2000. 59(7): p. 539-52.
264. Fraser, D. G. and J. F. Regal, Recombinant human C5a-induced bronchoconstriction in the guinea pig: inhibition by an H1 antagonist after depletion of circulating granulocytes and platelets. J Pharmacol Exp Ther, 1991. 259(3): p. 1213-20.
265. Addis-Lieser, E., J. Kohl, and M. G. Chiaramonte, Opposing regulatory roles of complement factor 5 in the development of bleomycin-induced pulmonary fibrosis. J Immunol, 2005. 175(3): p. 1894-902.
266. Meliconi, R., et al., Complement activation products in idiopathic pulmonary fibrosis: relevance of fragment Ba to disease severity. Clin Immunol Immunopathol, 1990. 57(1): p. 64-73.
267. Acevedo, F., L. Palmberg, and K. Larsson, Exposure to organic dust causes activation of human plasma complement factors C3 and B and the synthesis of factor C3 by lung epithelial cells in vitro. Inflammation, 2005. 29(1): p. 39-45.
268. Hoffmann, H. J., et al., Plasma C3d levels of young farmers correlate with respirable dust exposure levels during normal work in swine confinement buildings. Ann Agric Environ Med, 2003. 10(1): p. 53-60.
269. Paterson, G. K. and C. J. Orihuela, Pneumococci: immunology of the innate host response. Respirology, 2010. 15(7): p. 1057-1063.
270. Governa, M., et al., Variability of biological effects of silicas: different degrees of activation of the fifth component of complement by amorphous silicas. Toxicol Appl Pharmacol, 2005. 208(1): p. 68-77.
271. Mollnes, T. E., et al., Complement activation in patients with systemic lupus erythematosus without nephritis. Rheumatology (Oxford), 1999. 38(10): p. 933-40.
272. Porcel, J. M., et al., The value of complement activation products in the assessment of systemic lupus erythematosus flares. Clin Immunol Immunopathol, 1995. 74(3): p. 283-8.
273. Belmont, H. M., et al., Complement activation during systemic lupus erythematosus. C3a and C5a anaphylatoxins circulate during exacerbations of disease. Arthritis Rheum, 1986. 29(9): p. 1085-9.
274. Neumann, E., et al., Local production of complement proteins in rheumatoid arthritis synovium. Arthritis Rheum, 2002. 46(4): p. 934-45.
275. Brodeur, J. P., et al., Synovial fluid levels of complement SC5b-9 and fragment Bb are elevated in patients with rheumatoid arthritis. Arthritis Rheum, 1991. 34(12): p. 1531-7.
276. Tausk, F. A., et al., Altered erythrocyte C3b receptor expression, immune complexes, and complement activation in homosexual men in varying risk groups for acquired immune deficiency syndrome. J Clin Invest, 1986. 78(4): p. 977-82.
277. Schiller, C., et al., Influence of suramin on the expression of Fc receptors and other markers on human monocytes and U937 cells, and on their phagocytic properties. Immunology, 1994. 81(4): p. 598-604.
278. Yaskanin, D. D., L. F. Thompson, and F. J. Waxman, Distribution and quantitative expression of the complement receptor type 1 (CR1) on human peripheral blood T lymphocytes. Cell Immunol, 1992. 142(1): p. 159-76.
279. Puppo, F., et al., Major histocompatibility gene products and human immunodeficiency virus infection. J Lab Clin Med, 1991. 117(2): p. 91-100.
280. Morrow, W. J., et al., Circulating immune complexes in patients with acquired immune deficiency syndrome contain the AIDS-associated retrovirus. Clin Immunol Immunopathol, 1986. 40(3): p. 515-24.
281. Smith, P. D., et al., Monocyte function in the acquired immune deficiency syndrome. Defective chemotaxis. J Clin Invest, 1984. 74(6): p. 2121-8.
282. Ghose, T., P. Landrigan, and A. Asif, Localization of immunoglobulin and complement in pulmonary sarcoid granulomas. Chest, 1974. 66(3): p. 264-8.
283. Cagatay, T., et al., The immunoglobulin and complement levels in the active pulmonary sarcoidosis. Kobe J Med Sci, 2003. 49(5-6): p. 99-106.
284. Lissauer, M. E., et al., Coagulation and complement protein differences between septic and uninfected systemic inflammatory response syndrome patients. J Trauma, 2007. 62(5): p. 1082-92; discussion 1092-4.
285. Castellheim, A., et al., Meconium aspiration syndrome induces complement-associated systemic inflammatory response in newborn piglets. Scand J Immunol, 2005. 61(3): p. 217-25.
286. Stove, S., et al., Circulating complement proteins in patients with sepsis or systemic inflammatory response syndrome. Clin Diagn Lab Immunol, 1996. 3(2): p. 175-83.
287. Aggarwal, A., et al., Evidence for activation of the alternate complement pathway in patients with juvenile rheumatoid arthritis. Rheumatology (Oxford), 2000. 39(2): p. 189-92.
288. Mark, L., et al., The Kaposi's sarcoma-associated herpesvirus complement control protein mimics human molecular mechanisms for inhibition of the complement system. J Biol Chem, 2004. 279(43): p. 45093-101.
289. Lipsker, D. and G. Hauptmann, Cutaneous manifestations of complement deficiencies. Lupus, 2010. 19(9): p. 1096-106.
290. Bilgin, Y. M., et al., Mannose-binding lectin is involved in multiple organ dysfunction syndrome after cardiac surgery: effects of blood transfusions. Transfusion, 2008. 48(4): p. 601-8.

291. Wang, H., et al., Inhibition of terminal complement components in presensitized transplant recipients prevents antibody-mediated rejection leading to long-term graft survival and accommodation. J Immunol, 2007. 179(7): p. 4451-63.
292. Pratt, J. R., et al., Nontransgenic hyperexpression of a complement regulator in donor kidney modulates transplant ischemia/reperfusion damage, acute rejection, and chronic nephropathy. Am J Pathol, 2003. 163(4): p. 1457-65.
293. Baldwin, W. M., H. Ota, and E. R. Rodriguez, Complement in transplant rejection: diagnostic and mechanistic considerations. Springer Semin Immunopathol, 2003. 25(2): p. 181-97.
294. Pratt, J. R., S. A. Basheer, and S. H. Sacks, Local synthesis of complement component C3 regulates acute renal transplant rejection. Nat Med, 2002. 8(6): p. 582-7.
295. Barnes, R. M., et al., Immunological evaluation of renal transplant patients: changes in levels of beta-2-microglobulin, immunoglobulins and complement components during graft rejection. J Clin Lab Immunol, 1983. 12(1): p. 17-22.
296. Rioux, P., TP-10 (AVANT Immunotherapeutics). Curr Opin Investig Drugs, 2001. 2(3): p. 364-71.
297. Robson, S. C., et al., Role of endothelial cells in transplantation. Int Arch Allergy Immunol, 1995. 106(4): p. 305-22.
298. Somerville, C. A. and A. J. d'Apice, Future directions in transplantation: xenotransplantation. Kidney Int Suppl, 1993. 42: p. S112-21.
299. Hughes, P. D. and S. J. Cohney, Modifiers of complement activation for prevention of antibody-mediated injury to allografts. Curr Opin Organ Transplant, 2011. 16(4): p. 425-33.
300. Azimzadeh, A., et al., Hyperacute lung rejection in the pig-to-human model. 2. Synergy between soluble and membrane complement inhibition. Xenotransplantation, 2003. 10(2): p. 120-31.
301. Thomas, H., et al., A synthetic dextran derivative inhibits complement activation and complement-mediated cytotoxicity in an in vitro model of hyperacute xenograft rejection. Transplant Proc, 1996. 28(2): p. 593-4.
302. Sheerin, N. S., Should Complement Activation Be a Target for Therapy in Renal Transplantation? Journal of the American Society of Nephrology, 2008. 19(12): p. 2250-2251.
303. Blomquist, M. D., et al., Monoclonal anti-T cell (T12) antibody treatment of graft-versus-host disease in severe combined immunodeficiency: targeting of antibody and activation of complement on CD8+ cytotoxic T cell surfaces. J Allergy Clin Immunol, 1991. 87(5): p. 1029-33.
304. Herve, P., et al., Successful graft-versus-host disease prevention without graft failure in 32 HLA-identical allogeneic bone marrow transplantations with marrow depleted of T cells by monoclonal antibodies and complement. Blood, 1987. 69(2): p. 388-93.
305. Heit, W., et al., Ex vivo T-cell depletion with the monoclonal antibody Campath-1 plus human complement effectively prevents acute graft-versus-host disease in allogeneic bone marrow transplantation. Br J Haematol, 1986. 64(3): p. 479-86.
306. Mitsuyasu, R. T., et al., Treatment of donor bone marrow with monoclonal anti-T-cell antibody and complement for the prevention of graft-versus-host disease. A prospective, randomized, double-blind trial. Ann Intern Med, 1986. 105(1): p. 20-6.
307. Herve, P., Depletion of T-lymphocytes in donor marrow with pan-T monoclonal antibodies and complement for prevention of acute graft-versus-host disease: a pilot study on 29 patients. J Natl Cancer Inst, 1986. 76(6): p. 1311-6.
308. Hamilton, B. L. and D. Harris, Prevention of graft-versus-host disease using antibody to Thy 1. A role for complement in vivo. Transplantation, 1985. 40(1): p. 90-6.
309. Ballow, M., R. A. Good, and N. K. Day, Complement in graft versus host disease: II. Depletion of complement components during a systemic graft versus host reaction in the rat (38499). Proc Soc Exp Biol Med, 1975. 148(1): p. 170-6.
310. Wu, W., et al., Prolonged cardiac allograft survival in mouse model after complement depletion with Yunnan cobra venom factor. Transplant Proc, 2009. 41(10): p. 4321-7.
311. Chen, S., et al., Complement Inhibition Enables Renal Allograft Accommodation and Long-Term Engraftment in Presensitized Nonhuman Primates. American Journal of Transplantation, 2011. 11(10): p. 2057-2066.
312. Lazar, H. L., et al., Total complement inhibition: an effective strategy to limit ischemic injury during coronary revascularization on cardiopulmonary bypass. Circulation, 1999. 100(13): p. 1438-42.
313. Harkin, D. W., et al., Complement C5a receptor antagonist attenuates multiple organ injury in a model of ruptured abdominal aortic aneurysm. J Vasc Surg, 2004. 39(1): p. 196-206.
314. Slotman, G. J., et al., Interaction of prostaglandins, activated complement, and granulocytes in clinical sepsis and hypotension. Surgery, 1986. 99(6): p. 744-51.
315. Nguyen, H. X., M. D. Galvan, and A. J. Anderson, Characterization of early and terminal complement proteins associated with polymorphonuclear leukocytes in vitro and in vivo after spinal cord injury. J Neuroinflammation, 2008. 5: p. 26.
316. Qiao, F., et al., Complement plays an important role in spinal cord injury and represents a therapeutic target for improving recovery following trauma. Am J Pathol, 2006. 169(3): p. 1039-47.
317. Anderson, A. J., et al., Activation of complement pathways after contusion-induced spinal cord injury. J Neurotrauma, 2004. 21(12): p. 1831-46.
318. Rebhun, J. and J. Botvin, Complement elevation in spinal cord injury. Ann Allergy, 1980. 44(5): p. 287-8.
319. van Beek, J., K. Elward, and P. Gasque, Activation of complement in the central nervous system: roles in neurodegeneration and neuroprotection. Ann N Y Acad Sci, 2003. 992: p. 56-71.
320. Davis, C. S., et al., Early pulmonary immune hyporesponsiveness is associated with mortality after burn and smoke inhalation injury. J Burn Care Res, 2012. 33(1): p. 26-35.
321. Hoesel, L. M., et al., C5a-blockade improves burn-induced cardiac dysfunction. J Immunol, 2007. 178(12): p. 7902-10.
322. Craig, R. P., Military cold injury during the war in the Falkland Islands 1982: an evaluation of possible risk factors. J R Army Med Corps, 2007. 153 Suppl 1: p. 63-8; discussion 69.
323. Ramaglia, V., et al., Soluble complement receptor 1 protects the peripheral nerve from early axon loss after injury. Am J Pathol, 2008. 172(4): p. 1043-52.

324. Ramaglia, V., et al., The membrane attack complex of the complement system is essential for rapid Wallerian degeneration. J Neurosci, 2007. 27(29): p. 7663-72.
325. Ohlsson, M., et al., Complement activation following optic nerve crush in the adult rat. J Neurotrauma, 2003. 20(9): p. 895-904.
326. Liu, L., et al., Hereditary absence of complement C5 in adult mice influences Wallerian degeneration, but not retrograde responses, following injury to peripheral nerve. J Peripher Nerv Syst, 1999. 4(2): p. 123-33.
327. Wahl, S. M., W. P. Arend, and R. Ross, The effect of complement depletion on wound healing. Am J Pathol, 1974. 75(1): p. 73-89.
328. Becker, P., et al., [Complement activation following head and brain trauma]. Anaesthesist, 1987. 36(6): p. 301-5.
329. Schmidt, O. I., et al., Closed head injury—an inflammatory disease? Brain Res Brain Res Rev, 2005. 48(2): p. 388-99.
330. Costa, C., et al., Role of complement component C5 in cerebral ischemia/reperfusion injury. Brain Res, 2006. 1100(1): p. 142-51.
331. Yin, W., et al., Regulated complement deposition on the surface of human endothelial cells: effect of tobacco smoke and shear stress. Thromb Res, 2008. 122(2): p. 221-8.
332. Holm-Bentzen, M., et al., A prospective double-blind clinically controlled multicenter trial of sodium pentosanpolysulfate in the treatment of interstitial cystitis and related painful bladder disease. J Urol, 1987. 138(3): p. 503-7.
333. Steinert, B. W., et al., Complement C3, eosinophil cationic protein and symptom evaluation in interstitial cystitis. J Urol, 1994. 151(2): p. 350-4.
334. Mattila, J., A. Harmoinen, and O. Hallstrom, Serum immunoglobulin and complement alterations in interstitial cystitis. Eur Urol, 1983. 9(6): p. 350-2.
335. Helin, H., et al., In vivo binding of immunoglobulin and complement to elastic structures in urinary bladder vascular walls in interstitial cystitis: demonstration by immunoelectron microscopy. Clin Immunol Immunopathol, 1987. 43(1): p. 88-96.
336. Bulla, R., et al., The complement system at the fetomaternal interface. Chem Immunol Allergy, 2005. 89: p. 149-57.
337. Mao, D., et al., Negligible role of antibodies and C5 in pregnancy loss associated exclusively with C3-dependent mechanisms through complement alternative pathway. Immunity, 2003. 19(6): p. 813-22.
338. Xu, C., et al., A critical role for murine complement regulator crry in fetomaternal tolerance. Science, 2000. 287(5452): p. 498-501.
339. Bulla, R., F. Bossi, and F. Tedesco, The complement system at the embryo implantation site: friend or foe? Front Immunol, 2012. 3: p. 55.
340. Girardi, G., et al., Complement activation in animal and human pregnancies as a model for immunological recognition. Mol Immunol, 2012. 48(14): p. 1621-30.
341. Ogunleye, A. O. and O. G. Arinola, Immunoglobulin classes, complement factors and circulating immune complexes in chronic sinusitis patients. Afr J Med Med Sci, 2001. 30(4): p. 309-12.
342. Miyaguchi, M., et al., Immunohistochemical studies of complement receptor (CR1) in cases with normal sinus mucosa and chronic sinusitis. Arch Otorhinolaryngol, 1988. 244(6): p. 350-4.
343. Girardi, G., Complement inhibition keeps mothers calm and avoids fetal rejection. Immunol Invest, 2008. 37(5): p. 645-59.
344. Crovetto, F., et al., The genetics of the alternative pathway of complement in the pathogenesis of HELLP syndrome. J Matern Fetal Neonatal Med, 2012.
345. D'Cruz, O. J., C. A. Toth, and G. G. Haas, Jr., Recombinant soluble human complement receptor type 1 inhibits antisperm antibody- and neutrophil-mediated injury to human sperm. Biol Reprod, 1996. 54(6): p. 1217-28.
346. Girardi, G., et al., Complement activation induces dysregulation of angiogenic factors and causes fetal rejection and growth restriction. The Journal of Experimental Medicine, 2006. 203(9): p. 2165-2175.
347. Girardi, G. and J. B. Salmon, The role of complement in pregnancy and fetal loss. Autoimmunity, 2003. 36(1): p. 19-26.

Having described the invention, the following is claimed:

1. A method of selecting a genus of therapeutic antibodies, the method comprising:
   a) determining whether an antibody inhibits alternative pathway complement activation but not classical pathway complement activation or classical pathway initiated amplification of the alternative pathway by assaying the antibody for its ability to:
      i) inhibit cell lysis under conditions wherein the alternative pathway is isolated from the classical pathway;
      ii) not inhibit cell lysis under conditions wherein the classical pathway is isolated from the alternative pathway; and
      iii) not inhibit cell lysis under conditions wherein the classical pathway activates the alternative pathway; and
   b) determining whether the antibody inhibits C3b produced exclusively by the alternative pathway;
   c) and selecting an antibody which meets steps (a) and (b) above;
   wherein the selected antibodies bind to a component of Alternative Pathway C3 Convertase, which have the specific characteristic of selectively inhibiting C3a, C5a, C3b, C5b, and C5b-9 produced exclusively by the alternative pathway, without inhibiting any of the classical pathway's ability to produce C3a, C5a, C3b, C5b, and C5b-9 at levels sufficient to maintain normal host defense.

2. The method of claim 1, wherein the antibody binds to P, Bb, C3b, or Ba.

* * * * *

SEQUENCE LISTING

<160> NUMBER OF SEQ ID NOS: 60

<210> SEQ ID NO 1
<211> LENGTH: 101
<212> TYPE: PRT
<213> ORGANISM: Mus musculus

<400> SEQUENCE: 1

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Phe Phe
            20                  25                  30

Leu Asn Trp Tyr Gln Gln Lys Pro Asp Gly Thr Val Lys Leu Leu Ile
        35                  40                  45

Tyr Tyr Thr Ser Arg Tyr His Ser Gly Val Pro Ser Arg Phe Ser Gly
    50                  55                  60

Ser Gly Ser Gly Thr Asp Phe Ser Leu Thr Ile Asn Asn Leu Glu Gln
65                  70                  75                  80

Glu Asp Phe Ala Thr Tyr Phe Cys Gln His Gly Asn Thr Leu Pro Trp
```

-continued

```
                    85                  90                  95

Thr Phe Gly Gly Gly
            100

<210> SEQ ID NO 2
<211> LENGTH: 11
<212> TYPE: PRT
<213> ORGANISM: Mus musculus

<400> SEQUENCE: 2

Arg Ala Ser Gln Asp Ile Ser Phe Phe Leu Asn
1               5                   10

<210> SEQ ID NO 3
<211> LENGTH: 7
<212> TYPE: PRT
<213> ORGANISM: Mus musculus

<400> SEQUENCE: 3

Tyr Thr Ser Arg Tyr His Ser
1               5

<210> SEQ ID NO 4
<211> LENGTH: 9
<212> TYPE: PRT
<213> ORGANISM: Mus musculus

<400> SEQUENCE: 4

Gln His Gly Asn Thr Leu Pro Trp Thr
1               5

<210> SEQ ID NO 5
<211> LENGTH: 106
<212> TYPE: PRT
<213> ORGANISM: Mus musculus

<400> SEQUENCE: 5

Asp Ile Gln Met Thr Gln Ser Pro Leu Ser Leu Ser Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Asn
                85                  90                  95

Thr His Val Pro Arg Thr Phe Gly Gly Gly
            100                 105

<210> SEQ ID NO 6
<211> LENGTH: 16
<212> TYPE: PRT
<213> ORGANISM: Mus musculus

<400> SEQUENCE: 6

Arg Ser Ser Gln Ser Leu Val His Ser Asn Gly Asn Thr Tyr Leu His
1               5                   10                  15
```

```
<210> SEQ ID NO 7
<211> LENGTH: 7
<212> TYPE: PRT
<213> ORGANISM: Mus musculus

<400> SEQUENCE: 7

Lys Val Ser Tyr Arg Phe Ser
1               5

<210> SEQ ID NO 8
<211> LENGTH: 9
<212> TYPE: PRT
<213> ORGANISM: Mus musculus

<400> SEQUENCE: 8

Ser Gln Asn Thr His Val Pro Arg Thr
1               5

<210> SEQ ID NO 9
<211> LENGTH: 111
<212> TYPE: PRT
<213> ORGANISM: Oryctolagus cuniculus

<400> SEQUENCE: 9

Ala Tyr Asp Leu Thr Gln Thr Pro Ala Ser Val Glu Ala Ala Val Gly
1               5                   10                  15

Gly Thr Val Thr Ile Asn Cys Gln Ala Ser Asp Asn Ile Tyr Ser Leu
            20                  25                  30

Leu Ala Trp Tyr Gln Gln Lys Pro Gly Gln Pro Pro Lys Leu Leu Ile
        35                  40                  45

Tyr Arg Ala Ser Thr Leu Ala Ser Gly Val Pro Ser Arg Phe Lys Gly
    50                  55                  60

Ser Gly Ser Gly Thr Gln Phe Thr Leu Thr Ile Ser Gly Val Glu Cys
65                  70                  75                  80

Ala Asp Ala Ala Thr Tyr Tyr Cys Gln Gln His Tyr Asp Tyr Asn Tyr
                85                  90                  95

Leu Asp Val Ala Phe Gly Gly Gly Thr Glu Val Val Val Lys Gly
            100                 105                 110

<210> SEQ ID NO 10
<211> LENGTH: 11
<212> TYPE: PRT
<213> ORGANISM: Oryctolagus cuniculus

<400> SEQUENCE: 10

Gln Ala Ser Asp Asn Ile Tyr Ser Leu Leu Ala
1               5                   10

<210> SEQ ID NO 11
<211> LENGTH: 7
<212> TYPE: PRT
<213> ORGANISM: Oryctolagus cuniculus

<400> SEQUENCE: 11

Arg Ala Ser Thr Leu Ala Ser
1               5

<210> SEQ ID NO 12
<211> LENGTH: 12
<212> TYPE: PRT
<213> ORGANISM: Oryctolagus cuniculus

<400> SEQUENCE: 12
```

```
Gln Gln His Tyr Asp Tyr Asn Tyr Leu Asp Val Ala
1               5                   10
```

<210> SEQ ID NO 13
<211> LENGTH: 108
<212> TYPE: PRT
<213> ORGANISM: Mus musculus

<400> SEQUENCE: 13

```
Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Asp Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asp Glu Tyr Pro Trp
                85                  90                  95

Thr Phe Gly Gly Gly Thr Lys Leu Glu Ile Lys Arg
            100                 105
```

<210> SEQ ID NO 14
<211> LENGTH: 11
<212> TYPE: PRT
<213> ORGANISM: Mus musculus

<400> SEQUENCE: 14

```
Arg Ala Ser Lys Ser Ile Ser Lys Tyr Leu Ala
1               5                   10
```

<210> SEQ ID NO 15
<211> LENGTH: 7
<212> TYPE: PRT
<213> ORGANISM: Mus musculus

<400> SEQUENCE: 15

```
Ser Gly Ser Thr Leu Gln Ser
1               5
```

<210> SEQ ID NO 16
<211> LENGTH: 9
<212> TYPE: PRT
<213> ORGANISM: Mus musculus

<400> SEQUENCE: 16

```
Gln Gln His Asp Glu Tyr Pro Trp Thr
1               5
```

<210> SEQ ID NO 17
<211> LENGTH: 112
<212> TYPE: PRT
<213> ORGANISM: Oryctolagus cuniculus

<400> SEQUENCE: 17

```
Ala Val Val Leu Thr Gln Thr Ala Ser Pro Val Ser Gly Val Val Gly
1               5                   10                  15

Gly Thr Val Thr Ile Asn Cys Gln Ala Ser Glu Asn Ile Tyr Ser Arg
            20                  25                  30
```

```
Leu Ala Trp Tyr Gln Gln Lys Pro Gly Gln Pro Pro Arg Val Leu Ile
        35                  40                  45

Tyr Tyr Ala Ser Asp Leu Ala Ser Gly Val Pro Ser Arg Phe Gly Gly
50                  55                  60

Ser Gly Ser Gly Thr Asp Tyr Thr Leu Thr Ile Ser Asp Leu Glu Cys
65                  70                  75                  80

Ala Asp Ala Ala Thr Tyr Tyr Cys His Ser Tyr Tyr Trp Asn Ser Ala
                85                  90                  95

Tyr Ser Asp Asn Thr Phe Gly Gly Gly Thr Glu Val Val Val Glu Gly
            100                 105                 110

<210> SEQ ID NO 18
<211> LENGTH: 11
<212> TYPE: PRT
<213> ORGANISM: Oryctolagus cuniculus

<400> SEQUENCE: 18

Gln Ala Ser Glu Asn Ile Tyr Ser Arg Leu Ala
1               5                   10

<210> SEQ ID NO 19
<211> LENGTH: 7
<212> TYPE: PRT
<213> ORGANISM: Oryctolagus cuniculus

<400> SEQUENCE: 19

Tyr Ala Ser Asp Leu Ala Ser
1               5

<210> SEQ ID NO 20
<211> LENGTH: 13
<212> TYPE: PRT
<213> ORGANISM: Oryctolagus cuniculus

<400> SEQUENCE: 20

His Ser Tyr Tyr Trp Asn Ser Ala Tyr Ser Asp Asn Thr
1               5                   10

<210> SEQ ID NO 21
<211> LENGTH: 111
<212> TYPE: PRT
<213> ORGANISM: Oryctolagus cuniculus

<400> SEQUENCE: 21

Asp Val Val Met Thr Gln Thr Pro Ser Ser Val Glu Ala Ala Val Gly
1               5                   10                  15

Gly Thr Val Thr Ile Lys Cys Gln Ala Ser Glu Asn Ile Tyr Ser Tyr
            20                  25                  30

Leu Ala Trp Tyr Gln Gln Lys Pro Gly Gln Pro Pro Lys Leu Leu Ile
        35                  40                  45

Tyr Lys Ala Ser Tyr Leu Ala Ser Gly Val Ser Ser Arg Phe Lys Gly
50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Leu Ser Thr Ile Ala Ser Ala Ser
                85                  90                  95

Asn Phe Asp Ala Phe Gly Gly Gly Thr Glu Val Val Val Lys Gly
            100                 105                 110
```

-continued

<210> SEQ ID NO 22
<211> LENGTH: 11
<212> TYPE: PRT
<213> ORGANISM: Oryctolagus cuniculus

<400> SEQUENCE: 22

Gln Ala Ser Glu Asn Ile Tyr Ser Tyr Leu Ala
1               5                   10

<210> SEQ ID NO 23
<211> LENGTH: 7
<212> TYPE: PRT
<213> ORGANISM: Oryctolagus cuniculus

<400> SEQUENCE: 23

Lys Ala Ser Tyr Leu Ala Ser
1               5

<210> SEQ ID NO 24
<211> LENGTH: 12
<212> TYPE: PRT
<213> ORGANISM: Oryctolagus cuniculus

<400> SEQUENCE: 24

Leu Ser Thr Ile Ala Ser Ala Ser Asn Phe Asp Ala
1               5                   10

<210> SEQ ID NO 25
<211> LENGTH: 114
<212> TYPE: PRT
<213> ORGANISM: Oryctolagus cuniculus

<400> SEQUENCE: 25

Asp Pro Val Leu Thr Gln Thr Ala Ser Ser Val Ser Ala Pro Val Gly
1               5                   10                  15

Gly Thr Val Thr Ile Ser Cys Gln Ser Ser Gln Ser Val Tyr Arg Ser
            20                  25                  30

Asn Asn Val Ala Trp Tyr Gln Gln Lys Pro Gly Lys Pro Pro Lys Leu
        35                  40                  45

Leu Ile Tyr Glu Ala Ser Ser Leu Ala Ser Gly Val Pro Ser Arg Phe
    50                  55                  60

Thr Gly Ser Gly Ser Gly Thr Gln Phe Thr Leu Thr Ile Ser Gly Val
65                  70                  75                  80

Gln Cys Asp Asp Ala Ala Thr Tyr Tyr Cys Ala Gly Gly Tyr Ser Ser
                85                  90                  95

Ser Val Asp Phe Phe Ala Phe Gly Gly Gly Thr Glu Val Val Val
                100                 105                 110

Lys Gly

<210> SEQ ID NO 26
<211> LENGTH: 13
<212> TYPE: PRT
<213> ORGANISM: Oryctolagus cuniculus

<400> SEQUENCE: 26

Gln Ser Ser Gln Ser Val Tyr Arg Ser Asn Asn Val Ala
1               5                   10

<210> SEQ ID NO 27
<211> LENGTH: 7
<212> TYPE: PRT
<213> ORGANISM: Oryctolagus cuniculus

```
<400> SEQUENCE: 27

Glu Ala Ser Ser Leu Ala Ser
1               5

<210> SEQ ID NO 28
<211> LENGTH: 13
<212> TYPE: PRT
<213> ORGANISM: Oryctolagus cuniculus

<400> SEQUENCE: 28

Ala Gly Gly Tyr Ser Ser Ser Val Asp Phe Phe Ala
1               5                   10

<210> SEQ ID NO 29
<211> LENGTH: 106
<212> TYPE: PRT
<213> ORGANISM: Humanized

<400> SEQUENCE: 29

Glu Ile Val Leu Thr Gln Ser Pro Ala Thr Leu Ser Ala Ser Pro Gly
1               5                   10                  15

Glu Lys Val Thr Met Thr Cys Ser Ala Thr Ser Ser Ile Thr Tyr Ile
            20                  25                  30

His Trp Tyr Gln Gln Lys Ser Gly Thr Ser Pro Lys Arg Trp Ile Tyr
        35                  40                  45

Asp Thr Ser Arg Leu Ala Ser Gly Val Pro Ala Arg Phe Ser Gly Ser
    50                  55                  60

Gly Ser Gly Thr Ser Tyr Ser Leu Thr Ile Ser Thr Met Glu Ala Glu
65                  70                  75                  80

Asp Ala Ala Thr Tyr Tyr Cys Gln Gln Trp Ser Ser Asn Pro Pro Thr
                85                  90                  95

Phe Gly Gly Gly Thr Lys Leu Glu Ile Lys
            100                 105

<210> SEQ ID NO 30
<211> LENGTH: 10
<212> TYPE: PRT
<213> ORGANISM: Humanized

<400> SEQUENCE: 30

Ser Ala Thr Ser Ser Ile Thr Tyr Ile His
1               5                   10

<210> SEQ ID NO 31
<211> LENGTH: 7
<212> TYPE: PRT
<213> ORGANISM: Humanized

<400> SEQUENCE: 31

Asp Thr Ser Arg Leu Ala Ser
1               5

<210> SEQ ID NO 32
<211> LENGTH: 9
<212> TYPE: PRT
<213> ORGANISM: Humanized

<400> SEQUENCE: 32

Gln Gln Trp Ser Ser Asn Pro Pro Thr
1               5
```

<210> SEQ ID NO 33
<211> LENGTH: 111
<212> TYPE: PRT
<213> ORGANISM: Mus musculus

<400> SEQUENCE: 33

Glu Val Gln Leu Gln Gln Ser Val Pro Glu Leu Ala Arg Pro Gly Ala
1               5                   10                  15

Ser Val Lys Met Ser Cys Thr Ala Ser Gly Tyr Ile Phe Thr Thr Tyr
            20                  25                  30

Pro Ile His Trp Val Lys Gln Arg Pro Gly Gln Gly Leu Glu Trp Ile
        35                  40                  45

Gly Phe Ile Asp Pro Gly Gly Tyr Asp Glu Pro Asp Asp Lys Phe
    50                  55                  60

Arg Asp Arg Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Tyr Cys
                85                  90                  95

Ala Arg Arg Gly Asp Gly Tyr Tyr Phe Asp Tyr Trp Gly Gln Gly
            100                 105                 110

<210> SEQ ID NO 34
<211> LENGTH: 10
<212> TYPE: PRT
<213> ORGANISM: Mus musculus

<400> SEQUENCE: 34

Gly Tyr Ile Phe Thr Thr Tyr Pro Ile His
1               5                   10

<210> SEQ ID NO 35
<211> LENGTH: 17
<212> TYPE: PRT
<213> ORGANISM: Mus musculus

<400> SEQUENCE: 35

Phe Ile Asp Pro Gly Gly Gly Tyr Asp Glu Pro Asp Asp Lys Phe Arg
1               5                   10                  15

Asp

<210> SEQ ID NO 36
<211> LENGTH: 9
<212> TYPE: PRT
<213> ORGANISM: Mus musculus

<400> SEQUENCE: 36

Arg Gly Asp Gly Tyr Tyr Phe Asp Tyr
1               5

<210> SEQ ID NO 37
<211> LENGTH: 123
<212> TYPE: PRT
<213> ORGANISM: Oryctolagus cuniculus

<400> SEQUENCE: 37

Gln Ser Leu Glu Glu Ser Gly Gly Gly Leu Val Lys Pro Gly Ala Ser
1               5                   10                  15

Leu Thr Leu Thr Cys Thr Ala Ser Gly Phe Ser Phe Ser Ser Gly Tyr
            20                  25                  30

Trp Ile Phe Trp Val Arg Gln Ala Pro Gly Lys Gly Leu Glu Leu Val

```
                35                  40                  45
Gly Gly Ile Tyr Ser Gly Ser Ser Gly Thr Thr Tyr Tyr Ala Asn Trp
        50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Ser Val Asp Gly Ile Asp Ser Tyr Asp Ala Ala Phe Asn Leu
            100                 105                 110

Trp Gly Pro Gly Thr Leu Val Thr Val Ser Ser
        115                 120

<210> SEQ ID NO 38
<211> LENGTH: 11
<212> TYPE: PRT
<213> ORGANISM: Oryctolagus cuniculus

<400> SEQUENCE: 38

Gly Phe Ser Phe Ser Ser Gly Tyr Trp Ile Phe
1               5                   10

<210> SEQ ID NO 39
<211> LENGTH: 18
<212> TYPE: PRT
<213> ORGANISM: Oryctolagus cuniculus

<400> SEQUENCE: 39

Gly Ile Tyr Ser Gly Ser Ser Gly Thr Thr Tyr Tyr Ala Asn Trp Ala
1               5                   10                  15

Lys Gly

<210> SEQ ID NO 40
<211> LENGTH: 14
<212> TYPE: PRT
<213> ORGANISM: Oryctolagus cuniculus

<400> SEQUENCE: 40

Ser Val Asp Gly Ile Asp Ser Tyr Asp Ala Ala Phe Asn Leu
1               5                   10

<210> SEQ ID NO 41
<211> LENGTH: 118
<212> TYPE: PRT
<213> ORGANISM: Oryctolagus cuniculus

<400> SEQUENCE: 41

Gln Ser Leu Glu Glu Ser Gly Gly Arg Leu Val Thr Pro Gly Thr Pro
1               5                   10                  15

Leu Thr Leu Thr Cys Thr Val Ser Gly Phe Asp Leu Ser Thr Tyr Ala
            20                  25                  30

Met Ser Trp Val Arg Gln Ala Pro Gly Lys Gly Leu Glu Trp Ile Gly
        35                  40                  45

Ala Val Ser Ala Thr Thr Gly Asn Thr Tyr Tyr Ala Thr Trp Ala Lys
    50                  55                  60

Gly Arg Phe Thr Met Ser Lys Ala Ser Thr Thr Val Asp Leu Lys Ile
65                  70                  75                  80

Thr Ser Pro Thr Thr Glu Asp Thr Ala Thr Tyr Phe Cys Val Arg Tyr
                85                  90                  95

Ala Ser Ser Gly Val Gly Thr Tyr Phe Asp Leu Trp Gly Gln Gly Thr
```

100                 105                 110

Leu Val Thr Val Ser Ser
            115

<210> SEQ ID NO 42
<211> LENGTH: 10
<212> TYPE: PRT
<213> ORGANISM: Oryctolagus cuniculus

<400> SEQUENCE: 42

Gly Phe Asp Leu Ser Thr Tyr Ala Met Ser
1               5                   10

<210> SEQ ID NO 43
<211> LENGTH: 17
<212> TYPE: PRT
<213> ORGANISM: Oryctolagus cuniculus

<400> SEQUENCE: 43

Ala Val Ser Ala Thr Thr Gly Asn Thr Tyr Tyr Ala Thr Trp Ala Lys
1               5                   10                  15

Gly

<210> SEQ ID NO 44
<211> LENGTH: 12
<212> TYPE: PRT
<213> ORGANISM: Oryctolagus cuniculus

<400> SEQUENCE: 44

Tyr Ala Ser Ser Gly Val Gly Thr Tyr Phe Asp Leu
1               5                   10

<210> SEQ ID NO 45
<211> LENGTH: 115
<212> TYPE: PRT
<213> ORGANISM: Oryctolagus cuniculus

<400> SEQUENCE: 45

Gln Ser Leu Glu Glu Ser Gly Gly Arg Leu Val Thr Pro Gly Gly Ser
1               5                   10                  15

Leu Thr Leu Thr Cys Thr Val Ser Gly Phe Ser Leu Ser Asn Tyr His
            20                  25                  30

Leu Gly Trp Val Arg Arg Ala Pro Gly Lys Gly Leu Glu Trp Ile Gly
        35                  40                  45

Val Ile Thr Tyr Gly Gly Ser Thr Tyr Tyr Ala Ser Trp Val Lys Gly
    50                  55                  60

Arg Phe Thr Ile Ser Lys Thr Ser Thr Thr Val Asp Leu Lys Met Thr
65                  70                  75                  80

Ser Leu Thr Thr Glu Asp Thr Ala Thr Tyr Phe Cys Ala Arg Arg Asp
                85                  90                  95

Ser Gly Gly Tyr His Leu Asp Leu Trp Gly Gln Gly Thr Leu Val Thr
            100                 105                 110

Ile Ser Ser
        115

<210> SEQ ID NO 46
<211> LENGTH: 10
<212> TYPE: PRT
<213> ORGANISM: Oryctolagus cuniculus

<400> SEQUENCE: 46

Gly Phe Ser Leu Ser Asn Tyr His Leu Gly
1               5                   10

<210> SEQ ID NO 47
<211> LENGTH: 16
<212> TYPE: PRT
<213> ORGANISM: Oryctolagus cuniculus

<400> SEQUENCE: 47

Val Ile Thr Tyr Gly Gly Ser Thr Tyr Tyr Ala Ser Trp Val Lys Gly
1               5                   10                  15

<210> SEQ ID NO 48
<211> LENGTH: 10
<212> TYPE: PRT
<213> ORGANISM: Oryctolagus cuniculus

<400> SEQUENCE: 48

Arg Asp Ser Gly Gly Tyr His Leu Asp Leu
1               5                   10

<210> SEQ ID NO 49
<211> LENGTH: 109
<212> TYPE: PRT
<213> ORGANISM: Oryctolagus cuniculus

<400> SEQUENCE: 49

Gln Ser Val Glu Glu Ser Gly Gly Arg Leu Val Thr Pro Gly Gly Ser
1               5                   10                  15

Leu Thr Leu Thr Cys Thr Val Ser Gly Phe Ser Leu Ser Asn Ala
            20                  25                  30

Ile Asn Trp Val Arg Gln Ala Pro Gly Glu Gly Leu Asp Trp Ile Gly
        35                  40                  45

Thr Ile His Thr Asn Thr Lys Thr Tyr Tyr Ala Thr Trp Ala Arg Gly
    50                  55                  60

Arg Phe Thr Ile Ser Arg Thr Ser Ser Thr Thr Val Asp Leu Lys Val
65                  70                  75                  80

Thr Ser Leu Thr Ala Ala Asp Thr Ala Thr Tyr Phe Cys Gly Arg Ala
                85                  90                  95

Asp Leu Trp Gly Gln Gly Thr Leu Val Thr Val Ser Ser
            100                 105

<210> SEQ ID NO 50
<211> LENGTH: 10
<212> TYPE: PRT
<213> ORGANISM: Oryctolagus cuniculus

<400> SEQUENCE: 50

Gly Phe Ser Leu Ser Ser Asn Ala Ile Asn
1               5                   10

<210> SEQ ID NO 51
<211> LENGTH: 16
<212> TYPE: PRT
<213> ORGANISM: Oryctolagus cuniculus

<400> SEQUENCE: 51

Thr Ile His Thr Asn Thr Lys Thr Tyr Tyr Ala Thr Trp Ala Arg Gly
1               5                   10                  15

<210> SEQ ID NO 52

```
<211> LENGTH: 3
<212> TYPE: PRT
<213> ORGANISM: Oryctolagus cuniculus

<400> SEQUENCE: 52

Ala Asp Leu
1

<210> SEQ ID NO 53
<211> LENGTH: 120
<212> TYPE: PRT
<213> ORGANISM: Humanized

<400> SEQUENCE: 53

Gln Val Gln Leu Val Gln Ser Gly Ala Glu Ile Val Lys Pro Gly Ala
1               5                   10                  15

Ser Val Lys Met Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
        35                  40                  45

Gly Asp Ile Tyr Pro Val Arg Gly Ile Thr Asn Tyr Ser Glu Lys Phe
    50                  55                  60

Lys Asn Lys Ala Lys Met Ile Pro Asp Thr Ser Ser Thr Val Tyr
65                  70                  75                  80

Met Gln Leu Ser Ser Leu Thr Ser Glu Asp Thr Ala Val Tyr Tyr Cys
                85                  90                  95

Ser Arg Gly Asn Phe Gly Asn Phe Asp Ala Met Asp Tyr Trp Gly Gln
            100                 105                 110

Gly Thr Met Val Thr Val Ser Ser
        115                 120

<210> SEQ ID NO 54
<211> LENGTH: 10
<212> TYPE: PRT
<213> ORGANISM: Humanized

<400> SEQUENCE: 54

Gly Tyr Thr Phe Thr Ser Tyr Trp Ile Asn
1               5                   10

<210> SEQ ID NO 55
<211> LENGTH: 17
<212> TYPE: PRT
<213> ORGANISM: Humanized

<400> SEQUENCE: 55

Asp Ile Tyr Pro Val Arg Gly Ile Thr Asn Tyr Ser Glu Lys Phe Lys
1               5                   10                  15

Asn

<210> SEQ ID NO 56
<211> LENGTH: 11
<212> TYPE: PRT
<213> ORGANISM: Humanized

<400> SEQUENCE: 56

Gly Asn Phe Gly Asn Phe Asp Ala Met Asp Tyr
1               5                   10

<210> SEQ ID NO 57
<211> LENGTH: 121
```

```
<212> TYPE: PRT
<213> ORGANISM: Humanized

<400> SEQUENCE: 57

Gln Val Gln Leu Gln Gln Ser Gly Ala Glu Leu Ala Lys Pro Gly Ala
1               5                   10                  15

Ser Val Arg Met Ser Cys Lys Ala Ser Gly Tyr Thr Phe Thr Asn Tyr
                20                  25                  30

Trp Ile His Trp Val Lys Gln Arg Pro Gly Gln Gly Leu Glu Trp Ile
            35                  40                  45

Gly Tyr Ile Asn Pro Asn Thr Gly Tyr Asn Asp Tyr Asn Gln Lys Phe
        50                  55                  60

Lys Asp Lys Ala Thr Leu Thr Ala Asp Lys Ser Ser Ser Thr Val Tyr
65                  70                  75                  80

Met Gln Leu Ser Ser Leu Thr Ser Glu Asp Ser Ala Val Tyr Tyr Cys
                85                  90                  95

Ala Arg Gly Gly Gln Leu Gly Leu Arg Arg Ala Met Asp Tyr Trp Gly
            100                 105                 110

Gln Gly Thr Ser Val Thr Val Ser Ser
        115                 120

<210> SEQ ID NO 58
<211> LENGTH: 10
<212> TYPE: PRT
<213> ORGANISM: Humanized

<400> SEQUENCE: 58

Gly Tyr Thr Phe Thr Asn Tyr Trp Ile His
1               5                   10

<210> SEQ ID NO 59
<211> LENGTH: 17
<212> TYPE: PRT
<213> ORGANISM: Humanized

<400> SEQUENCE: 59

Tyr Ile Asn Pro Asn Thr Gly Tyr Asn Asp Tyr Asn Gln Lys Phe Lys
1               5                   10                  15

Asp

<210> SEQ ID NO 60
<211> LENGTH: 12
<212> TYPE: PRT
<213> ORGANISM: Humanized

<400> SEQUENCE: 60

Gly Gly Gln Leu Gly Leu Arg Arg Ala Met Asp Tyr
1               5                   10
```